US005883228A

United States Patent [19]

[11] Patent Number: 5,883,228

[45] **Date of Patent: *Mar. 16, 1999**

Darnell, Jr. et al.

[54] FUNCTIONALLY ACTIVE REGIONS OF SIGNAL TRANSDUCER AND ACTIVATOR OF TRANSCRIPTION

[75] Inventors: James E. Darnell, Jr., Larchmont; Zilong Wen, New York; Curt M. Horvath, New York; Zhong Zhong, New York, all of N.Y.

[73] Assignee: The Rockefeller University, New York, N.Y.

[ * ] Notice: The term of this patent shall not extend beyond the expiration date of Pat. No. 5,716,622.

[21] Appl. No.: 852,091

[22] Filed: May 6, 1997

Related U.S. Application Data

[63] Continuation of Ser. No. 369,796, Jan. 6, 1995, Pat. No. 5,716,622.

[51] Int. Cl.[6] .............................. C07K 1/00; A61K 38/17

[52] U.S. Cl. .......................... 530/350; 530/810; 530/827; 530/358; 530/402

[58] Field of Search .................................... 530/350, 810, 530/827, 358, 402

[56] References Cited

U.S. PATENT DOCUMENTS 5,480,972 1/1996 Avjioglu et al. ........................ 530/379

FOREIGN PATENT DOCUMENTS

WO 92/00252 1/1992 WIPO .
WO 93/19179 9/1993 WIPO .

OTHER PUBLICATIONS

Burly(1994), Curr. Opin. Struct. Biol., 4:3–11.
Cicchetti(1992), Science, 257:803–6.
Horvath(1995), Genes and Development, 9:984–94.
Lew(1989), Mol. Cell Biol., 9:5404–11.
Nakajima et al. (1996) EMBO J. 15:3651–8.
Pellegrini(1989), Mol. Cell Biol., 9:4605–12.
Wen et al. (1995) Cell 82:241–50.
Darnell et al., 1994, Science 264:1415–1421.
Improta et al., 1994, Proc. Natl. Acad. Sci. USA 91:4776–80.
Shuai et al., 1994, Cell 76:821–28.
Zhong et al., 1994, Proc. Natl. Acad. Sci. USA 91:4806–4810.
Zhong et al., 1994, Science 264:95–98.
Eck et al., 1993, Nature 362:87–91.
Felder et al., 1993, Mol. Cell. Biol. 13:1449–55.
Khan et al., 1993, Proc. Natl. Acad. Sci. USA 90:6806–10.
Müller et al., 1993, EMBO J. 12:4221–28.
Müller et al., 1993, Nature 366:129–35.
Pearse et al., 1993, Proc. Natl. Acad. Sci. 90:4314–18.
Sadowski et al., 1993, Nature 362:79–83.
Sadowski et al., 1993, Science 261:1739–44.
Shuai et al., 1993, Nature 366:580–83.
Shuai et al., 1993, Science 261:1744–46.
Songyang et al., 1993, Cell 72:767–78.
Watling et al., 1993, Nature 366:166–70.
Wegenka et al., 1993, Mol. Cell. Biol. 13:276–88.
Schindler et al., 1992, Proc. Natl. Acad. Sci. USA 89:7836–39.
Schindler et al., 1992, Science 257:809–13.
Decker et al., 1991, EMBO J. 10:927–32.
Lew et al., 1991, Mol. Cell. Biol. 11:182–91.
Fu et al., 1990, Proc. Natl. Acad. Sci. USA 87:8555–59.
Wagner et al., 1990, EMBO J. 9:4477–84.

*Primary Examiner*—David Saunders
*Assistant Examiner*—F. Pierre VanderVegt
*Attorney, Agent, or Firm*—Klauber & Jackson

[57] ABSTRACT

The present invention relates generally to intracellular receptor recognition proteins or factors, termed Signal Transducers and Activators of Transcription (STAT), to methods and compositions utilizing such factors, and to the antibodies reactive toward them, in assays and for diagnosing, preventing and/or treating cellular debilitation, derangement or dysfunction. More particularly, the present invention relates to particular functional domains of molecules that exhibit both receptor recognition and message delivery via DNA binding in receptor-ligand specific manner, i.e., that directly participate both in the interaction with the ligand-bound receptor at the cell surface and in the activity of transcription in the nucleus as a DNA binding protein. The invention likewise relates to the antibodies and other entities that are specific to the functional domain of a STAT protein and that would thereby selectively modulate its activity.

13 Claims, 17 Drawing Sheets

FIG.6

```
                                                                 508
______
SLPVVV ISNVSQLPSGWASILWYNM LVAEPRNLSF FLTPPCARWA QLSEVLSWQF SS
SLPVVV ISNICQMPNAWASILWYNM LTNNPKNVNF FTKPPIGTWD QVAEVLSWQF SS
SLPVVM ISNVSQLPNAWASIIWYNV STNDSQNLVF FNNPPSVTLG QLLEVMSWQF SS
SLPVVV IVHGSQDHNATATVLWDNA FAEPGRVP.. FAVPDKVLWP QLCEALNMKF KA
SLPLVV IVHGNQDNNAKATILWDNA FSEMDRVP.. FVVAERVPWE KMCETLNLKF MA
TLPVVI ISNMNQLSIAWASVLWFNL LSPNLQNQQF FSNPPKAPWS LLGPALSWQF SS

---B--------->       <----------B--------->  <-----h----->
<-----B------> <--h--><---B--->      <--B-->   <-----h---->
<-----B------> <--- h--><--B-->       <--B-->   <----H--->
  <---B--->       <---B--><--H--><--B-->     <------h----->
---------->      <-------H-------> <---B-->  <------h------>
<-----------B-----------> <-----B------> <-----h----->
```

A

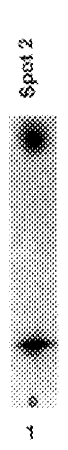
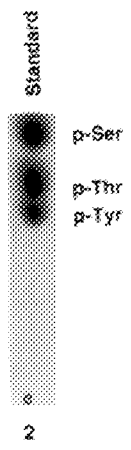
FIG.10H FIG.10I
FIG.10J
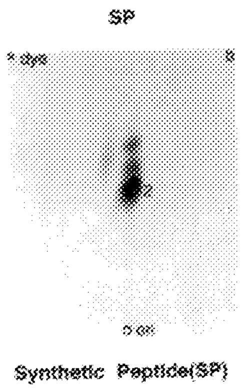
FIG.10K
FIG.10L

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
( A ) LENGTH: 3268 base pairs
( B ) TYPE: nucleic acid
( C ) STRANDEDNESS: both
( D ) TOPOLOGY: unknown -continued ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens ( v i i ) IMMEDIATE SOURCE:
( B ) CLONE: HeLa ( i x ) FEATURE:
( A ) NAME/KEY: CDS
( B ) LOCATION: 25..2577

( x i ) SEQUENCE DESCRIPTION: SEQ ID NO:1:

```
ACTGCAACCC TAATCAGAGC CCAA ATG GCG CAG TGG GAA ATG CTG CAG AAT     51
                           Met Ala Gln Trp Glu Met Leu Gln Asn
                             1               5

CTT GAC AGC CCC TTT CAG GAT CAG CTG CAC CAG CTT TAC TCG CAC AGC    99
Leu Asp Ser Pro Phe Gln Asp Gln Leu His Gln Leu Tyr Ser His Ser
 10                  15                  20                  25

CTC CTG CCT GTG GAC ATT CGA CAG TAC TTG GCT GTC TGG ATT GAA GAC   147
Leu Leu Pro Val Asp Ile Arg Gln Tyr Leu Ala Val Trp Ile Glu Asp
                 30                  35                  40

CAG AAC TGG CAG GAA GCT GCA CTT GGG AGT GAT GAT TCC AAG GCT ACC   195
Gln Asn Trp Gln Glu Ala Ala Leu Gly Ser Asp Asp Ser Lys Ala Thr
             45                  50                  55

ATG CTA TTC TTC CAC TTC TTG GAT CAG CTG AAC TAT GAG TGT GGC CGT   243
Met Leu Phe Phe His Phe Leu Asp Gln Leu Asn Tyr Glu Cys Gly Arg
         60                  65                  70

TGC AGC CAG GAC CCA GAG TCC TTG TTG CTG CAG CAC AAT TTG CGG AAA   291
Cys Ser Gln Asp Pro Glu Ser Leu Leu Leu Gln His Asn Leu Arg Lys
     75                  80                  85

TTC TGC CGG GAC ATT CAG CCC TTT TCC CAG GAT CCT ACC CAG TTG GCT   339
Phe Cys Arg Asp Ile Gln Pro Phe Ser Gln Asp Pro Thr Gln Leu Ala
 90                  95                 100                 105

GAG ATG ATC TTT AAC CTC CTT CTG GAA GAA AAA AGA ATT TTG ATC CAG   387
Glu Met Ile Phe Asn Leu Leu Leu Glu Glu Lys Arg Ile Leu Ile Gln
                110                 115                 120

GCT CAG AGG GCC CAA TTG GAA CAA GGA GAG CCA GTT CTC GAA ACA CCT   435
Ala Gln Arg Ala Gln Leu Glu Gln Gly Glu Pro Val Leu Glu Thr Pro
            125                 130                 135

GTG GAG AGC CAG CAA CAT GAG ATT GAA TCC CGG ATC CTG GAT TTA AGG   483
Val Glu Ser Gln Gln His Glu Ile Glu Ser Arg Ile Leu Asp Leu Arg
        140                 145                 150

GCT ATG ATG GAG AAG CTG GTA AAA TCC ATC AGC CAA CTG AAA GAC CAG   531
Ala Met Met Glu Lys Leu Val Lys Ser Ile Ser Gln Leu Lys Asp Gln
    155                 160                 165

CAG GAT GTC TTC TGC TTC CGA TAT AAG ATC CAG GCC AAA GGG AAG ACA   579
Gln Asp Val Phe Cys Phe Arg Tyr Lys Ile Gln Ala Lys Gly Lys Thr
170                 175                 180                 185

CCC TCT CTG GAC CCC CAT CAG ACC AAA GAG CAG AAG ATT CTG CAG GAA   627
Pro Ser Leu Asp Pro His Gln Thr Lys Glu Gln Lys Ile Leu Gln Glu
                190                 195                 200

ACT CTC AAT GAA CTG GAC AAA AGG AGA AAG GAG GTG CTG GAT GCC TCC   675
Thr Leu Asn Glu Leu Asp Lys Arg Arg Lys Glu Val Leu Asp Ala Ser
            205                 210                 215

AAA GCA CTG CTA GGC CGA TTA ACT ACC CTA ATC GAG CTA CTG CTG CCA   723
Lys Ala Leu Leu Gly Arg Leu Thr Thr Leu Ile Glu Leu Leu Leu Pro
        220                 225                 230

AAG TTG GAG GAG TGG AAG GCC CAG CAG CAA AAA GCC TGC ATC AGA GCT   771
```

-continued

Lys Leu Glu Glu Trp Lys Ala Gln Gln Gln Lys Ala Cys Ile Arg Ala
235 240 245

CCC ATT GAC CAC GGG TTG GAA CAG CTG GAG ACA TGG TTC ACA GCT GGA 819
Pro Ile Asp His Gly Leu Glu Gln Leu Glu Thr Trp Phe Thr Ala Gly
250 255 260 265

GCA AAG CTG TTG TTT CAC CTG AGG CAG CTG CTG AAG GAG CTG AAG GGA 867
Ala Lys Leu Leu Phe His Leu Arg Gln Leu Leu Lys Glu Leu Lys Gly
270 275 280

CTG AGT TGC CTG GTT AGC TAT CAG GAT GAC CCT CTG ACC AAA GGG GTG 915
Leu Ser Cys Leu Val Ser Tyr Gln Asp Asp Pro Leu Thr Lys Gly Val
285 290 295

GAC CTA CGC AAC GCC CAG GTC ACA GAG TTG CTA CAG CGT CTG CTC CAC 963
Asp Leu Arg Asn Ala Gln Val Thr Glu Leu Leu Gln Arg Leu Leu His
300 305 310

AGA GCC TTT GTG GTA GAA ACC CAG CCC TGC ATG CCC CAA ACT CCC CAT 1011
Arg Ala Phe Val Val Glu Thr Gln Pro Cys Met Pro Gln Thr Pro His
315 320 325

CGA CCC CTC ATC CTC AAG ACT GGC AGC AAG TTC ACC GTC CGA ACA AGG 1059
Arg Pro Leu Ile Leu Lys Thr Gly Ser Lys Phe Thr Val Arg Thr Arg
330 335 340 345

CTG CTG GTG AGA CTC CAG GAA GGC AAT GAG TCA CTG ACT GTG GAA GTC 1107
Leu Leu Val Arg Leu Gln Glu Gly Asn Glu Ser Leu Thr Val Glu Val
350 355 360

TCC ATT GAC AGG AAT CCT CCT CAA TTA CAA GGC TTC CGG AAG TTC AAC 1155
Ser Ile Asp Arg Asn Pro Pro Gln Leu Gln Gly Phe Arg Lys Phe Asn
365 370 375

ATT CTG ACT TCA AAC CAG AAA ACT TTG ACC CCC GAG AAG GGG CAG AGT 1203
Ile Leu Thr Ser Asn Gln Lys Thr Leu Thr Pro Glu Lys Gly Gln Ser
380 385 390

CAG GGT TTG ATT TGG GAC TTT GGT TAC CTG ACT CTG GTG GAG CAA CGT 1251
Gln Gly Leu Ile Trp Asp Phe Gly Tyr Leu Thr Leu Val Glu Gln Arg
395 400 405

TCA GGT GGT TCA GGA AAG GGC AGC AAT AAG GGG CCA CTA GGT GTG ACA 1299
Ser Gly Gly Ser Gly Lys Gly Ser Asn Lys Gly Pro Leu Gly Val Thr
410 415 420 425

GAG GAA CTG CAC ATC ATC AGC TTC ACG GTC AAA TAT ACC TAC CAG GGT 1347
Glu Glu Leu His Ile Ile Ser Phe Thr Val Lys Tyr Thr Tyr Gln Gly
430 435 440

CTG AAG CAG GAG CTG AAA ACG GAC ACC CTC CCT GTG GTG ATT ATT TCC 1395
Leu Lys Gln Glu Leu Lys Thr Asp Thr Leu Pro Val Val Ile Ile Ser
445 450 455

AAC ATG AAC CAG CTC TCA ATT GCC TGG GCT TCA GTT CTC TGG TTC AAT 1443
Asn Met Asn Gln Leu Ser Ile Ala Trp Ala Ser Val Leu Trp Phe Asn
460 465 470

TTG CTC AGC CCA AAC CTT CAG AAC CAG CAG TTC TTC TCC AAC CCC CCC 1491
Leu Leu Ser Pro Asn Leu Gln Asn Gln Gln Phe Phe Ser Asn Pro Pro
475 480 485

AAG GCC CCC TGG AGC TTG CTG GGC CCT GCT CTC AGT TGG CAG TTC TCC 1539
Lys Ala Pro Trp Ser Leu Leu Gly Pro Ala Leu Ser Trp Gln Phe Ser
490 495 500 505

TCC TAT GTT GGC CGA GGC CTC AAC TCA GAC CAG CTG AGC ATG CTG AGA 1587
Ser Tyr Val Gly Arg Gly Leu Asn Ser Asp Gln Leu Ser Met Leu Arg
510 515 520

AAC AAG CTG TTC GGG CAG AAC TGT AGG ACT GAG GAT CCA TTA TTG TCC 1635
Asn Lys Leu Phe Gly Gln Asn Cys Arg Thr Glu Asp Pro Leu Leu Ser
525 530 535

TGG GCT GAC TTC ACT AAG CGA GAG AGC CCT CCT GGC AAG TTA CCA TTC 1683
Trp Ala Asp Phe Thr Lys Arg Glu Ser Pro Pro Gly Lys Leu Pro Phe
540 545 550

TGG ACA TGG CTG GAC AAA ATT CTG GAG TTG GTA CAT GAC CAC CTG AAG 1731

-continued

```
Trp Thr Trp Leu Asp Lys Ile Leu Glu Leu Val His Asp His Leu Lys
    555                 560                 565

GAT CTC TGG AAT GAT GGA CGC ATC ATG GGC TTT GTG AGT CGG AGC CAG    1779
Asp Leu Trp Asn Asp Gly Arg Ile Met Gly Phe Val Ser Arg Ser Gln
570                 575                 580                 585

GAG CGC CGG CTG CTG AAG AAG ACC ATG TCT GGC ACC TTT CTA CTG CGC    1827
Glu Arg Arg Leu Leu Lys Lys Thr Met Ser Gly Thr Phe Leu Leu Arg
                590                 595                 600

TTC AGT GAA TCG TCA GAA GGG GGC ATT ACC TGC TCC TGG GTG GAG CAC    1875
Phe Ser Glu Ser Ser Glu Gly Gly Ile Thr Cys Ser Trp Val Glu His
            605                 610                 615

CAG GAT GAT GAC AAG GTG CTC ATC TAC TCT GTG CAA CCG TAC ACG AAG    1923
Gln Asp Asp Asp Lys Val Leu Ile Tyr Ser Val Gln Pro Tyr Thr Lys
        620                 625                 630

GAG GTG CTG CAG TCA CTC CCG CTG ACT GAA ATC ATC CGC CAT TAC CAG    1971
Glu Val Leu Gln Ser Leu Pro Leu Thr Glu Ile Ile Arg His Tyr Gln
    635                 640                 645

TTG CTC ACT GAG GAG AAT ATA CCT GAA AAC CCA CTG CGC TTC CTC TAT    2019
Leu Leu Thr Glu Glu Asn Ile Pro Glu Asn Pro Leu Arg Phe Leu Tyr
650                 655                 660                 665

CCC CGA ATC CCC CGG GAT GAA GCT TTT GGG TGC TAC TAC CAG GAG AAA    2067
Pro Arg Ile Pro Arg Asp Glu Ala Phe Gly Cys Tyr Tyr Gln Glu Lys
                670                 675                 680

GTT AAT CTC CAG GAA CGG AGG AAA TAC CTG AAA CAC AGG CTC ATT GTG    2115
Val Asn Leu Gln Glu Arg Arg Lys Tyr Leu Lys His Arg Leu Ile Val
            685                 690                 695

GTC TCT AAT AGA CAG GTG GAT GAA CTG CAA CAA CCG CTG GAG CTT AAG    2163
Val Ser Asn Arg Gln Val Asp Glu Leu Gln Gln Pro Leu Glu Leu Lys
        700                 705                 710

CCA GAG CCA GAG CTG GAG TCA TTA GAG CTG GAA CTA GGG CTG GTG CCA    2211
Pro Glu Pro Glu Leu Glu Ser Leu Glu Leu Glu Leu Gly Leu Val Pro
    715                 720                 725

GAG CCA GAG CTC AGC CTG GAC TTA GAG CCA CTG CTG AAG GCA GGG CTG    2259
Glu Pro Glu Leu Ser Leu Asp Leu Glu Pro Leu Leu Lys Ala Gly Leu
730                 735                 740                 745

GAT CTG GGG CCA GAG CTA GAG TCT GTG CTG GAG TCC ACT CTG GAG CCT    2307
Asp Leu Gly Pro Glu Leu Glu Ser Val Leu Glu Ser Thr Leu Glu Pro
                750                 755                 760

GTG ATA GAG CCC ACA CTA TGC ATG GTA TCA CAA ACA GTG CCA GAG CCA    2355
Val Ile Glu Pro Thr Leu Cys Met Val Ser Gln Thr Val Pro Glu Pro
            765                 770                 775

GAC CAA GGA CCT GTA TCA CAG CCA GTG CCA GAG CCA GAT TTG CCC TGT    2403
Asp Gln Gly Pro Val Ser Gln Pro Val Pro Glu Pro Asp Leu Pro Cys
        780                 785                 790

GAT CTG AGA CAT TTG AAC ACT GAG CCA ATG GAA ATC TTC AGA AAC TGT    2451
Asp Leu Arg His Leu Asn Thr Glu Pro Met Glu Ile Phe Arg Asn Cys
    795                 800                 805

GTA AAG ATT GAA GAA ATC ATG CCG AAT GGT GAC CCA CTG TTG GCT GGC    2499
Val Lys Ile Glu Glu Ile Met Pro Asn Gly Asp Pro Leu Leu Ala Gly
810                 815                 820                 825

CAG AAC ACC GTG GAT GAG GTT TAC GTC TCC CGC CCC AGC CAC TTC TAC    2547
Gln Asn Thr Val Asp Glu Val Tyr Val Ser Arg Pro Ser His Phe Tyr
                830                 835                 840

ACT GAT GGA CCC TTG ATG CCT TCT GAC TTC TAGGAACCAC ATTTCCTCTG      2597
Thr Asp Gly Pro Leu Met Pro Ser Asp Phe
            845                 850

TTCTTTTCAT ATCTCTTTGC CCTTCCTACT CCTCATAGCA TGATATTGTT CTCCAAGG    2657

GGGAATCAGG CATGTGTCCC TTCCAAGCTG TGTTAACTGT TCAAACTCAG GCCTGTGT    2717

CTCCATTGGG GTGAGAGGTG AAAGCATAAC ATGGGTACAG AGGGGACAAC AATGAATC    2777
```

AACAGATGCT GAGCCATAGG TCTAAATAGG ATCCTGGAGG CTGCCTGCTG TGCTGGGA 2837

TATAGGGGTC CTGGGGGCAG GCCAGGGCAG TTGACAGGTA CTTGGAGGGC TCAGGGCA 2897

GGCTTCTTTC CAGTATGGAA GGATTTCAAC ATTTTAATAG TTGGTTAGGC TAAACTGG 2957

CATACTGGCA TTGGCCTTGG TGGGGAGCAC AGACACAGGA TAGGACTCCA TTTCTTTC 3017

CCATTCCTTC ATGTCTAGGA TAACTTGCTT TCTTCTTTCC TTTACTCCTG GCTCAAGC 3077

TGAATTTCTT CTTTTCCTGC AGGGGTTGAG AGCTTTCTGC CTTAGCCTAC CATGTGAA 3137

TCTACCCTGA AGAAAGGGAT GGATAGGAAG TAGACCTCTT TTTCTTACCA GTCTCCTC 3197

CTACTCTGCC CCCTAAGCTG GCTGTACCTG TTCCTCCCCC ATAAAATGAT CCTGCCAA 3257

TAAAAAAAAA A 3268

( 2 ) INFORMATION FOR SEQ ID NO:2:

( i ) SEQUENCE CHARACTERISTICS:
( A ) LENGTH: 851 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Ala Gln Trp Glu Met Leu Gln Asn Leu Asp Ser Pro Phe Gln Asp
1 5 10 15

Gln Leu His Gln Leu Tyr Ser His Ser Leu Leu Pro Val Asp Ile Arg
20 25 30

Gln Tyr Leu Ala Val Trp Ile Glu Asp Gln Asn Trp Gln Glu Ala Ala
35 40 45

Leu Gly Ser Asp Asp Ser Lys Ala Thr Met Leu Phe Phe His Phe Leu
50 55 60

Asp Gln Leu Asn Tyr Glu Cys Gly Arg Cys Ser Gln Asp Pro Glu Ser
65 70 75 80

Leu Leu Leu Gln His Asn Leu Arg Lys Phe Cys Arg Asp Ile Gln Pro
85 90 95

Phe Ser Gln Asp Pro Thr Gln Leu Ala Glu Met Ile Phe Asn Leu Leu
100 105 110

Leu Glu Glu Lys Arg Ile Leu Ile Gln Ala Gln Arg Ala Gln Leu Glu
115 120 125

Gln Gly Glu Pro Val Leu Glu Thr Pro Val Glu Ser Gln Gln His Glu
130 135 140

Ile Glu Ser Arg Ile Leu Asp Leu Arg Ala Met Met Glu Lys Leu Val
145 150 155 160

Lys Ser Ile Ser Gln Leu Lys Asp Gln Gln Asp Val Phe Cys Phe Arg
165 170 175

Tyr Lys Ile Gln Ala Lys Gly Lys Thr Pro Ser Leu Asp Pro His Gln
180 185 190

Thr Lys Glu Gln Lys Ile Leu Gln Glu Thr Leu Asn Glu Leu Asp Lys
195 200 205

Arg Arg Lys Glu Val Leu Asp Ala Ser Lys Ala Leu Leu Gly Arg Leu
210 215 220

Thr Thr Leu Ile Glu Leu Leu Leu Pro Lys Leu Glu Glu Trp Lys Ala
225 230 235 240

Gln Gln Gln Lys Ala Cys Ile Arg Ala Pro Ile Asp His Gly Leu Glu
245 250 255

Gln Leu Glu Thr Trp Phe Thr Ala Gly Ala Lys Leu Leu Phe His Leu

-continued 260 265 270

Arg Gln Leu Leu Lys Glu Leu Lys Gly Leu Ser Cys Leu Val Ser Tyr
275 280 285

Gln Asp Asp Pro Leu Thr Lys Gly Val Asp Leu Arg Asn Ala Gln Val
290 295 300

Thr Glu Leu Leu Gln Arg Leu Leu His Arg Ala Phe Val Val Glu Thr
305 310 315 320

Gln Pro Cys Met Pro Gln Thr Pro His Arg Pro Leu Ile Leu Lys Thr
325 330 335

Gly Ser Lys Phe Thr Val Arg Thr Arg Leu Leu Val Arg Leu Gln Glu
340 345 350

Gly Asn Glu Ser Leu Thr Val Glu Val Ser Ile Asp Arg Asn Pro Pro
355 360 365

Gln Leu Gln Gly Phe Arg Lys Phe Asn Ile Leu Thr Ser Asn Gln Lys
370 375 380

Thr Leu Thr Pro Glu Lys Gly Gln Ser Gln Gly Leu Ile Trp Asp Phe
385 390 395 400

Gly Tyr Leu Thr Leu Val Glu Gln Arg Ser Gly Gly Ser Gly Lys Gly
405 410 415

Ser Asn Lys Gly Pro Leu Gly Val Thr Glu Glu Leu His Ile Ile Ser
420 425 430

Phe Thr Val Lys Tyr Thr Tyr Gln Gly Leu Lys Gln Glu Leu Lys Thr
435 440 445

Asp Thr Leu Pro Val Val Ile Ile Ser Asn Met Asn Gln Leu Ser Ile
450 455 460

Ala Trp Ala Ser Val Leu Trp Phe Asn Leu Leu Ser Pro Asn Leu Gln
465 470 475 480

Asn Gln Gln Phe Phe Ser Asn Pro Pro Lys Ala Pro Trp Ser Leu Leu
485 490 495

Gly Pro Ala Leu Ser Trp Gln Phe Ser Ser Tyr Val Gly Arg Gly Leu
500 505 510

Asn Ser Asp Gln Leu Ser Met Leu Arg Asn Lys Leu Phe Gly Gln Asn
515 520 525

Cys Arg Thr Glu Asp Pro Leu Leu Ser Trp Ala Asp Phe Thr Lys Arg
530 535 540

Glu Ser Pro Pro Gly Lys Leu Pro Phe Trp Thr Trp Leu Asp Lys Ile
545 550 555 560

Leu Glu Leu Val His Asp His Leu Lys Asp Leu Trp Asn Asp Gly Arg
565 570 575

Ile Met Gly Phe Val Ser Arg Ser Gln Glu Arg Arg Leu Leu Lys Lys
580 585 590

Thr Met Ser Gly Thr Phe Leu Leu Arg Phe Ser Glu Ser Ser Glu Gly
595 600 605

Gly Ile Thr Cys Ser Trp Val Glu His Gln Asp Asp Asp Lys Val Leu
610 615 620

Ile Tyr Ser Val Gln Pro Tyr Thr Lys Glu Val Leu Gln Ser Leu Pro
625 630 635 640

Leu Thr Glu Ile Ile Arg His Tyr Gln Leu Leu Thr Glu Glu Asn Ile
645 650 655

Pro Glu Asn Pro Leu Arg Phe Leu Tyr Pro Arg Ile Pro Arg Asp Glu
660 665 670

Ala Phe Gly Cys Tyr Tyr Gln Glu Lys Val Asn Leu Gln Glu Arg Arg
675 680 685

-continued

```
Lys Tyr Leu Lys His Arg Leu Ile Val Val Ser Asn Arg Gln Val Asp
    690                 695                     700

Glu Leu Gln Gln Pro Leu Glu Leu Lys Pro Glu Pro Glu Leu Glu Ser
705                 710                     715                 720

Leu Glu Leu Glu Leu Gly Leu Val Pro Glu Pro Glu Leu Ser Leu Asp
                725                     730                 735

Leu Glu Pro Leu Leu Lys Ala Gly Leu Asp Leu Gly Pro Glu Leu Glu
            740                     745                 750

Ser Val Leu Glu Ser Thr Leu Glu Pro Val Ile Glu Pro Thr Leu Cys
        755                     760                 765

Met Val Ser Gln Thr Val Pro Glu Pro Asp Gln Gly Pro Val Ser Gln
    770                 775                     780

Pro Val Pro Glu Pro Asp Leu Pro Cys Asp Leu Arg His Leu Asn Thr
785                 790                     795                 800

Glu Pro Met Glu Ile Phe Arg Asn Cys Val Lys Ile Glu Glu Ile Met
                805                     810                 815

Pro Asn Gly Asp Pro Leu Leu Ala Gly Gln Asn Thr Val Asp Glu Val
            820                     825                 830

Tyr Val Ser Arg Pro Ser His Phe Tyr Thr Asp Gly Pro Leu Met Pro
        835                     840                 845

Ser Asp Phe
    850
```

( 2 ) INFORMATION FOR SEQ ID NO:3:

( i ) SEQUENCE CHARACTERISTICS:
( A ) LENGTH: 3943 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens ( v i i ) IMMEDIATE SOURCE:
( B ) CLONE: Human Stat91

( i x ) FEATURE:
( A ) NAME/KEY: CDS
( B ) LOCATION: 197..2449

( x i ) SEQUENCE DESCRIPTION: SEQ ID NO:3:

```
ATTAAACCTC TCGCCGAGCC CCTCCGCAGA CTCTGCGCCG GAAAGTTTCA TTTGCTGTAT     60

GCCATCCTCG AGAGCTGTCT AGGTTAACGT TCGCACTCTG TGTATATAAC CTCGACAGT     120

TTGGCACCTA ACGTGCTGTG CGTAGCTGCT CCTTTGGTTG AATCCCCAGG CCCTTGTTG     180

GGCACAAGGT GGCAGG ATG TCT CAG TGG TAC GAA CTT CAG CAG CTT GAC        229
                  Met Ser Gln Trp Tyr Glu Leu Gln Gln Leu Asp
                   1               5                  10

TCA AAA TTC CTG GAG CAG GTT CAC CAG CTT TAT GAT GAC AGT TTT CCC      277
Ser Lys Phe Leu Glu Gln Val His Gln Leu Tyr Asp Asp Ser Phe Pro
            15                  20                  25

ATG GAA ATC AGA CAG TAC CTG GCA CAG TGG TTA GAA AAG CAA GAC TGG      325
Met Glu Ile Arg Gln Tyr Leu Ala Gln Trp Leu Glu Lys Gln Asp Trp
        30                  35                  40

GAG CAC GCT GCC AAT GAT GTT TCA TTT GCC ACC ATC CGT TTT CAT GAC      373
Glu His Ala Ala Asn Asp Val Ser Phe Ala Thr Ile Arg Phe His Asp
```

-continued

```
    45                  50                  55

CTC CTG TCA CAG CTG GAT GAT CAA TAT AGT CGC TTT TCT TTG GAG AAT     421
Leu Leu Ser Gln Leu Asp Asp Gln Tyr Ser Arg Phe Ser Leu Glu Asn
60                  65                  70                  75

AAC TTC TTG CTA CAG CAT AAC ATA AGG AAA AGC AAG CGT AAT CTT CAG     469
Asn Phe Leu Leu Gln His Asn Ile Arg Lys Ser Lys Arg Asn Leu Gln
                80                  85                  90

GAT AAT TTT CAG GAA GAC CCA ATC CAG ATG TCT ATG ATC ATT TAC AGC     517
Asp Asn Phe Gln Glu Asp Pro Ile Gln Met Ser Met Ile Ile Tyr Ser
            95                  100                 105

TGT CTG AAG GAA GAA AGG AAA ATT CTG GAA AAC GCC CAG AGA TTT AAT     565
Cys Leu Lys Glu Glu Arg Lys Ile Leu Glu Asn Ala Gln Arg Phe Asn
        110                 115                 120

CAG GCT CAG TCG GGG AAT ATT CAG AGC ACA GTG ATG TTA GAC AAA CAG     613
Gln Ala Gln Ser Gly Asn Ile Gln Ser Thr Val Met Leu Asp Lys Gln
    125                 130                 135

AAA GAG CTT GAC AGT AAA GTC AGA AAT GTG AAG GAC AAG GTT ATG TGT     661
Lys Glu Leu Asp Ser Lys Val Arg Asn Val Lys Asp Lys Val Met Cys
140                 145                 150                 155

ATA GAG CAT GAA ATC AAG AGC CTG GAA GAT TTA CAA GAT GAA TAT GAC     709
Ile Glu His Glu Ile Lys Ser Leu Glu Asp Leu Gln Asp Glu Tyr Asp
                160                 165                 170

TTC AAA TGC AAA ACC TTG CAG AAC AGA GAA CAC GAG ACC AAT GGT GTG     757
Phe Lys Cys Lys Thr Leu Gln Asn Arg Glu His Glu Thr Asn Gly Val
            175                 180                 185

GCA AAG AGT GAT CAG AAA CAA GAA CAG CTG TTA CTC AAG AAG ATG TAT     805
Ala Lys Ser Asp Gln Lys Gln Glu Gln Leu Leu Leu Lys Lys Met Tyr
        190                 195                 200

TTA ATG CTT GAC AAT AAG AGA AAG GAA GTA GTT CAC AAA ATA ATA GAG     853
Leu Met Leu Asp Asn Lys Arg Lys Glu Val Val His Lys Ile Ile Glu
    205                 210                 215

TTG CTG AAT GTC ACT GAA CTT ACC CAG AAT GCC CTG ATT AAT GAT GAA     901
Leu Leu Asn Val Thr Glu Leu Thr Gln Asn Ala Leu Ile Asn Asp Glu
220                 225                 230                 235

CTA GTG GAG TGG AAG CGG AGA CAG CAG AGC GCC TGT ATT GGG GGG CCG     949
Leu Val Glu Trp Lys Arg Arg Gln Gln Ser Ala Cys Ile Gly Gly Pro
                240                 245                 250

CCC AAT GCT TGC TTG GAT CAG CTG CAG AAC TGG TTC ACT ATA GTT GCG     997
Pro Asn Ala Cys Leu Asp Gln Leu Gln Asn Trp Phe Thr Ile Val Ala
            255                 260                 265

GAG AGT CTG CAG CAA GTT CGG CAG CAG CTT AAA AAG TTG GAG GAA TTG    1045
Glu Ser Leu Gln Gln Val Arg Gln Gln Leu Lys Lys Leu Glu Glu Leu
        270                 275                 280

GAA CAG AAA TAC ACC TAC GAA CAT GAC CCT ATC ACA AAA AAC AAA CAA    1093
Glu Gln Lys Tyr Thr Tyr Glu His Asp Pro Ile Thr Lys Asn Lys Gln
    285                 290                 295

GTG TTA TGG GAC CGC ACC TTC AGT CTT TTC CAG CAG CTC ATT CAG AGC    1141
Val Leu Trp Asp Arg Thr Phe Ser Leu Phe Gln Gln Leu Ile Gln Ser
300                 305                 310                 315

TCG TTT GTG GTG GAA AGA CAG CCC TGC ATG CCA ACG CAC CCT CAG AGG    1189
Ser Phe Val Val Glu Arg Gln Pro Cys Met Pro Thr His Pro Gln Arg
                320                 325                 330

CCG CTG GTC TTG AAG ACA GGG GTC CAG TTC ACT GTG AAG TTG AGA CTG    1237
Pro Leu Val Leu Lys Thr Gly Val Gln Phe Thr Val Lys Leu Arg Leu
            335                 340                 345

TTG GTG AAA TTG CAA GAG CTG AAT TAT AAT TTG AAA GTC AAA GTC TTA    1285
Leu Val Lys Leu Gln Glu Leu Asn Tyr Asn Leu Lys Val Lys Val Leu
        350                 355                 360

TTT GAT AAA GAT GTG AAT GAG AGA AAT ACA GTA AAA GGA TTT AGG AAG    1333
Phe Asp Lys Asp Val Asn Glu Arg Asn Thr Val Lys Gly Phe Arg Lys
```

-continued

```
    365                 370                 375

TTC AAC ATT TTG GGC ACG CAC ACA AAA GTG ATG AAC ATG GAG GAG TCC      1381
Phe Asn Ile Leu Gly Thr His Thr Lys Val Met Asn Met Glu Glu Ser
380                 385                 390                 395

ACC AAT GGC AGT CTG GCG GCT GAA TTT CGG CAC CTG CAA TTG AAA GAA      1429
Thr Asn Gly Ser Leu Ala Ala Glu Phe Arg His Leu Gln Leu Lys Glu
                400                 405                 410

CAG AAA AAT GCT GGC ACC AGA ACG AAT GAG GGT CCT CTC ATC GTT ACT      1477
Gln Lys Asn Ala Gly Thr Arg Thr Asn Glu Gly Pro Leu Ile Val Thr
            415                 420                 425

GAA GAG CTT CAC TCC CTT AGT TTT GAA ACC CAA TTG TGC CAG CCT GGT      1525
Glu Glu Leu His Ser Leu Ser Phe Glu Thr Gln Leu Cys Gln Pro Gly
        430                 435                 440

TTG GTA ATT GAC CTC GAG ACG ACC TCT CTG CCC GTT GTG GTG ATC TCC      1573
Leu Val Ile Asp Leu Glu Thr Thr Ser Leu Pro Val Val Val Ile Ser
    445                 450                 455

AAC GTC AGC CAG CTC CCG AGC GGT TGG GCC TCC ATC CTT TGG TAC AAC      1621
Asn Val Ser Gln Leu Pro Ser Gly Trp Ala Ser Ile Leu Trp Tyr Asn
460                 465                 470                 475

ATG CTG GTG GCG GAA CCC AGG AAT CTG TCC TTC TTC CTG ACT CCA CCA      1669
Met Leu Val Ala Glu Pro Arg Asn Leu Ser Phe Phe Leu Thr Pro Pro
                480                 485                 490

TGT GCA CGA TGG GCT CAG CTT TCA GAA GTG CTG AGT TGG CAG TTT TCT      1717
Cys Ala Arg Trp Ala Gln Leu Ser Glu Val Leu Ser Trp Gln Phe Ser
            495                 500                 505

TCT GTC ACC AAA AGA GGT CTC AAT GTG GAC CAG CTG AAC ATG TTG GGA      1765
Ser Val Thr Lys Arg Gly Leu Asn Val Asp Gln Leu Asn Met Leu Gly
        510                 515                 520

GAG AAG CTT CTT GGT CCT AAC GCC AGC CCC GAT GGT CTC ATT CCG TGG      1813
Glu Lys Leu Leu Gly Pro Asn Ala Ser Pro Asp Gly Leu Ile Pro Trp
    525                 530                 535

ACG AGG TTT TGT AAG GAA AAT ATA AAT GAT AAA AAT TTT CCC TTC TGG      1861
Thr Arg Phe Cys Lys Glu Asn Ile Asn Asp Lys Asn Phe Pro Phe Trp
540                 545                 550                 555

CTT TGG ATT GAA AGC ATC CTA GAA CTC ATT AAA AAA CAC CTG CTC CCT      1909
Leu Trp Ile Glu Ser Ile Leu Glu Leu Ile Lys Lys His Leu Leu Pro
                560                 565                 570

CTC TGG AAT GAT GGG TGC ATC ATG GGC TTC ATC AGC AAG GAG CGA GAG      1957
Leu Trp Asn Asp Gly Cys Ile Met Gly Phe Ile Ser Lys Glu Arg Glu
            575                 580                 585

CGT GCC CTG TTG AAG GAC CAG CAG CCG GGG ACC TTC CTG CTG CGG TTC      2005
Arg Ala Leu Leu Lys Asp Gln Gln Pro Gly Thr Phe Leu Leu Arg Phe
        590                 595                 600

AGT GAG AGC TCC CGG GAA GGG GCC ATC ACA TTC ACA TGG GTG GAG CGG      2053
Ser Glu Ser Ser Arg Glu Gly Ala Ile Thr Phe Thr Trp Val Glu Arg
    605                 610                 615

TCC CAG AAC GGA GGC GAA CCT GAC TTC CAT GCG GTT GAA CCC TAC ACG      2101
Ser Gln Asn Gly Gly Glu Pro Asp Phe His Ala Val Glu Pro Tyr Thr
620                 625                 630                 635

AAG AAA GAA CTT TCT GCT GTT ACT TTC CCT GAC ATC ATT CGC AAT TAC      2149
Lys Lys Glu Leu Ser Ala Val Thr Phe Pro Asp Ile Ile Arg Asn Tyr
                640                 645                 650

AAA GTC ATG GCT GCT GAG AAT ATT CCT GAG AAT CCC CTG AAG TAT CTG      2197
Lys Val Met Ala Ala Glu Asn Ile Pro Glu Asn Pro Leu Lys Tyr Leu
            655                 660                 665

TAT CCA AAT ATT GAC AAA GAC CAT GCC TTT GGA AAG TAT TAC TCC AGG      2245
Tyr Pro Asn Ile Asp Lys Asp His Ala Phe Gly Lys Tyr Tyr Ser Arg
        670                 675                 680

CCA AAG GAA GCA CCA GAG CCA ATG GAA CTT GAT GGC CCT AAA GGA ACT      2293
Pro Lys Glu Ala Pro Glu Pro Met Glu Leu Asp Gly Pro Lys Gly Thr
```

-continued

```
     685                         690                         695

GGA  TAT  ATC  AAG  ACT  GAG  TTG  ATT  TCT  GTG  TCT  GAA  GTT  CAC  CCT  TCT        2341
Gly  Tyr  Ile  Lys  Thr  Glu  Leu  Ile  Ser  Val  Ser  Glu  Val  His  Pro  Ser
700                      705                      710                      715

AGA  CTT  CAG  ACC  ACA  GAC  AAC  CTG  CTC  CCC  ATG  TCT  CCT  GAG  GAG  TTT        2389
Arg  Leu  Gln  Thr  Thr  Asp  Asn  Leu  Leu  Pro  Met  Ser  Pro  Glu  Glu  Phe
                    720                      725                      730

GAC  GAG  GTG  TCT  CGG  ATA  GTG  GGC  TCT  GTA  GAA  TTC  GAC  AGT  ATG  ATG        2437
Asp  Glu  Val  Ser  Arg  Ile  Val  Gly  Ser  Val  Glu  Phe  Asp  Ser  Met  Met
               735                      740                      745

AAC  ACA  GTA  TAGAGCATGA  ATTTTTTTCA  TCTTCTCTGG  CGACAGTTTT                       2486
Asn  Thr  Val
          750

CCTTCTCATC  TGTGATTCCC  TCCTGCTACT  CTGTTCCTTC  ACATCCTGTG  TTTCTAGG              2546

AATGAAAGAA  AGGCCAGCAA  ATTCGCTGCA  ACCTGTTGAT  AGCAAGTGAA  TTTTTCTC              2606

ACTCAGAAAC  ATCAGTTACT  CTGAAGGGCA  TCATGCATCT  TACTGAAGGT  AAAATTGA              2666

GGCATTCTCT  GAAGAGTGGG  TTTCACAAGT  GAAAAACATC  CAGATACACC  CAAAGTAT              2726

GGACGAGAAT  GAGGGTCCTT  TGGGAAAGGA  GAAGTTAAGC  AACATCTAGC  AAATGTTA              2786

CATAAAGTCA  GTGCCCAACT  GTTATAGGTT  GTTGGATAAA  TCAGTGGTTA  TTTAGGGA              2846

TGCTTGACGT  AGGAACGGTA  AATTTCTGTG  GGAGAATTCT  TACATGTTTT  CTTTGCTT              2906

AGTGTAACTG  GCAGTTTTCC  ATTGGTTTAC  CTGTGAAATA  GTTCAAAGCC  AAGTTTAT              2966

ACAATTATAT  CAGTCCTCTT  TCAAAGGTAG  CCATCATGGA  TCTGGTAGGG  GGAAAATG              3026

TATTTTATTA  CATCTTTCAC  ATTGGCTATT  TAAAGACAAA  GACAAATTCT  GTTTCTTG              3086

AAGAGAACAT  TTCCAAATTC  ACAAGTTGTG  TTTGATATCC  AAAGCTGAAT  ACATTCTG              3146

TTCATCTTGG  TCACATACAA  TTATTTTTAC  AGTTCTCCCA  AGGGAGTTAG  GCTATTCA              3206

ACCACTCATT  CAAAAGTTGA  AATTAACCAT  AGATGTAGAT  AAACTCAGAA  ATTTAATT              3266

TGTTTCTTAA  ATGGGCTACT  TTGTCCTTTT  TGTTATTAGG  GTGGTATTTA  GTCTATTA              3326

CACAAAATTG  GGAAAGGAGT  AGAAAAAGCA  GTAACTGACA  ACTTGAATAA  TACACCAG              3386

ATAATATGAG  AATCAGATCA  TTTCAAAACT  CATTTCCTAT  GTAACTGCAT  TGAGAACT              3446

ATATGTTTCG  CTGATATATG  TGTTTTTCAC  ATTTGCGAAT  GGTTCCATTC  TCTCTCCT              3506

ACTTTTTCCA  GACACTTTTT  TGAGTGGATG  ATGTTTCGTG  AAGTATACTG  TATTTTTA              3566

TTTTTCCTTC  CTTATCACTG  ACACAAAAAG  TAGATTAAGA  GATGGGTTTG  ACAAGGTT              3626

TCCCTTTTAC  ATACTGCTGT  CTATGTGGCT  GTATCTTGTT  TTTCCACTAC  TGCTACCA              3686

ACTATATTAT  CATGCAAATG  CTGTATTCTT  CTTTGGTGGA  GATAAAGATT  TCTTGAGT              3746

TGTTTTAAAA  TTAAAGCTAA  AGTATCTGTA  TTGCATTAAA  TATAATATCG  ACACAGTG              3806

TTCCGTGGCA  CTGCATACAA  TCTGAGGCCT  CCTCTCTCAG  TTTTTATATA  GATGGCGA              3866

ACCTAAGTTT  CAGTTGATTT  TACAATTGAA  ATGACTAAAA  AACAAAGAAG  ACAACATT              3926

AAACAATATT  GTTTCTA                                                             3943
```

NFORMATION FOR SEQ ID NO:4:

( i ) SEQUENCE CHARACTERISTICS:

( A ) LENGTH: 750 amino acids ( B ) TYPE: amino acid ( D ) TOPOLOGY: linear ( i i ) MOLECULE TYPE: protein ( x i ) SEQUENCE DESCRIPTION: SEQ ID NO:4:

-continued

| | | | | | | | | | | | | | | | |
|---|---|---|---|---|---|---|---|---|---|---|---|---|---|---|---|
| Met | Ser | Gln | Trp | Tyr | Glu | Leu | Gln | Gln | Leu | Asp | Ser | Lys | Phe | Leu | Glu |
| 1 | | | | 5 | | | | | 10 | | | | | 15 | |
| Gln | Val | His | Gln | Leu | Tyr | Asp | Asp | Ser | Phe | Pro | Met | Glu | Ile | Arg | Gln |
| | | | 20 | | | | | 25 | | | | | 30 | | |
| Tyr | Leu | Ala | Gln | Trp | Leu | Glu | Lys | Gln | Asp | Trp | Glu | His | Ala | Ala | Asn |
| | | 35 | | | | | 40 | | | | | 45 | | | |
| Asp | Val | Ser | Phe | Ala | Thr | Ile | Arg | Phe | His | Asp | Leu | Leu | Ser | Gln | Leu |
| | 50 | | | | | 55 | | | | | 60 | | | | |
| Asp | Asp | Gln | Tyr | Ser | Arg | Phe | Ser | Leu | Glu | Asn | Asn | Phe | Leu | Leu | Gln |
| 65 | | | | | 70 | | | | | 75 | | | | | 80 |
| His | Asn | Ile | Arg | Lys | Ser | Lys | Arg | Asn | Leu | Gln | Asp | Asn | Phe | Gln | Glu |
| | | | | 85 | | | | | 90 | | | | | 95 | |
| Asp | Pro | Ile | Gln | Met | Ser | Met | Ile | Ile | Tyr | Ser | Cys | Leu | Lys | Glu | Glu |
| | | | 100 | | | | | 105 | | | | | 110 | | |
| Arg | Lys | Ile | Leu | Glu | Asn | Ala | Gln | Arg | Phe | Asn | Gln | Ala | Gln | Ser | Gly |
| | | 115 | | | | | 120 | | | | | 125 | | | |
| Asn | Ile | Gln | Ser | Thr | Val | Met | Leu | Asp | Lys | Gln | Lys | Glu | Leu | Asp | Ser |
| | 130 | | | | | 135 | | | | | 140 | | | | |
| Lys | Val | Arg | Asn | Val | Lys | Asp | Lys | Val | Met | Cys | Ile | Glu | His | Glu | Ile |
| 145 | | | | | 150 | | | | | 155 | | | | | 160 |
| Lys | Ser | Leu | Glu | Asp | Leu | Gln | Asp | Glu | Tyr | Asp | Phe | Lys | Cys | Lys | Thr |
| | | | | 165 | | | | | 170 | | | | | 175 | |
| Leu | Gln | Asn | Arg | Glu | His | Glu | Thr | Asn | Gly | Val | Ala | Lys | Ser | Asp | Gln |
| | | | 180 | | | | | 185 | | | | | 190 | | |
| Lys | Gln | Glu | Gln | Leu | Leu | Leu | Lys | Lys | Met | Tyr | Leu | Met | Leu | Asp | Asn |
| | | 195 | | | | | 200 | | | | | 205 | | | |
| Lys | Arg | Lys | Glu | Val | Val | His | Lys | Ile | Ile | Glu | Leu | Leu | Asn | Val | Thr |
| | 210 | | | | | 215 | | | | | 220 | | | | |
| Glu | Leu | Thr | Gln | Asn | Ala | Leu | Ile | Asn | Asp | Glu | Leu | Val | Glu | Trp | Lys |
| 225 | | | | | 230 | | | | | 235 | | | | | 240 |
| Arg | Arg | Gln | Gln | Ser | Ala | Cys | Ile | Gly | Gly | Pro | Pro | Asn | Ala | Cys | Leu |
| | | | | 245 | | | | | 250 | | | | | 255 | |
| Asp | Gln | Leu | Gln | Asn | Trp | Phe | Thr | Ile | Val | Ala | Glu | Ser | Leu | Gln | Gln |
| | | | 260 | | | | | 265 | | | | | 270 | | |
| Val | Arg | Gln | Gln | Leu | Lys | Lys | Leu | Glu | Glu | Leu | Glu | Gln | Lys | Tyr | Thr |
| | | 275 | | | | | 280 | | | | | 285 | | | |
| Tyr | Glu | His | Asp | Pro | Ile | Thr | Lys | Asn | Lys | Gln | Val | Leu | Trp | Asp | Arg |
| | 290 | | | | | 295 | | | | | 300 | | | | |
| Thr | Phe | Ser | Leu | Phe | Gln | Gln | Leu | Ile | Gln | Ser | Ser | Phe | Val | Val | Glu |
| 305 | | | | | 310 | | | | | 315 | | | | | 320 |
| Arg | Gln | Pro | Cys | Met | Pro | Thr | His | Pro | Gln | Arg | Pro | Leu | Val | Leu | Lys |
| | | | | 325 | | | | | 330 | | | | | 335 | |
| Thr | Gly | Val | Gln | Phe | Thr | Val | Lys | Leu | Arg | Leu | Leu | Val | Lys | Leu | Gln |
| | | | 340 | | | | | 345 | | | | | 350 | | |
| Glu | Leu | Asn | Tyr | Asn | Leu | Lys | Val | Lys | Val | Leu | Phe | Asp | Lys | Asp | Val |
| | | 355 | | | | | 360 | | | | | 365 | | | |
| Asn | Glu | Arg | Asn | Thr | Val | Lys | Gly | Phe | Arg | Lys | Phe | Asn | Ile | Leu | Gly |
| | 370 | | | | | 375 | | | | | 380 | | | | |
| Thr | His | Thr | Lys | Val | Met | Asn | Met | Glu | Glu | Ser | Thr | Asn | Gly | Ser | Leu |
| 385 | | | | | 390 | | | | | 395 | | | | | 400 |
| Ala | Ala | Glu | Phe | Arg | His | Leu | Gln | Leu | Lys | Glu | Gln | Lys | Asn | Ala | Gly |
| | | | | 405 | | | | | 410 | | | | | 415 | |
| Thr | Arg | Thr | Asn | Glu | Gly | Pro | Leu | Ile | Val | Thr | Glu | Glu | Leu | His | Ser |
| | | | 420 | | | | | 425 | | | | | 430 | | |

-continued

```
Leu Ser Phe Glu Thr Gln Leu Cys Gln Pro Gly Leu Val Ile Asp Leu
        435                 440                 445

Glu Thr Thr Ser Leu Pro Val Val Val Ile Ser Asn Val Ser Gln Leu
    450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
        515                 520                 525

Pro Asn Ala Ser Pro Asp Gly Leu Ile Pro Trp Thr Arg Phe Cys Lys
    530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
        595                 600                 605

Glu Gly Ala Ile Thr Phe Thr Trp Val Glu Arg Ser Gln Asn Gly Gly
    610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
        675                 680                 685

Glu Pro Met Glu Leu Asp Gly Pro Lys Gly Thr Gly Tyr Ile Lys Thr
    690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
            740                 745                 750
```

( 2 ) INFORMATION FOR SEQ ID NO:5:

( i ) SEQUENCE CHARACTERISTICS:
( A ) LENGTH: 2607 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens ( i x ) FEATURE:

( A ) NAME/KEY: CDS
( B ) LOCATION: 197..2335

( x i ) SEQUENCE DESCRIPTION: SEQ ID NO:5:

```
ATTAAACCTC TCGCCGAGCC CCTCCGCAGA CTCTGCGCCG GAAAGTTTCA TTTGCTGTAT      60

GCCATCCTCG AGAGCTGTCT AGGTTAACGT TCGCACTCTG TGTATATAAC CTCGACAGT      120

TTGGCACCTA ACGTGCTGTG CGTAGCTGCT CCTTTGGTTG AATCCCCAGG CCCTTGTTG      180

GGCACAAGGT GGCAGG ATG TCT CAG TGG TAC GAA CTT CAG CAG CTT GAC         229
                  Met Ser Gln Trp Tyr Glu Leu Gln Gln Leu Asp
                   1               5                  10

TCA AAA TTC CTG GAG CAG GTT CAC CAG CTT TAT GAT GAC AGT TTT CCC       277
Ser Lys Phe Leu Glu Gln Val His Gln Leu Tyr Asp Asp Ser Phe Pro
             15                  20                  25

ATG GAA ATC AGA CAG TAC CTG GCA CAG TGG TTA GAA AAG CAA GAC TGG       325
Met Glu Ile Arg Gln Tyr Leu Ala Gln Trp Leu Glu Lys Gln Asp Trp
         30                  35                  40

GAG CAC GCT GCC AAT GAT GTT TCA TTT GCC ACC ATC CGT TTT CAT GAC       373
Glu His Ala Ala Asn Asp Val Ser Phe Ala Thr Ile Arg Phe His Asp
     45                  50                  55

CTC CTG TCA CAG CTG GAT GAT CAA TAT AGT CGC TTT TCT TTG GAG AAT       421
Leu Leu Ser Gln Leu Asp Asp Gln Tyr Ser Arg Phe Ser Leu Glu Asn
 60                  65                  70                  75

AAC TTC TTG CTA CAG CAT AAC ATA AGG AAA AGC AAG CGT AAT CTT CAG       469
Asn Phe Leu Leu Gln His Asn Ile Arg Lys Ser Lys Arg Asn Leu Gln
                 80                  85                  90

GAT AAT TTT CAG GAA GAC CCA ATC CAG ATG TCT ATG ATC ATT TAC AGC       517
Asp Asn Phe Gln Glu Asp Pro Ile Gln Met Ser Met Ile Ile Tyr Ser
             95                 100                 105

TGT CTG AAG GAA GAA AGG AAA ATT CTG GAA AAC GCC CAG AGA TTT AAT       565
Cys Leu Lys Glu Glu Arg Lys Ile Leu Glu Asn Ala Gln Arg Phe Asn
        110                 115                 120

CAG GCT CAG TCG GGG AAT ATT CAG AGC ACA GTG ATG TTA GAC AAA CAG       613
Gln Ala Gln Ser Gly Asn Ile Gln Ser Thr Val Met Leu Asp Lys Gln
    125                 130                 135

AAA GAG CTT GAC AGT AAA GTC AGA AAT GTG AAG GAC AAG GTT ATG TGT       661
Lys Glu Leu Asp Ser Lys Val Arg Asn Val Lys Asp Lys Val Met Cys
140                 145                 150                 155

ATA GAG CAT GAA ATC AAG AGC CTG GAA GAT TTA CAA GAT GAA TAT GAC       709
Ile Glu His Glu Ile Lys Ser Leu Glu Asp Leu Gln Asp Glu Tyr Asp
                160                 165                 170

TTC AAA TGC AAA ACC TTG CAG AAC AGA GAA CAC GAG ACC AAT GGT GTG       757
Phe Lys Cys Lys Thr Leu Gln Asn Arg Glu His Glu Thr Asn Gly Val
            175                 180                 185

GCA AAG AGT GAT CAG AAA CAA GAA CAG CTG TTA CTC AAG AAG ATG TAT       805
Ala Lys Ser Asp Gln Lys Gln Glu Gln Leu Leu Leu Lys Lys Met Tyr
        190                 195                 200

TTA ATG CTT GAC AAT AAG AGA AAG GAA GTA GTT CAC AAA ATA ATA GAG       853
Leu Met Leu Asp Asn Lys Arg Lys Glu Val Val His Lys Ile Ile Glu
    205                 210                 215

TTG CTG AAT GTC ACT GAA CTT ACC CAG AAT GCC CTG ATT AAT GAT GAA       901
Leu Leu Asn Val Thr Glu Leu Thr Gln Asn Ala Leu Ile Asn Asp Glu
220                 225                 230                 235

CTA GTG GAG TGG AAG CGG AGA CAG CAG AGC GCC TGT ATT GGG GGG CCG       949
Leu Val Glu Trp Lys Arg Arg Gln Gln Ser Ala Cys Ile Gly Gly Pro
                240                 245                 250

CCC AAT GCT TGC TTG GAT CAG CTG CAG AAC TGG TTC ACT ATA GTT GCG       997
Pro Asn Ala Cys Leu Asp Gln Leu Gln Asn Trp Phe Thr Ile Val Ala
            255                 260                 265

GAG AGT CTG CAG CAA GTT CGG CAG CAG CTT AAA AAG TTG GAG GAA TTG      1045
```

-continued

Glu Ser Leu Gln Gln Val Arg Gln Gln Leu Lys Lys Leu Glu Glu Leu
270 275 280

GAA CAG AAA TAC ACC TAC GAA CAT GAC CCT ATC ACA AAA AAC AAA CAA 1093
Glu Gln Lys Tyr Thr Tyr Glu His Asp Pro Ile Thr Lys Asn Lys Gln
285 290 295

GTG TTA TGG GAC CGC ACC TTC AGT CTT TTC CAG CAG CTC ATT CAG AGC 1141
Val Leu Trp Asp Arg Thr Phe Ser Leu Phe Gln Gln Leu Ile Gln Ser
300 305 310 315

TCG TTT GTG GTG GAA AGA CAG CCC TGC ATG CCA ACG CAC CCT CAG AGG 1189
Ser Phe Val Val Glu Arg Gln Pro Cys Met Pro Thr His Pro Gln Arg
320 325 330

CCG CTG GTC TTG AAG ACA GGG GTC CAG TTC ACT GTG AAG TTG AGA CTG 1237
Pro Leu Val Leu Lys Thr Gly Val Gln Phe Thr Val Lys Leu Arg Leu
335 340 345

TTG GTG AAA TTG CAA GAG CTG AAT TAT AAT TTG AAA GTC AAA GTC TTA 1285
Leu Val Lys Leu Gln Glu Leu Asn Tyr Asn Leu Lys Val Lys Val Leu
350 355 360

TTT GAT AAA GAT GTG AAT GAG AGA AAT ACA GTA AAA GGA TTT AGG AAG 1333
Phe Asp Lys Asp Val Asn Glu Arg Asn Thr Val Lys Gly Phe Arg Lys
365 370 375

TTC AAC ATT TTG GGC ACG CAC ACA AAA GTG ATG AAC ATG GAG GAG TCC 1381
Phe Asn Ile Leu Gly Thr His Thr Lys Val Met Asn Met Glu Glu Ser
380 385 390 395

ACC AAT GGC AGT CTG GCG GCT GAA TTT CGG CAC CTG CAA TTG AAA GAA 1429
Thr Asn Gly Ser Leu Ala Ala Glu Phe Arg His Leu Gln Leu Lys Glu
400 405 410

CAG AAA AAT GCT GGC ACC AGA ACG AAT GAG GGT CCT CTC ATC GTT ACT 1477
Gln Lys Asn Ala Gly Thr Arg Thr Asn Glu Gly Pro Leu Ile Val Thr
415 420 425

GAA GAG CTT CAC TCC CTT AGT TTT GAA ACC CAA TTG TGC CAG CCT GGT 1525
Glu Glu Leu His Ser Leu Ser Phe Glu Thr Gln Leu Cys Gln Pro Gly
430 435 440

TTG GTA ATT GAC CTC GAG ACG ACC TCT CTG CCC GTT GTG GTG ATC TCC 1573
Leu Val Ile Asp Leu Glu Thr Thr Ser Leu Pro Val Val Val Ile Ser
445 450 455

AAC GTC AGC CAG CTC CCG AGC GGT TGG GCC TCC ATC CTT TGG TAC AAC 1621
Asn Val Ser Gln Leu Pro Ser Gly Trp Ala Ser Ile Leu Trp Tyr Asn
460 465 470 475

ATG CTG GTG GCG GAA CCC AGG AAT CTG TCC TTC TTC CTG ACT CCA CCA 1669
Met Leu Val Ala Glu Pro Arg Asn Leu Ser Phe Phe Leu Thr Pro Pro
480 485 490

TGT GCA CGA TGG GCT CAG CTT TCA GAA GTG CTG AGT TGG CAG TTT TCT 1717
Cys Ala Arg Trp Ala Gln Leu Ser Glu Val Leu Ser Trp Gln Phe Ser
495 500 505

TCT GTC ACC AAA AGA GGT CTC AAT GTG GAC CAG CTG AAC ATG TTG GGA 1765
Ser Val Thr Lys Arg Gly Leu Asn Val Asp Gln Leu Asn Met Leu Gly
510 515 520

GAG AAG CTT CTT GGT CCT AAC GCC AGC CCC GAT GGT CTC ATT CCG TGG 1813
Glu Lys Leu Leu Gly Pro Asn Ala Ser Pro Asp Gly Leu Ile Pro Trp
525 530 535

ACG AGG TTT TGT AAG GAA AAT ATA AAT GAT AAA AAT TTT CCC TTC TGG 1861
Thr Arg Phe Cys Lys Glu Asn Ile Asn Asp Lys Asn Phe Pro Phe Trp
540 545 550 555

CTT TGG ATT GAA AGC ATC CTA GAA CTC ATT AAA AAA CAC CTG CTC CCT 1909
Leu Trp Ile Glu Ser Ile Leu Glu Leu Ile Lys Lys His Leu Leu Pro
560 565 570

CTC TGG AAT GAT GGG TGC ATC ATG GGC TTC ATC AGC AAG GAG CGA GAG 1957
Leu Trp Asn Asp Gly Cys Ile Met Gly Phe Ile Ser Lys Glu Arg Glu
575 580 585

CGT GCC CTG TTG AAG GAC CAG CAG CCG GGG ACC TTC CTG CTG CGG TTC 2005

-continued

```
Arg Ala Leu Leu Lys Asp Gln Gln Pro Gly Thr Phe Leu Leu Arg Phe
        590                     595                 600

AGT GAG AGC TCC CGG GAA GGG GCC ATC ACA TTC ACA TGG GTG GAG CGG     2053
Ser Glu Ser Ser Arg Glu Gly Ala Ile Thr Phe Thr Trp Val Glu Arg
    605                     610                 615

TCC CAG AAC GGA GGC GAA CCT GAC TTC CAT GCG GTT GAA CCC TAC ACG     2101
Ser Gln Asn Gly Gly Glu Pro Asp Phe His Ala Val Glu Pro Tyr Thr
620                     625                 630                 635

AAG AAA GAA CTT TCT GCT GTT ACT TTC CCT GAC ATC ATT CGC AAT TAC     2149
Lys Lys Glu Leu Ser Ala Val Thr Phe Pro Asp Ile Ile Arg Asn Tyr
                640                 645                 650

AAA GTC ATG GCT GCT GAG AAT ATT CCT GAG AAT CCC CTG AAG TAT CTG     2197
Lys Val Met Ala Ala Glu Asn Ile Pro Glu Asn Pro Leu Lys Tyr Leu
            655                 660                 665

TAT CCA AAT ATT GAC AAA GAC CAT GCC TTT GGA AAG TAT TAC TCC AGG     2245
Tyr Pro Asn Ile Asp Lys Asp His Ala Phe Gly Lys Tyr Tyr Ser Arg
        670                 675                 680

CCA AAG GAA GCA CCA GAG CCA ATG GAA CTT GAT GGC CCT AAA GGA ACT     2293
Pro Lys Glu Ala Pro Glu Pro Met Glu Leu Asp Gly Pro Lys Gly Thr
    685                 690                 695

GGA TAT ATC AAG ACT GAG TTG ATT TCT GTG TCT GAA GTG TAAGTGAACA      2342
Gly Tyr Ile Lys Thr Glu Leu Ile Ser Val Ser Glu Val
700                 705                 710

CAGAAGAGTG ACATGTTTAC AAACCTCAAG CCAGCCTTGC TCCTGGCTGG GGCCTGTT     2402

AGATGCTTGT ATTTTACTTT TCCATTGTAA TTGCTATCGC CATCACAGCT GAACTTGT     2462

AGATCCCCGT GTTACTGCCT ATCAGCATTT TACTACTTTA AAAAAAAAAA AAAAAGCC     2522

AAACCAAATT TGTATTTAAG GTATATAAAT TTTCCCAAAA CTGATACCCT TTGAAAAA     2582

ATAAATAAAA TGAGCAAAAG TTGAA                                         2607
```

( 2 ) INFORMATION FOR SEQ ID NO:6:

( i ) SEQUENCE CHARACTERISTICS:
( A ) LENGTH: 712 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Ser Gln Trp Tyr Glu Leu Gln Gln Leu Asp Ser Lys Phe Leu Glu
  1               5                  10                  15

Gln Val His Gln Leu Tyr Asp Asp Ser Phe Pro Met Glu Ile Arg Gln
             20                  25                  30

Tyr Leu Ala Gln Trp Leu Glu Lys Gln Asp Trp Glu His Ala Ala Asn
         35                  40                  45

Asp Val Ser Phe Ala Thr Ile Arg Phe His Asp Leu Leu Ser Gln Leu
     50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140
```

-continued

| | | | | | | | | | | | | | | | |
|---|---|---|---|---|---|---|---|---|---|---|---|---|---|---|---|
| Lys | Val | Arg | Asn | Val | Lys | Asp | Lys | Val | Met | Cys | Ile | Glu | His | Glu | Ile |
| 145 | | | | | 150 | | | | | 155 | | | | | 160 |
| Lys | Ser | Leu | Glu | Asp | Leu | Gln | Asp | Glu | Tyr | Asp | Phe | Lys | Cys | Lys | Thr |
| | | | | 165 | | | | | 170 | | | | | 175 | |
| Leu | Gln | Asn | Arg | Glu | His | Glu | Thr | Asn | Gly | Val | Ala | Lys | Ser | Asp | Gln |
| | | | 180 | | | | | 185 | | | | | 190 | | |
| Lys | Gln | Glu | Gln | Leu | Leu | Leu | Lys | Lys | Met | Tyr | Leu | Met | Leu | Asp | Asn |
| | | 195 | | | | | 200 | | | | | 205 | | | |
| Lys | Arg | Lys | Glu | Val | Val | His | Lys | Ile | Ile | Glu | Leu | Leu | Asn | Val | Thr |
| | 210 | | | | | 215 | | | | | 220 | | | | |
| Glu | Leu | Thr | Gln | Asn | Ala | Leu | Ile | Asn | Asp | Glu | Leu | Val | Glu | Trp | Lys |
| 225 | | | | | 230 | | | | | 235 | | | | | 240 |
| Arg | Arg | Gln | Gln | Ser | Ala | Cys | Ile | Gly | Gly | Pro | Pro | Asn | Ala | Cys | Leu |
| | | | | 245 | | | | | 250 | | | | | 255 | |
| Asp | Gln | Leu | Gln | Asn | Trp | Phe | Thr | Ile | Val | Ala | Glu | Ser | Leu | Gln | Gln |
| | | | 260 | | | | | 265 | | | | | 270 | | |
| Val | Arg | Gln | Gln | Leu | Lys | Lys | Leu | Glu | Glu | Leu | Glu | Gln | Lys | Tyr | Thr |
| | | 275 | | | | | 280 | | | | | 285 | | | |
| Tyr | Glu | His | Asp | Pro | Ile | Thr | Lys | Asn | Lys | Gln | Val | Leu | Trp | Asp | Arg |
| | 290 | | | | | 295 | | | | | 300 | | | | |
| Thr | Phe | Ser | Leu | Phe | Gln | Gln | Leu | Ile | Gln | Ser | Ser | Phe | Val | Val | Glu |
| 305 | | | | | 310 | | | | | 315 | | | | | 320 |
| Arg | Gln | Pro | Cys | Met | Pro | Thr | His | Pro | Gln | Arg | Pro | Leu | Val | Leu | Lys |
| | | | | 325 | | | | | 330 | | | | | 335 | |
| Thr | Gly | Val | Gln | Phe | Thr | Val | Lys | Leu | Arg | Leu | Leu | Val | Lys | Leu | Gln |
| | | | 340 | | | | | 345 | | | | | 350 | | |
| Glu | Leu | Asn | Tyr | Asn | Leu | Lys | Val | Lys | Val | Leu | Phe | Asp | Lys | Asp | Val |
| | | 355 | | | | | 360 | | | | | 365 | | | |
| Asn | Glu | Arg | Asn | Thr | Val | Lys | Gly | Phe | Arg | Lys | Phe | Asn | Ile | Leu | Gly |
| | 370 | | | | | 375 | | | | | 380 | | | | |
| Thr | His | Thr | Lys | Val | Met | Asn | Met | Glu | Glu | Ser | Thr | Asn | Gly | Ser | Leu |
| 385 | | | | | 390 | | | | | 395 | | | | | 400 |
| Ala | Ala | Glu | Phe | Arg | His | Leu | Gln | Leu | Lys | Glu | Gln | Lys | Asn | Ala | Gly |
| | | | | 405 | | | | | 410 | | | | | 415 | |
| Thr | Arg | Thr | Asn | Glu | Gly | Pro | Leu | Ile | Val | Thr | Glu | Glu | Leu | His | Ser |
| | | | 420 | | | | | 425 | | | | | 430 | | |
| Leu | Ser | Phe | Glu | Thr | Gln | Leu | Cys | Gln | Pro | Gly | Leu | Val | Ile | Asp | Leu |
| | | 435 | | | | | 440 | | | | | 445 | | | |
| Glu | Thr | Thr | Ser | Leu | Pro | Val | Val | Val | Ile | Ser | Asn | Val | Ser | Gln | Leu |
| | 450 | | | | | 455 | | | | | 460 | | | | |
| Pro | Ser | Gly | Trp | Ala | Ser | Ile | Leu | Trp | Tyr | Asn | Met | Leu | Val | Ala | Glu |
| 465 | | | | | 470 | | | | | 475 | | | | | 480 |
| Pro | Arg | Asn | Leu | Ser | Phe | Phe | Leu | Thr | Pro | Pro | Cys | Ala | Arg | Trp | Ala |
| | | | | 485 | | | | | 490 | | | | | 495 | |
| Gln | Leu | Ser | Glu | Val | Leu | Ser | Trp | Gln | Phe | Ser | Ser | Val | Thr | Lys | Arg |
| | | | 500 | | | | | 505 | | | | | 510 | | |
| Gly | Leu | Asn | Val | Asp | Gln | Leu | Asn | Met | Leu | Gly | Glu | Lys | Leu | Leu | Gly |
| | | 515 | | | | | 520 | | | | | 525 | | | |
| Pro | Asn | Ala | Ser | Pro | Asp | Gly | Leu | Ile | Pro | Trp | Thr | Arg | Phe | Cys | Lys |
| | 530 | | | | | 535 | | | | | 540 | | | | |
| Glu | Asn | Ile | Asn | Asp | Lys | Asn | Phe | Pro | Phe | Trp | Leu | Trp | Ile | Glu | Ser |
| 545 | | | | | 550 | | | | | 555 | | | | | 560 |
| Ile | Leu | Glu | Leu | Ile | Lys | Lys | His | Leu | Leu | Pro | Leu | Trp | Asn | Asp | Gly |
| | | | | 565 | | | | | 570 | | | | | 575 | |

Cys Ile Met Gly Phe Ile Ser Lys Glu Arg Glu Arg Ala Leu Leu Lys
580 585 590

Asp Gln Gln Pro Gly Thr Phe Leu Leu Arg Phe Ser Glu Ser Ser Arg
595 600 605

Glu Gly Ala Ile Thr Phe Thr Trp Val Glu Arg Ser Gln Asn Gly Gly
610 615 620

Glu Pro Asp Phe His Ala Val Glu Pro Tyr Thr Lys Lys Glu Leu Ser
625 630 635 640

Ala Val Thr Phe Pro Asp Ile Ile Arg Asn Tyr Lys Val Met Ala Ala
645 650 655

Glu Asn Ile Pro Glu Asn Pro Leu Lys Tyr Leu Tyr Pro Asn Ile Asp
660 665 670

Lys Asp His Ala Phe Gly Lys Tyr Tyr Ser Arg Pro Lys Glu Ala Pro
675 680 685

Glu Pro Met Glu Leu Asp Gly Pro Lys Gly Thr Gly Tyr Ile Lys Thr
690 695 700

Glu Leu Ile Ser Val Ser Glu Val
705 710

( 2 ) INFORMATION FOR SEQ ID NO:7:

( i ) SEQUENCE CHARACTERISTICS:
( A ) LENGTH: 2277 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Mouse ( v i i ) IMMEDIATE SOURCE:
( B ) CLONE: Murine Stat91

( i x ) FEATURE:
( A ) NAME/KEY: CDS
( B ) LOCATION: 5..2251

( x i ) SEQUENCE DESCRIPTION: SEQ ID NO:7:

CAGG ATG TCA CAG TGG TTC GAG CTT CAG CAG CTG GAC TCC AAG TTC CTG 49
Met Ser Gln Trp Phe Glu Leu Gln Gln Leu Asp Ser Lys Phe Leu
1 5 10 15

GAG CAG GTC CAC CAG CTG TAC GAT GAC AGT TTC CCC ATG GAA ATC AGA 97
Glu Gln Val His Gln Leu Tyr Asp Asp Ser Phe Pro Met Glu Ile Arg
20 25 30

CAG TAC CTG GCC CAG TGG CTG GAA AAG CAA GAC TGG GAG CAC GCT GCC 145
Gln Tyr Leu Ala Gln Trp Leu Glu Lys Gln Asp Trp Glu His Ala Ala
35 40 45

TAT GAT GTC TCG TTT GCG ACC ATC CGC TTC CAT GAC CTC CTC TCA CAG 193
Tyr Asp Val Ser Phe Ala Thr Ile Arg Phe His Asp Leu Leu Ser Gln
50 55 60

CTG GAC GAC CAG TAC AGC CGC TTT TCT CTG GAG AAT AAT TTC TTG TTG 241
Leu Asp Asp Gln Tyr Ser Arg Phe Ser Leu Glu Asn Asn Phe Leu Leu
65 70 75

CAG CAC AAC ATA CGG AAA AGC AAG CGT AAT CTC CAG GAT AAC TTC CAA 289
Gln His Asn Ile Arg Lys Ser Lys Arg Asn Leu Gln Asp Asn Phe Gln
80 85 90 95

GAA GAT CCC GTA CAG ATG TCC ATG ATC ATC TAC AAC TGT CTG AAG GAA 337

-continued

```
Glu Asp Pro Val Gln Met Ser Met Ile Ile Tyr Asn Cys Leu Lys Glu
                100                 105                 110

GAA AGG AAG ATT TTG GAA AAT GCC CAA AGA TTT AAT CAG GCC CAG GAG      385
Glu Arg Lys Ile Leu Glu Asn Ala Gln Arg Phe Asn Gln Ala Gln Glu
            115                 120                 125

GGA AAT ATT CAG AAC ACT GTG ATG TTA GAT AAA CAG AAG GAG CTG GAC      433
Gly Asn Ile Gln Asn Thr Val Met Leu Asp Lys Gln Lys Glu Leu Asp
        130                 135                 140

AGT AAA GTC AGA AAT GTG AAG GAT CAA GTC ATG TGC ATA GAG CAG GAA      481
Ser Lys Val Arg Asn Val Lys Asp Gln Val Met Cys Ile Glu Gln Glu
    145                 150                 155

ATC AAG ACC CTA GAA GAA TTA CAA GAT GAA TAT GAC TTT AAA TGC AAA      529
Ile Lys Thr Leu Glu Glu Leu Gln Asp Glu Tyr Asp Phe Lys Cys Lys
160                 165                 170                 175

ACC TCT CAG AAC AGA GAA GGT GAA GCC AAT GGT GTG GCG AAG AGC GAC      577
Thr Ser Gln Asn Arg Glu Gly Glu Ala Asn Gly Val Ala Lys Ser Asp
                180                 185                 190

CAA AAA CAG GAA CAG CTG CTG CTC CAC AAG ATG TTT TTA ATG CTT GAC      625
Gln Lys Gln Glu Gln Leu Leu Leu His Lys Met Phe Leu Met Leu Asp
            195                 200                 205

AAT AAG AGA AAG GAG ATA ATT CAC AAA ATC AGA GAG TTG CTG AAT TCC      673
Asn Lys Arg Lys Glu Ile Ile His Lys Ile Arg Glu Leu Leu Asn Ser
        210                 215                 220

ATC GAG CTC ACT CAG AAC ACT CTG ATT AAT GAC GAG CTC GTG GAG TGG      721
Ile Glu Leu Thr Gln Asn Thr Leu Ile Asn Asp Glu Leu Val Glu Trp
    225                 230                 235

AAG CGA AGG CAG CAG AGC GCC TGC ATC GGG GGA CCG CCC AAC GCC TGC      769
Lys Arg Arg Gln Gln Ser Ala Cys Ile Gly Gly Pro Pro Asn Ala Cys
240                 245                 250                 255

CTG GAT CAG CTG CAA ACG TGG TTC ACC ATT GTT GCA GAG ACC CTG CAG      817
Leu Asp Gln Leu Gln Thr Trp Phe Thr Ile Val Ala Glu Thr Leu Gln
                260                 265                 270

CAG ATC CGT CAG CAG CTT AAA AAG CTG GAG GAG TTG GAA CAG AAA TTC      865
Gln Ile Arg Gln Gln Leu Lys Lys Leu Glu Glu Leu Glu Gln Lys Phe
            275                 280                 285

ACC TAT GAG CCC GAC CCT ATT ACA AAA AAC AAG CAG GTG TTG TCA GAT      913
Thr Tyr Glu Pro Asp Pro Ile Thr Lys Asn Lys Gln Val Leu Ser Asp
        290                 295                 300

CGA ACC TTC CTC CTC TTC CAG CAG CTC ATT CAG AGC TCC TTC GTG GTA      961
Arg Thr Phe Leu Leu Phe Gln Gln Leu Ile Gln Ser Ser Phe Val Val
    305                 310                 315

GAA CGA CAG CCG TGC ATG CCC ACT CAC CCG CAG AGG CCC CTG GTC TTG     1009
Glu Arg Gln Pro Cys Met Pro Thr His Pro Gln Arg Pro Leu Val Leu
320                 325                 330                 335

AAG ACT GGG GTA CAG TTC ACT GTC AAG TCG AGA CTG TTG GTG AAA TTG     1057
Lys Thr Gly Val Gln Phe Thr Val Lys Ser Arg Leu Leu Val Lys Leu
                340                 345                 350

CAA GAG TCG AAT CTA TTA ACG AAA GTG AAA TGT CAC TTT GAC AAA GAT     1105
Gln Glu Ser Asn Leu Leu Thr Lys Val Lys Cys His Phe Asp Lys Asp
            355                 360                 365

GTG AAC GAG AAA AAC ACA GTT AAA GGA TTT CGG AAG TTC AAC ATC TTG     1153
Val Asn Glu Lys Asn Thr Val Lys Gly Phe Arg Lys Phe Asn Ile Leu
        370                 375                 380

GGT ACG CAC ACA AAA GTG ATG AAC ATG GAA GAA TCC ACC AAC GGA AGT     1201
Gly Thr His Thr Lys Val Met Asn Met Glu Glu Ser Thr Asn Gly Ser
    385                 390                 395

CTG GCA GCT GAG CTC CGA CAC CTG CAA CTG AAG GAA CAG AAA AAC GCT     1249
Leu Ala Ala Glu Leu Arg His Leu Gln Leu Lys Glu Gln Lys Asn Ala
400                 405                 410                 415

GGG AAC AGA ACT AAT GAG GGG CCT CTC ATT GTC ACC GAA GAA CTT CAC     1297
```

-continued

```
Gly Asn Arg Thr Asn Glu Gly Pro Leu Ile Val Thr Glu Glu Leu His
                420             425                 430

TCT CTT AGC TTT GAA ACC CAG TTG TGC CAG CCA GGC TTG GTG ATT GAC      1345
Ser Leu Ser Phe Glu Thr Gln Leu Cys Gln Pro Gly Leu Val Ile Asp
            435                 440                 445

CTG GAG ACC ACC TCT CTT CCT GTC GTG GTG ATC TCC AAC GTC AGC CAG      1393
Leu Glu Thr Thr Ser Leu Pro Val Val Val Ile Ser Asn Val Ser Gln
        450                 455                 460

CTC CCC AGT GGC TGG GCG TCT ATC CTG TGG TAC AAC ATG CTG GTG ACA      1441
Leu Pro Ser Gly Trp Ala Ser Ile Leu Trp Tyr Asn Met Leu Val Thr
    465                 470                 475

GAG CCC AGG AAT CTC TCC TTC TTC CTG AAC CCC CCG TGC GCG TGG TGG      1489
Glu Pro Arg Asn Leu Ser Phe Phe Leu Asn Pro Pro Cys Ala Trp Trp
480                 485                 490                 495

TCC CAG CTC TCA GAG GTG TTG AGT TGG CAG TTT TCA TCA GTC ACC AAG      1537
Ser Gln Leu Ser Glu Val Leu Ser Trp Gln Phe Ser Ser Val Thr Lys
                500                 505                 510

AGA GGT CTG AAC GCA GAC CAG CTG AGC ATG CTG GGA GAG AAG CTG CTG      1585
Arg Gly Leu Asn Ala Asp Gln Leu Ser Met Leu Gly Glu Lys Leu Leu
            515                 520                 525

GGC CCT AAT GCT GGC CCT GAT GGT CTT ATT CCA TGG ACA AGG TTT TGT      1633
Gly Pro Asn Ala Gly Pro Asp Gly Leu Ile Pro Trp Thr Arg Phe Cys
        530                 535                 540

AAG GAA AAT ATT AAT GAT AAA AAT TTC TCC TTC TGG CCT TGG ATT GAC      1681
Lys Glu Asn Ile Asn Asp Lys Asn Phe Ser Phe Trp Pro Trp Ile Asp
    545                 550                 555

ACC ATC CTA GAG CTC ATT AAG AAC GAC CTG CTG TGC CTC TGG AAT GAT      1729
Thr Ile Leu Glu Leu Ile Lys Asn Asp Leu Leu Cys Leu Trp Asn Asp
560                 565                 570                 575

GGG TGC ATT ATG GGC TTC ATC AGC AAG GAG CGA GAA CGC GCT CTG CTC      1777
Gly Cys Ile Met Gly Phe Ile Ser Lys Glu Arg Glu Arg Ala Leu Leu
                580                 585                 590

AAG GAC CAG CAG CCA GGG ACG TTC CTG CTT AGA TTC AGT GAG AGC TCC      1825
Lys Asp Gln Gln Pro Gly Thr Phe Leu Leu Arg Phe Ser Glu Ser Ser
            595                 600                 605

CGG GAA GGG GCC ATC ACA TTC ACA TGG GTG GAA CGG TCC CAG AAC GGA      1873
Arg Glu Gly Ala Ile Thr Phe Thr Trp Val Glu Arg Ser Gln Asn Gly
        610                 615                 620

GGT GAA CCT GAC TTC CAT GCC GTG GAG CCC TAC ACG AAA AAA GAA CTT      1921
Gly Glu Pro Asp Phe His Ala Val Glu Pro Tyr Thr Lys Lys Glu Leu
    625                 630                 635

TCA GCT GTT ACT TTC CCA GAT ATT ATT CGC AAC TAC AAA GTC ATG GCT      1969
Ser Ala Val Thr Phe Pro Asp Ile Ile Arg Asn Tyr Lys Val Met Ala
640                 645                 650                 655

GCC GAG AAC ATA CCA GAG AAT CCC CTG AAG TAT CTG TAC CCC AAT ATT      2017
Ala Glu Asn Ile Pro Glu Asn Pro Leu Lys Tyr Leu Tyr Pro Asn Ile
                660                 665                 670

GAC AAA GAC CAC GCC TTT GGG AAG TAT TAT TCC AGA CCA AAG GAA GCA      2065
Asp Lys Asp His Ala Phe Gly Lys Tyr Tyr Ser Arg Pro Lys Glu Ala
            675                 680                 685

CCA GAA CCG ATG GAG CTT GAC GAC CCT AAG CGA ACT GGA TAC ATC AAG      2113
Pro Glu Pro Met Glu Leu Asp Asp Pro Lys Arg Thr Gly Tyr Ile Lys
        690                 695                 700

ACT GAG TTG ATT TCT GTG TCT GAA GTC CAC CCT TCT AGA CTT CAG ACC      2161
Thr Glu Leu Ile Ser Val Ser Glu Val His Pro Ser Arg Leu Gln Thr
    705                 710                 715

ACA GAC AAC CTG CTT CCC ATG TCT CCA GAG GAG TTT GAT GAG ATG TCC      2209
Thr Asp Asn Leu Leu Pro Met Ser Pro Glu Glu Phe Asp Glu Met Ser
720                 725                 730                 735

CGG ATA GTG GGC CCC GAA TTT GAC AGT ATG ATG AGC ACA GTA              2251
```

-continued

Arg Ile Val Gly Pro Glu Phe Asp Ser Met Met Ser Thr Val
740 745

TAAACACGAA TTTCTCTCTG GCGACA 2277

( 2 ) INFORMATION FOR SEQ ID NO:8:

( i ) SEQUENCE CHARACTERISTICS:
( A ) LENGTH: 749 amino acids
( B ) TYPE: amino acid
( D ) TOPOLOGY: linear ( i i ) MOLECULE TYPE: protein ( x i ) SEQUENCE DESCRIPTION: SEQ ID NO:8:

Met Ser Gln Trp Phe Glu Leu Gln Gln Leu Asp Ser Lys Phe Leu Glu
1 5 10 15

Gln Val His Gln Leu Tyr Asp Asp Ser Phe Pro Met Glu Ile Arg Gln
20 25 30

Tyr Leu Ala Gln Trp Leu Glu Lys Gln Asp Trp Glu His Ala Ala Tyr
35 40 45

Asp Val Ser Phe Ala Thr Ile Arg Phe His Asp Leu Leu Ser Gln Leu
50 55 60

Asp Asp Gln Tyr Ser Arg Phe Ser Leu Glu Asn Asn Phe Leu Leu Gln
65 70 75 80

His Asn Ile Arg Lys Ser Lys Arg Asn Leu Gln Asp Asn Phe Gln Glu
85 90 95

Asp Pro Val Gln Met Ser Met Ile Ile Tyr Asn Cys Leu Lys Glu Glu
100 105 110

Arg Lys Ile Leu Glu Asn Ala Gln Arg Phe Asn Gln Ala Gln Glu Gly
115 120 125

Asn Ile Gln Asn Thr Val Met Leu Asp Lys Gln Lys Glu Leu Asp Ser
130 135 140

Lys Val Arg Asn Val Lys Asp Gln Val Met Cys Ile Glu Gln Glu Ile
145 150 155 160

Lys Thr Leu Glu Glu Leu Gln Asp Glu Tyr Asp Phe Lys Cys Lys Thr
165 170 175

Ser Gln Asn Arg Glu Gly Glu Ala Asn Gly Val Ala Lys Ser Asp Gln
180 185 190

Lys Gln Glu Gln Leu Leu Leu His Lys Met Phe Leu Met Leu Asp Asn
195 200 205

Lys Arg Lys Glu Ile Ile His Lys Ile Arg Glu Leu Leu Asn Ser Ile
210 215 220

Glu Leu Thr Gln Asn Thr Leu Ile Asn Asp Glu Leu Val Glu Trp Lys
225 230 235 240

Arg Arg Gln Gln Ser Ala Cys Ile Gly Gly Pro Pro Asn Ala Cys Leu
245 250 255

Asp Gln Leu Gln Thr Trp Phe Thr Ile Val Ala Glu Thr Leu Gln Gln
260 265 270

Ile Arg Gln Gln Leu Lys Lys Leu Glu Glu Leu Glu Gln Lys Phe Thr
275 280 285

Tyr Glu Pro Asp Pro Ile Thr Lys Asn Lys Gln Val Leu Ser Asp Arg
290 295 300

Thr Phe Leu Leu Phe Gln Gln Leu Ile Gln Ser Ser Phe Val Val Glu
305 310 315 320

Arg Gln Pro Cys Met Pro Thr His Pro Gln Arg Pro Leu Val Leu Lys
325 330 335

-continued

```
Thr Gly Val Gln Phe Thr Val Lys Ser Arg Leu Leu Val Lys Leu Gln
            340                 345                 350

Glu Ser Asn Leu Leu Thr Lys Val Lys Cys His Phe Asp Lys Asp Val
        355                 360                 365

Asn Glu Lys Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Leu Arg His Leu Gln Leu Lys Glu Gln Lys Asn Ala Gly
                405                 410                 415

Asn Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Val Ile Ser Asn Val Ser Gln Leu
    450                 455                 460

Pro Ser Gly Trp Ala Ser Ile Leu Trp Tyr Asn Met Leu Val Thr Glu
465                 470                 475                 480

Pro Arg Asn Leu Ser Phe Phe Leu Asn Pro Pro Cys Ala Trp Trp Ser
                485                 490                 495

Gln Leu Ser Glu Val Leu Ser Trp Gln Phe Ser Ser Val Thr Lys Arg
            500                 505                 510

Gly Leu Asn Ala Asp Gln Leu Ser Met Leu Gly Glu Lys Leu Leu Gly
        515                 520                 525

Pro Asn Ala Gly Pro Asp Gly Leu Ile Pro Trp Thr Arg Phe Cys Lys
    530                 535                 540

Glu Asn Ile Asn Asp Lys Asn Phe Ser Phe Trp Pro Trp Ile Asp Thr
545                 550                 555                 560

Ile Leu Glu Leu Ile Lys Asn Asp Leu Leu Cys Leu Trp Asn Asp Gly
                565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
        595                 600                 605

Glu Gly Ala Ile Thr Phe Thr Trp Val Glu Arg Ser Gln Asn Gly Gly
    610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
        675                 680                 685

Glu Pro Met Glu Leu Asp Asp Pro Lys Arg Thr Gly Tyr Ile Lys Thr
    690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Met Ser Arg
                725                 730                 735

Ile Val Gly Pro Glu Phe Asp Ser Met Met Ser Thr Val
            740                 745
```

( 2 ) INFORMATION FOR SEQ ID NO:9:

( i ) SEQUENCE CHARACTERISTICS:
( A ) LENGTH: 2375 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Mouse ( v i i ) IMMEDIATE SOURCE:
( A ) LIBRARY: splenic/thymic
( B ) CLONE: Murine 13sf1

( i x ) FEATURE:
( A ) NAME/KEY: CDS
( B ) LOCATION: 34..2277

( x i ) SEQUENCE DESCRIPTION: SEQ ID NO:9:

```
TGCCACTACC TGGACGGAGA GAGAGAGAGC AGC ATG TCT CAG TGG AAT CAA GTC     54
                                     Met Ser Gln Trp Asn Gln Val
                                       1               5

CAA CAA TTA GAA ATC AAG TTT TTG GAG CAA GTA GAT CAG TTC TAT GAT     102
Gln Gln Leu Glu Ile Lys Phe Leu Glu Gln Val Asp Gln Phe Tyr Asp
         10                  15                  20

GAC AAC TTT CCT ATG GAA ATC CGG CAT CTG CTA GCT CAG TGG ATT GAG     150
Asp Asn Phe Pro Met Glu Ile Arg His Leu Leu Ala Gln Trp Ile Glu
     25                  30                  35

ACT CAA GAC TGG GAA GTA GCT TCT AAC AAT GAA ACT ATG GCA ACA ATT     198
Thr Gln Asp Trp Glu Val Ala Ser Asn Asn Glu Thr Met Ala Thr Ile
 40                  45                  50                  55

CTG CTT CAA AAC TTA CTA ATA CAA TTG GAT GAA CAG TTG GGG CGG GTT     246
Leu Leu Gln Asn Leu Leu Ile Gln Leu Asp Glu Gln Leu Gly Arg Val
                 60                  65                  70

TCC AAA GAA AAA AAT CTG CTA TTG ATT CAC AAT CTA AAG AGA ATT AGA     294
Ser Lys Glu Lys Asn Leu Leu Leu Ile His Asn Leu Lys Arg Ile Arg
             75                  80                  85

AAA GTT CTT CAG GGC AAG TTT CAT GGA AAT CCA ATG CAT GTA GCT GTG     342
Lys Val Leu Gln Gly Lys Phe His Gly Asn Pro Met His Val Ala Val
         90                  95                 100

GTA ATT TCA AAT TGC TTA AGG GAA GAG AGG AGA ATA TTG GCT GCA GCC     390
Val Ile Ser Asn Cys Leu Arg Glu Glu Arg Arg Ile Leu Ala Ala Ala
    105                 110                 115

AAC ATG CCT ATC CAG GGA CCT CTG GAG AAA TCC TTA CAG AGT TCT TCA     438
Asn Met Pro Ile Gln Gly Pro Leu Glu Lys Ser Leu Gln Ser Ser Ser
120                 125                 130                 135

GTT TCT GAA AGA CAA AGG AAT GTG GAA CAC AAA GTG TCT GCC ATT AAA     486
Val Ser Glu Arg Gln Arg Asn Val Glu His Lys Val Ser Ala Ile Lys
                140                 145                 150

AAC AGT GTG CAG ATG ACA GAA CAA GAT ACC AAA TAC TTA GAA GAC CTG     534
Asn Ser Val Gln Met Thr Glu Gln Asp Thr Lys Tyr Leu Glu Asp Leu
            155                 160                 165

CAA GAT GAG TTT GAC TAC AGG TAT AAA ACA ATT CAG ACA ATG GAT CAG     582
Gln Asp Glu Phe Asp Tyr Arg Tyr Lys Thr Ile Gln Thr Met Asp Gln
        170                 175                 180

GGT GAC AAA AAC AGT ATC CTG GTG AAC CAG GAA GTT TTG ACA CTG CTG     630
Gly Asp Lys Asn Ser Ile Leu Val Asn Gln Glu Val Leu Thr Leu Leu
    185                 190                 195

CAA GAA ATG CTT AAT AGT CTG GAC TTC AAG AGA AAG GAA GCA CTC AGT     678
Gln Glu Met Leu Asn Ser Leu Asp Phe Lys Arg Lys Glu Ala Leu Ser
```

-continued

```
200                 205                 210                 215

AAG ATG ACG CAG ATA GTG AAC GAG ACA GAC CTG CTC ATG AAC AGC ATG     726
Lys Met Thr Gln Ile Val Asn Glu Thr Asp Leu Leu Met Asn Ser Met
                220                 225                 230

CTT CTA GAA GAG CTG CAG GAC TGG AAA AAG CGG CAC AGG ATT GCC TGC     774
Leu Leu Glu Glu Leu Gln Asp Trp Lys Lys Arg His Arg Ile Ala Cys
            235                 240                 245

ATT GGT GGC CCG CTC CAC AAT GGG CTG GAC CAG CTT CAG AAC TGC TTT     822
Ile Gly Gly Pro Leu His Asn Gly Leu Asp Gln Leu Gln Asn Cys Phe
        250                 255                 260

ACC CTA CTG GCA GAG AGT CTT TTC CAA CTC AGA CAG CAA CTG GAG AAA     870
Thr Leu Leu Ala Glu Ser Leu Phe Gln Leu Arg Gln Gln Leu Glu Lys
    265                 270                 275

CTA CAG GAG CAA TCT ACT AAA ATG ACC TAT GAA GGG GAT CCC ATC CCT     918
Leu Gln Glu Gln Ser Thr Lys Met Thr Tyr Glu Gly Asp Pro Ile Pro
280                 285                 290                 295

GCT CAA AGA GCA CAC CTC CTG GAA AGA GCT ACC TTC CTG ATC TAC AAC     966
Ala Gln Arg Ala His Leu Leu Glu Arg Ala Thr Phe Leu Ile Tyr Asn
                300                 305                 310

CTT TTC AAG AAC TCA TTT GTG GTC GAG CGA CAC GCA TGC ATG CCA ACG    1014
Leu Phe Lys Asn Ser Phe Val Val Glu Arg His Ala Cys Met Pro Thr
            315                 320                 325

CAC CCT CAG AGG CCG ATG GTA CTT AAA ACC CTC ATT CAG TTC ACT GTA    1062
His Pro Gln Arg Pro Met Val Leu Lys Thr Leu Ile Gln Phe Thr Val
        330                 335                 340

AAA CTG AGA TTA CTA ATA AAA TTG CCG GAA CTA AAC TAT CAG GTG AAA    1110
Lys Leu Arg Leu Leu Ile Lys Leu Pro Glu Leu Asn Tyr Gln Val Lys
    345                 350                 355

GTA AAG GCG TCC ATT GAC AAG AAT GTT TCA ACT CTA AGC AAT AGA AGA    1158
Val Lys Ala Ser Ile Asp Lys Asn Val Ser Thr Leu Ser Asn Arg Arg
360                 365                 370                 375

TTT GTG CTT TGT GGA ACT CAC GTC AAA GCT ATG TCC AGT GAG GAA TCT    1206
Phe Val Leu Cys Gly Thr His Val Lys Ala Met Ser Ser Glu Glu Ser
                380                 385                 390

TCC AAT GGG AGC CTC TCA GTG GAG TTA GAC ATT GCA ACC CAA GGA GAT    1254
Ser Asn Gly Ser Leu Ser Val Glu Leu Asp Ile Ala Thr Gln Gly Asp
            395                 400                 405

GAA GTG CAG TAC TGG AGT AAA GGA AAC GAG GGC TGC CAC ATG GTG ACA    1302
Glu Val Gln Tyr Trp Ser Lys Gly Asn Glu Gly Cys His Met Val Thr
        410                 415                 420

GAG GAG TTG CAT TCC ATA ACC TTT GAG ACC CAG ATC TGC CTC TAT GGC    1350
Glu Glu Leu His Ser Ile Thr Phe Glu Thr Gln Ile Cys Leu Tyr Gly
    425                 430                 435

CTC ACC ATT AAC CTA GAG ACC AGC TCA TTA CCT GTC GTG ATG ATT TCT    1398
Leu Thr Ile Asn Leu Glu Thr Ser Ser Leu Pro Val Val Met Ile Ser
440                 445                 450                 455

AAT GTC AGC CAA CTA CCT AAT GCA TGG GCA TCC ATC ATT TGG TAC AAT    1446
Asn Val Ser Gln Leu Pro Asn Ala Trp Ala Ser Ile Ile Trp Tyr Asn
                460                 465                 470

GTA TCA ACT AAC GAC TCC CAG AAC TTG GTT TTC TTT AAT AAC CCT CCA    1494
Val Ser Thr Asn Asp Ser Gln Asn Leu Val Phe Phe Asn Asn Pro Pro
            475                 480                 485

TCT GTC ACT TTG GGC CAA CTC CTG GAA GTG ATG AGC TGG CAA TTT TCA    1542
Ser Val Thr Leu Gly Gln Leu Leu Glu Val Met Ser Trp Gln Phe Ser
        490                 495                 500

TCC TAT GTC GGT CGT GGC CTT AAT TCA GAG CAG CTC AAC ATG CTG GCA    1590
Ser Tyr Val Gly Arg Gly Leu Asn Ser Glu Gln Leu Asn Met Leu Ala
    505                 510                 515

GAG AAG CTC ACA GTT CAG TCT AAC TAC AAT GAT GGT CAC CTC ACC TGG    1638
Glu Lys Leu Thr Val Gln Ser Asn Tyr Asn Asp Gly His Leu Thr Trp
```

-continued

```
520                     525                     530                     535

GCC AAG TTC TGC AAG GAA CAT TTG CCT GGC AAA ACA TTT ACC TTC TGG     1686
Ala Lys Phe Cys Lys Glu His Leu Pro Gly Lys Thr Phe Thr Phe Trp
                540                     545                     550

ACT TGG CTT GAA GCA ATA TTG GAC CTA ATT AAA AAA CAT ATT CTT CCC     1734
Thr Trp Leu Glu Ala Ile Leu Asp Leu Ile Lys Lys His Ile Leu Pro
            555                     560                     565

CTC TGG ATT GAT GGG TAC ATC ATG GGA TTT GTT AGT AAA GAG AAG GAA     1782
Leu Trp Ile Asp Gly Tyr Ile Met Gly Phe Val Ser Lys Glu Lys Glu
        570                     575                     580

CGG CTT CTG CTC AAA GAT AAA ATG CCT GGG ACA TTT TTG TTA AGA TTC     1830
Arg Leu Leu Leu Lys Asp Lys Met Pro Gly Thr Phe Leu Leu Arg Phe
    585                     590                     595

AGT GAG AGC CAT CTT GGA GGG ATA ACC TTC ACC TGG GTG GAC CAA TCT     1878
Ser Glu Ser His Leu Gly Gly Ile Thr Phe Thr Trp Val Asp Gln Ser
600                     605                     610                     615

GAA AAT GGA GAA GTG AGA TTC CAC TCT GTA GAA CCC TAC AAC AAA GGG     1926
Glu Asn Gly Glu Val Arg Phe His Ser Val Glu Pro Tyr Asn Lys Gly
                620                     625                     630

AGA CTG TCG GCT CTG GCC TTC GCT GAC ATC CTG CGA GAC TAC AAG GTT     1974
Arg Leu Ser Ala Leu Ala Phe Ala Asp Ile Leu Arg Asp Tyr Lys Val
            635                     640                     645

ATC ATG GCT GAA AAC ATC CCT GAA AAC CCT CTG AAG TAC CTC TAC CCT     2022
Ile Met Ala Glu Asn Ile Pro Glu Asn Pro Leu Lys Tyr Leu Tyr Pro
        650                     655                     660

GAC ATT CCC AAA GAC AAA GCC TTT GGC AAA CAC TAC AGC TCC CAG CCG     2070
Asp Ile Pro Lys Asp Lys Ala Phe Gly Lys His Tyr Ser Ser Gln Pro
    665                     670                     675

TGC GAA GTC TCA AGA CCA ACC GAA CGG GGA GAC AAG GGT TAC GTC CCC     2118
Cys Glu Val Ser Arg Pro Thr Glu Arg Gly Asp Lys Gly Tyr Val Pro
680                     685                     690                     695

TCT GTT TTT ATC CCC ATT TCA ACA ATC CGA AGC GAT TCC ACG GAG CCA     2166
Ser Val Phe Ile Pro Ile Ser Thr Ile Arg Ser Asp Ser Thr Glu Pro
                700                     705                     710

CAA TCT CCT TCA GAC CTT CTC CCC ATG TCT CCA AGT GCA TAT GCT GTG     2214
Gln Ser Pro Ser Asp Leu Leu Pro Met Ser Pro Ser Ala Tyr Ala Val
            715                     720                     725

CTG AGA GAA AAC CTG AGC CCA ACG ACA ATT GAA ACT GCA ATG AAT TCC     2262
Leu Arg Glu Asn Leu Ser Pro Thr Thr Ile Glu Thr Ala Met Asn Ser
        730                     735                     740

CCA TAT TCT GCT GAA TGACGGTGCA AACGGACACT TTAAAGAAGG AAGCAGATGA     2317
Pro Tyr Ser Ala Glu
    745

AACTGGAGAG TGTTCTTTAC CATAGATCAC AATTTATTTC TTCGGCTTTG TAAATACC     2375
```

( 2 ) INFORMATION FOR SEQ ID NO:10:

( i ) SEQUENCE CHARACTERISTICS:
( A ) LENGTH: 748 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
            20                  25                  30

Leu Leu Ala Gln Trp Ile Glu Thr Gln Asp Trp Glu Val Ala Ser Asn
        35                  40                  45
```

-continued

```
Asn Glu Thr Met Ala Thr Ile Leu Leu Gln Asn Leu Leu Ile Gln Leu
     50                  55                  60

Asp Glu Gln Leu Gly Arg Val Ser Lys Glu Lys Asn Leu Leu Leu Ile
 65                  70                  75                      80

His Asn Leu Lys Arg Ile Arg Lys Val Leu Gln Gly Lys Phe His Gly
                 85                  90                  95

Asn Pro Met His Val Ala Val Val Ile Ser Asn Cys Leu Arg Glu Glu
            100                 105                 110

Arg Arg Ile Leu Ala Ala Ala Asn Met Pro Ile Gln Gly Pro Leu Glu
        115                 120                 125

Lys Ser Leu Gln Ser Ser Ser Val Ser Glu Arg Gln Arg Asn Val Glu
    130                 135                 140

His Lys Val Ser Ala Ile Lys Asn Ser Val Gln Met Thr Glu Gln Asp
145                 150                 155                     160

Thr Lys Tyr Leu Glu Asp Leu Gln Asp Glu Phe Asp Tyr Arg Tyr Lys
                165                 170                 175

Thr Ile Gln Thr Met Asp Gln Gly Asp Lys Asn Ser Ile Leu Val Asn
            180                 185                 190

Gln Glu Val Leu Thr Leu Leu Gln Glu Met Leu Asn Ser Leu Asp Phe
        195                 200                 205

Lys Arg Lys Glu Ala Leu Ser Lys Met Thr Gln Ile Val Asn Glu Thr
    210                 215                 220

Asp Leu Leu Met Asn Ser Met Leu Leu Glu Glu Leu Gln Asp Trp Lys
225                 230                 235                     240

Lys Arg His Arg Ile Ala Cys Ile Gly Gly Pro Leu His Asn Gly Leu
                245                 250                 255

Asp Gln Leu Gln Asn Cys Phe Thr Leu Leu Ala Glu Ser Leu Phe Gln
            260                 265                 270

Leu Arg Gln Gln Leu Glu Lys Leu Gln Glu Gln Ser Thr Lys Met Thr
        275                 280                 285

Tyr Glu Gly Asp Pro Ile Pro Ala Gln Arg Ala His Leu Leu Glu Arg
    290                 295                 300

Ala Thr Phe Leu Ile Tyr Asn Leu Phe Lys Asn Ser Phe Val Val Glu
305                 310                 315                     320

Arg His Ala Cys Met Pro Thr His Pro Gln Arg Pro Met Val Leu Lys
                325                 330                 335

Thr Leu Ile Gln Phe Thr Val Lys Leu Arg Leu Leu Ile Lys Leu Pro
            340                 345                 350

Glu Leu Asn Tyr Gln Val Lys Val Lys Ala Ser Ile Asp Lys Asn Val
        355                 360                 365

Ser Thr Leu Ser Asn Arg Arg Phe Val Leu Cys Gly Thr His Val Lys
    370                 375                 380

Ala Met Ser Ser Glu Glu Ser Ser Asn Gly Ser Leu Ser Val Glu Leu
385                 390                 395                     400

Asp Ile Ala Thr Gln Gly Asp Glu Val Gln Tyr Trp Ser Lys Gly Asn
                405                 410                 415

Glu Gly Cys His Met Val Thr Glu Glu Leu His Ser Ile Thr Phe Glu
            420                 425                 430

Thr Gln Ile Cys Leu Tyr Gly Leu Thr Ile Asn Leu Glu Thr Ser Ser
        435                 440                 445

Leu Pro Val Val Met Ile Ser Asn Val Ser Gln Leu Pro Asn Ala Trp
    450                 455                 460

Ala Ser Ile Ile Trp Tyr Asn Val Ser Thr Asn Asp Ser Gln Asn Leu
```

-continued 465 470 475 480

Val Phe Phe Asn Asn Pro Pro Ser Val Thr Leu Gly Gln Leu Leu Glu
485 490 495

Val Met Ser Trp Gln Phe Ser Ser Tyr Val Gly Arg Gly Leu Asn Ser
500 505 510

Glu Gln Leu Asn Met Leu Ala Glu Lys Leu Thr Val Gln Ser Asn Tyr
515 520 525

Asn Asp Gly His Leu Thr Trp Ala Lys Phe Cys Lys Glu His Leu Pro
530 535 540

Gly Lys Thr Phe Thr Phe Trp Thr Trp Leu Glu Ala Ile Leu Asp Leu
545 550 555 560

Ile Lys Lys His Ile Leu Pro Leu Trp Ile Asp Gly Tyr Ile Met Gly
565 570 575

Phe Val Ser Lys Glu Lys Glu Arg Leu Leu Leu Lys Asp Lys Met Pro
580 585 590

Gly Thr Phe Leu Leu Arg Phe Ser Glu Ser His Leu Gly Gly Ile Thr
595 600 605

Phe Thr Trp Val Asp Gln Ser Glu Asn Gly Glu Val Arg Phe His Ser
610 615 620

Val Glu Pro Tyr Asn Lys Gly Arg Leu Ser Ala Leu Ala Phe Ala Asp
625 630 635 640

Ile Leu Arg Asp Tyr Lys Val Ile Met Ala Glu Asn Ile Pro Glu Asn
645 650 655

Pro Leu Lys Tyr Leu Tyr Pro Asp Ile Pro Lys Asp Lys Ala Phe Gly
660 665 670

Lys His Tyr Ser Ser Gln Pro Cys Glu Val Ser Arg Pro Thr Glu Arg
675 680 685

Gly Asp Lys Gly Tyr Val Pro Ser Val Phe Ile Pro Ile Ser Thr Ile
690 695 700

Arg Ser Asp Ser Thr Glu Pro Gln Ser Pro Ser Asp Leu Leu Pro Met
705 710 715 720

Ser Pro Ser Ala Tyr Ala Val Leu Arg Glu Asn Leu Ser Pro Thr Thr
725 730 735

Ile Glu Thr Ala Met Asn Ser Pro Tyr Ser Ala Glu
740 745

( 2 ) INFORMATION FOR SEQ ID NO:11:

( i ) SEQUENCE CHARACTERISTICS:
( A ) LENGTH: 2869 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Mouse ( v i i ) IMMEDIATE SOURCE:
( A ) LIBRARY: splenic/thymic
( B ) CLONE: Murine 19sf6

( i x ) FEATURE:
( A ) NAME/KEY: CDS
( B ) LOCATION: 69..2378

( x i ) SEQUENCE DESCRIPTION: SEQ ID NO:11:

-continued

GCCGCGACCA GCCAGGCCGG CCAGTCGGGC TCAGCCCGGA GACAGTCGAG ACCCCTGACT 60

GCAGCAGG ATG GCT CAG TGG AAC CAG CTG CAG CAG CTG GAC ACA CGC TAC 110
Met Ala Gln Trp Asn Gln Leu Gln Gln Leu Asp Thr Arg Tyr
1 5 10

CTG AAG CAG CTG CAC CAG CTG TAC AGC GAC ACG TTC CCC ATG GAG CTG 158
Leu Lys Gln Leu His Gln Leu Tyr Ser Asp Thr Phe Pro Met Glu Leu
15 20 25 30

CGG CAG TTC CTG GCA CCT TGG ATT GAG AGT CAA GAC TGG GCA TAT GCA 206
Arg Gln Phe Leu Ala Pro Trp Ile Glu Ser Gln Asp Trp Ala Tyr Ala
35 40 45

GCC AGC AAA GAG TCA CAT GCC ACG TTG GTG TTT CAT AAT CTC TTG GGT 254
Ala Ser Lys Glu Ser His Ala Thr Leu Val Phe His Asn Leu Leu Gly
50 55 60

GAA ATT GAC CAG CAA TAT AGC CGA TTC CTG CAA GAG TCC AAT GTC CTC 302
Glu Ile Asp Gln Gln Tyr Ser Arg Phe Leu Gln Glu Ser Asn Val Leu
65 70 75

TAT CAG CAC AAC CTT CGA AGA ATC AAG CAG TTT CTG CAG AGC AGG TAT 350
Tyr Gln His Asn Leu Arg Arg Ile Lys Gln Phe Leu Gln Ser Arg Tyr
80 85 90

CTT GAG AAG CCA ATG GAA ATT GCC CGG ATC GTG GCC CGA TGC CTG TGG 398
Leu Glu Lys Pro Met Glu Ile Ala Arg Ile Val Ala Arg Cys Leu Trp
95 100 105 110

GAA GAG TCT CGC CTC CTC CAG ACG GCA GCC ACG GCA GCC CAG CAA GGG 446
Glu Glu Ser Arg Leu Leu Gln Thr Ala Ala Thr Ala Ala Gln Gln Gly
115 120 125

GGC CAG GCC AAC CAC CCA ACA GCC GCC GTA GTG ACA GAG AAG CAG CAG 494
Gly Gln Ala Asn His Pro Thr Ala Ala Val Val Thr Glu Lys Gln Gln
130 135 140

ATG TTG GAG CAG CAT CTT CAG GAT GTC CGG AAG CGA GTG CAG GAT CTA 542
Met Leu Glu Gln His Leu Gln Asp Val Arg Lys Arg Val Gln Asp Leu
145 150 155

GAA CAG AAA ATG AAG GTG GTG GAG AAC CTC CAG GAC GAC TTT GAT TTC 590
Glu Gln Lys Met Lys Val Val Glu Asn Leu Gln Asp Asp Phe Asp Phe
160 165 170

AAC TAC AAA ACC CTC AAG AGC CAA GGA GAC ATG CAG GAT CTG AAT GGA 638
Asn Tyr Lys Thr Leu Lys Ser Gln Gly Asp Met Gln Asp Leu Asn Gly
175 180 185 190

AAC AAC CAG TCT GTG ACC AGA CAG AAG ATG CAG CAG CTG GAA CAG ATG 686
Asn Asn Gln Ser Val Thr Arg Gln Lys Met Gln Gln Leu Glu Gln Met
195 200 205

CTC ACA GCC CTG GAC CAG ATG CGG AGA AGC ATT GTG AGT GAG CTG GCG 734
Leu Thr Ala Leu Asp Gln Met Arg Arg Ser Ile Val Ser Glu Leu Ala
210 215 220

GGG CTC TTG TCA GCA ATG GAG TAC GTG CAG AAG ACA CTG ACT GAT GAA 782
Gly Leu Leu Ser Ala Met Glu Tyr Val Gln Lys Thr Leu Thr Asp Glu
225 230 235

GAG CTG GCT GAC TGG AAG AGG CGG CCA GAG ATC GCG TGC ATC GGA GGC 830
Glu Leu Ala Asp Trp Lys Arg Arg Pro Glu Ile Ala Cys Ile Gly Gly
240 245 250

CCT CCC AAC ATC TGC CTG GAC CGT CTG GAA AAC TGG ATA ACT TCA TTA 878
Pro Pro Asn Ile Cys Leu Asp Arg Leu Glu Asn Trp Ile Thr Ser Leu
255 260 265 270

GCA GAA TCT CAA CTT CAG ACC CGC CAA CAA ATT AAG AAA CTG GAG GAG 926
Ala Glu Ser Gln Leu Gln Thr Arg Gln Gln Ile Lys Lys Leu Glu Glu
275 280 285

CTG CAG CAG AAA GTG TCC TAC AAG GGC GAC CCT ATC GTG CAG CAC CGG 974
Leu Gln Gln Lys Val Ser Tyr Lys Gly Asp Pro Ile Val Gln His Arg
290 295 300

CCC ATG CTG GAG GAG AGG ATC GTG GAG CTG TTC AGA AAC TTA ATG AAG 1022

-continued

Pro Met Leu Glu Glu Arg Ile Val Glu Leu Phe Arg Asn Leu Met Lys
305 310 315

AGT GCC TTC GTG GTG GAG CGG CAG CCC TGC ATG CCC ATG CAC CCG GAC 1070
Ser Ala Phe Val Val Glu Arg Gln Pro Cys Met Pro Met His Pro Asp
320 325 330

CGG CCC TTA GTC ATC AAG ACT GGT GTC CAG TTT ACC ACG AAA GTC AGG 1118
Arg Pro Leu Val Ile Lys Thr Gly Val Gln Phe Thr Thr Lys Val Arg
335 340 345 350

TTG CTG GTC AAA TTT CCT GAG TTG AAT TAT CAG CTT AAA ATT AAA GTG 1166
Leu Leu Val Lys Phe Pro Glu Leu Asn Tyr Gln Leu Lys Ile Lys Val
355 360 365

TGC ATT GAT AAA GAC TCT GGG GAT GTT GCT GCC CTC AGA GGG TCT CGG 1214
Cys Ile Asp Lys Asp Ser Gly Asp Val Ala Ala Leu Arg Gly Ser Arg
370 375 380

AAA TTT AAC ATT CTG GGC ACG AAC ACA AAA GTG ATG AAC ATG GAG GAG 1262
Lys Phe Asn Ile Leu Gly Thr Asn Thr Lys Val Met Asn Met Glu Glu
385 390 395

TCT AAC AAC GGC AGC CTG TCT GCA GAG TTC AAG CAC CTG ACC CTT AGG 1310
Ser Asn Asn Gly Ser Leu Ser Ala Glu Phe Lys His Leu Thr Leu Arg
400 405 410

GAG CAG AGA TGT GGG AAT GGA GGC CGT GCC AAT TGT GAT GCC TCC TTG 1358
Glu Gln Arg Cys Gly Asn Gly Gly Arg Ala Asn Cys Asp Ala Ser Leu
415 420 425 430

ATC GTG ACT GAG GAG CTG CAC CTG ATC ACC TTC GAG ACT GAG GTG TAC 1406
Ile Val Thr Glu Glu Leu His Leu Ile Thr Phe Glu Thr Glu Val Tyr
435 440 445

CAC CAA GGC CTC AAG ATT GAC CTA GAG ACC CAC TCC TTG CCA GTT GTG 1454
His Gln Gly Leu Lys Ile Asp Leu Glu Thr His Ser Leu Pro Val Val
450 455 460

GTG ATC TCC AAC ATC TGT CAG ATG CCA AAT GCT TGG GCA TCA ATC CTG 1502
Val Ile Ser Asn Ile Cys Gln Met Pro Asn Ala Trp Ala Ser Ile Leu
465 470 475

TGG TAT AAC ATG CTG ACC AAT AAC CCC AAG AAC GTG AAC TTC TTC ACT 1550
Trp Tyr Asn Met Leu Thr Asn Asn Pro Lys Asn Val Asn Phe Phe Thr
480 485 490

AAG CCG CCA ATT GGA ACC TGG GAC CAA GTG GCC GAG GTG CTC AGC TGG 1598
Lys Pro Pro Ile Gly Thr Trp Asp Gln Val Ala Glu Val Leu Ser Trp
495 500 505 510

CAG TTC TCG TCC ACC ACC AAG CGA GGG CTG AGC ATC GAG CAG CTG ACA 1646
Gln Phe Ser Ser Thr Thr Lys Arg Gly Leu Ser Ile Glu Gln Leu Thr
515 520 525

ACG CTG GCT GAG AAG CTC CTA GGG CCT GGT GTG AAC TAC TCA GGG TGT 1694
Thr Leu Ala Glu Lys Leu Leu Gly Pro Gly Val Asn Tyr Ser Gly Cys
530 535 540

CAG ATC ACA TGG GCT AAA TTC TGC AAA GAA AAC ATG GCT GGC AAG GGC 1742
Gln Ile Thr Trp Ala Lys Phe Cys Lys Glu Asn Met Ala Gly Lys Gly
545 550 555

TTC TCC TTC TGG GTC TGG CTA GAC AAT ATC ATC GAC CTT GTG AAA AAG 1790
Phe Ser Phe Trp Val Trp Leu Asp Asn Ile Ile Asp Leu Val Lys Lys
560 565 570

TAT ATC TTG GCC CTT TGG AAT GAA GGG TAC ATC ATG GGT TTC ATC AGC 1838
Tyr Ile Leu Ala Leu Trp Asn Glu Gly Tyr Ile Met Gly Phe Ile Ser
575 580 585 590

AAG GAG CGG GAG CGG GCC ATC CTA AGC ACA AAG CCC CCG GGC ACC TTC 1886
Lys Glu Arg Glu Arg Ala Ile Leu Ser Thr Lys Pro Pro Gly Thr Phe
595 600 605

CTA CTG CGC TTC AGC GAG AGC AGC AAA GAA GGA GGG GTC ACT TTC ACT 1934
Leu Leu Arg Phe Ser Glu Ser Ser Lys Glu Gly Gly Val Thr Phe Thr
610 615 620

TGG GTG GAA AAG GAC ATC AGT GGC AAG ACC CAG ATC CAG TCT GTA GAG 1982

-continued

Trp Val Glu Lys Asp Ile Ser Gly Lys Thr Gln Ile Gln Ser Val Glu
625 630 635

CCA TAC ACC AAG CAG CAG CTG AAC AAC ATG TCA TTT GCT GAA ATC ATC 2030
Pro Tyr Thr Lys Gln Gln Leu Asn Asn Met Ser Phe Ala Glu Ile Ile
640 645 650

ATG GGC TAT AAG ATC ATG GAT GCG ACC AAC ATC CTG GTG TCT CCA CTT 2078
Met Gly Tyr Lys Ile Met Asp Ala Thr Asn Ile Leu Val Ser Pro Leu
655 660 665 670

GTC TAC CTC TAC CCC GAC ATT CCC AAG GAG GAG GCA TTT GGA AAG TAC 2126
Val Tyr Leu Tyr Pro Asp Ile Pro Lys Glu Glu Ala Phe Gly Lys Tyr
675 680 685

TGT AGG CCC GAG AGC CAG GAG CAC CCC GAA GCC GAC CCA GGT AGT GCT 2174
Cys Arg Pro Glu Ser Gln Glu His Pro Glu Ala Asp Pro Gly Ser Ala
690 695 700

GCC CCG TAC CTG AAG ACC AAG TTC ATC TGT GTG ACA CCA ACG ACC TGC 2222
Ala Pro Tyr Leu Lys Thr Lys Phe Ile Cys Val Thr Pro Thr Thr Cys
705 710 715

AGC AAT ACC ATT GAC CTG CCG ATG TCC CCC CGC ACT TTA GAT TCA TTG 2270
Ser Asn Thr Ile Asp Leu Pro Met Ser Pro Arg Thr Leu Asp Ser Leu
720 725 730

ATG CAG TTT GGA AAT AAC GGT GAA GGT GCT GAG CCC TCA GCA GGA GGG 2318
Met Gln Phe Gly Asn Asn Gly Glu Gly Ala Glu Pro Ser Ala Gly Gly
735 740 745 750

CAG TTT GAG TCG CTC ACG TTT GAC ATG GAT CTG ACC TCG GAG TGT GCT 2366
Gln Phe Glu Ser Leu Thr Phe Asp Met Asp Leu Thr Ser Glu Cys Ala
755 760 765

ACC TCC CCC ATG TGAGGAGCTG AAACCAGAAG CTGCAGAGAC GTGACTTGAG 2418
Thr Ser Pro Met
770

ACACCTGCCC CGTGCTCCAC CCCTAAGCAG CCGAACCCCA TATCGTCTGA AACTCCTA 2478

TTTGTGGTTC CAGATTTTTT TTTTTAATTT CCTACTTCTG CTATCTTTGG GCAATCTG 2538

CACTTTTTAA AAGAGAGAAA TGAGTGAGTG TGGGTGATAA ACTGTTATGT AAAGAGGA 2598

GACCTCTGAG TCTGGGGATG GGGCTGAGAG CAGAAGGGAG GCAAAGGGGA ACACCTCC 2658

TCCTGCCCGC CTGCCCTCCT TTTTCAGCAG CTCGGGGGTT GGTTGTTAGA CAAGTGCC 2718

CTGGTGCCCA TGGCTACCTG TTGCCCCACT CTGTGAGCTG ATACCCCATT CTGGGAAC 2778

CTGGCTCTGC ACTTTCAACC TTGCTAATAT CCACATAGAA GCTAGGACTA AGCCCAGG 2838

GTTCCTCTTT AAATTAAAAA AAAAAAAAAA A 2869

( 2 ) INFORMATION FOR SEQ ID NO:12:

( i ) SEQUENCE CHARACTERISTICS:
( A ) LENGTH: 770 amino acids
( B ) TYPE: amino acid
( D ) TOPOLOGY: linear ( i i ) MOLECULE TYPE: protein ( x i ) SEQUENCE DESCRIPTION: SEQ ID NO:12:

Met Ala Gln Trp Asn Gln Leu Gln Gln Leu Asp Thr Arg Tyr Leu Lys
1 5 10 15

Gln Leu His Gln Leu Tyr Ser Asp Thr Phe Pro Met Glu Leu Arg Gln
20 25 30

Phe Leu Ala Pro Trp Ile Glu Ser Gln Asp Trp Ala Tyr Ala Ala Ser
35 40 45

Lys Glu Ser His Ala Thr Leu Val Phe His Asn Leu Leu Gly Glu Ile
50 55 60

Asp Gln Gln Tyr Ser Arg Phe Leu Gln Glu Ser Asn Val Leu Tyr Gln

-continued 65 70 75 80

His Asn Leu Arg Arg Ile Lys Gln Phe Leu Gln Ser Arg Tyr Leu Glu
85 90 95

Lys Pro Met Glu Ile Ala Arg Ile Val Ala Arg Cys Leu Trp Glu Glu
100 105 110

Ser Arg Leu Leu Gln Thr Ala Ala Thr Ala Ala Gln Gln Gly Gly Gln
115 120 125

Ala Asn His Pro Thr Ala Ala Val Val Thr Glu Lys Gln Gln Met Leu
130 135 140

Glu Gln His Leu Gln Asp Val Arg Lys Arg Val Gln Asp Leu Glu Gln
145 150 155 160

Lys Met Lys Val Val Glu Asn Leu Gln Asp Asp Phe Asp Phe Asn Tyr
165 170 175

Lys Thr Leu Lys Ser Gln Gly Asp Met Gln Asp Leu Asn Gly Asn Asn
180 185 190

Gln Ser Val Thr Arg Gln Lys Met Gln Gln Leu Glu Gln Met Leu Thr
195 200 205

Ala Leu Asp Gln Met Arg Arg Ser Ile Val Ser Glu Leu Ala Gly Leu
210 215 220

Leu Ser Ala Met Glu Tyr Val Gln Lys Thr Leu Thr Asp Glu Glu Leu
225 230 235 240

Ala Asp Trp Lys Arg Arg Pro Glu Ile Ala Cys Ile Gly Gly Pro Pro
245 250 255

Asn Ile Cys Leu Asp Arg Leu Glu Asn Trp Ile Thr Ser Leu Ala Glu
260 265 270

Ser Gln Leu Gln Thr Arg Gln Gln Ile Lys Lys Leu Glu Glu Leu Gln
275 280 285

Gln Lys Val Ser Tyr Lys Gly Asp Pro Ile Val Gln His Arg Pro Met
290 295 300

Leu Glu Glu Arg Ile Val Glu Leu Phe Arg Asn Leu Met Lys Ser Ala
305 310 315 320

Phe Val Val Glu Arg Gln Pro Cys Met Pro Met His Pro Asp Arg Pro
325 330 335

Leu Val Ile Lys Thr Gly Val Gln Phe Thr Thr Lys Val Arg Leu Leu
340 345 350

Val Lys Phe Pro Glu Leu Asn Tyr Gln Leu Lys Ile Lys Val Cys Ile
355 360 365

Asp Lys Asp Ser Gly Asp Val Ala Ala Leu Arg Gly Ser Arg Lys Phe
370 375 380

Asn Ile Leu Gly Thr Asn Thr Lys Val Met Asn Met Glu Glu Ser Asn
385 390 395 400

Asn Gly Ser Leu Ser Ala Glu Phe Lys His Leu Thr Leu Arg Glu Gln
405 410 415

Arg Cys Gly Asn Gly Gly Arg Ala Asn Cys Asp Ala Ser Leu Ile Val
420 425 430

Thr Glu Glu Leu His Leu Ile Thr Phe Glu Thr Glu Val Tyr His Gln
435 440 445

Gly Leu Lys Ile Asp Leu Glu Thr His Ser Leu Pro Val Val Val Ile
450 455 460

Ser Asn Ile Cys Gln Met Pro Asn Ala Trp Ala Ser Ile Leu Trp Tyr
465 470 475 480

Asn Met Leu Thr Asn Asn Pro Lys Asn Val Asn Phe Phe Thr Lys Pro
485 490 495

-continued

Pro Ile Gly Thr Trp Asp Gln Val Ala Glu Val Leu Ser Trp Gln Phe
500 505 510

Ser Ser Thr Thr Lys Arg Gly Leu Ser Ile Glu Gln Leu Thr Thr Leu
515 520 525

Ala Glu Lys Leu Leu Gly Pro Gly Val Asn Tyr Ser Gly Cys Gln Ile
530 535 540

Thr Trp Ala Lys Phe Cys Lys Glu Asn Met Ala Gly Lys Gly Phe Ser
545 550 555 560

Phe Trp Val Trp Leu Asp Asn Ile Ile Asp Leu Val Lys Lys Tyr Ile
565 570 575

Leu Ala Leu Trp Asn Glu Gly Tyr Ile Met Gly Phe Ile Ser Lys Glu
580 585 590

Arg Glu Arg Ala Ile Leu Ser Thr Lys Pro Pro Gly Thr Phe Leu Leu
595 600 605

Arg Phe Ser Glu Ser Ser Lys Glu Gly Gly Val Thr Phe Thr Trp Val
610 615 620

Glu Lys Asp Ile Ser Gly Lys Thr Gln Ile Gln Ser Val Glu Pro Tyr
625 630 635 640

Thr Lys Gln Gln Leu Asn Asn Met Ser Phe Ala Glu Ile Ile Met Gly
645 650 655

Tyr Lys Ile Met Asp Ala Thr Asn Ile Leu Val Ser Pro Leu Val Tyr
660 665 670

Leu Tyr Pro Asp Ile Pro Lys Glu Glu Ala Phe Gly Lys Tyr Cys Arg
675 680 685

Pro Glu Ser Gln Glu His Pro Glu Ala Asp Pro Gly Ser Ala Ala Pro
690 695 700

Tyr Leu Lys Thr Lys Phe Ile Cys Val Thr Pro Thr Thr Cys Ser Asn
705 710 715 720

Thr Ile Asp Leu Pro Met Ser Pro Arg Thr Leu Asp Ser Leu Met Gln
725 730 735

Phe Gly Asn Asn Gly Glu Gly Ala Glu Pro Ser Ala Gly Gly Gln Phe
740 745 750

Glu Ser Leu Thr Phe Asp Met Asp Leu Thr Ser Glu Cys Ala Thr Ser
755 760 765

Pro Met
770

( 2 ) INFORMATION FOR SEQ ID NO:13:

( i ) SEQUENCE CHARACTERISTICS:
( A ) LENGTH: 110 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:13:

Ser Leu Ala Ala Glu Phe Arg His Leu Gln Leu Lys Glu Gln Lys As
1 5 10 15

Ala Gly Thr Arg Thr Asn Glu Gly Pro Leu Ile Val Thr Glu Glu Le
20 25 30

His Ser Leu Ser Phe Glu Thr Gln Leu Cys Gln Pro Gly Leu Val Il
35 40 45

Asp Leu Glu Thr Thr Ser Leu Pro Val Val Val Ile Ser Asn Val Se
50 55 60

Gln Leu Pro Ser Gly Trp Ala Ser Ile Leu Trp Tyr Asn Met Leu Va
65 70 75 80

Ala Glu Pro Arg Asn Leu Ser Phe Phe Leu Thr Pro Pro Cys Ala Ar
85 90 95

Trp Ala Gln Leu Ser Glu Val Leu Ser Trp Gln Phe Ser Ser
100 105 110

( 2 ) INFORMATION FOR SEQ ID NO:14:

( i ) SEQUENCE CHARACTERISTICS:
( A ) LENGTH: 112 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:14:

Ser Leu Ser Ala Glu Phe Lys His Leu Thr Leu Arg Glu Gln Arg Cy
1 5 10 15

Gly Asn Gly Gly Arg Ala Asn Cys Asp Ala Ser Leu Ile Val Thr Gl
20 25 30

Glu Leu His Leu Ile Thr Phe Glu Thr Glu Val Tyr His Gln Gly Le
35 40 45

Lys Ile Asp Leu Glu Thr His Ser Leu Pro Val Val Val Ile Ser As
50 55 60

Ile Cys Gln Met Pro Asn Ala Trp Ala Ser Ile Leu Trp Tyr Asn Me
65 70 75 80

Leu Thr Asn Asn Pro Lys Asn Val Asn Phe Phe Thr Lys Pro Pro Il
85 90 95

Gly Thr Trp Asp Gln Val Ala Glu Val Leu Ser Trp Gln Phe Ser Se
100 105 110

( 2 ) INFORMATION FOR SEQ ID NO:15:

( i ) SEQUENCE CHARACTERISTICS:
( A ) LENGTH: 111 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:15:

Ser Leu Ser Val Glu Phe Arg His Leu Gln Pro Lys Glu Met Lys Cy
1 5 10 15

Ser Thr Gly Ser Lys Gly Asn Glu Gly Cys His Met Val Thr Glu Gl
20 25 30

Leu His Ser Ile Thr Phe Glu Thr Gln Ile Cys Leu Tyr Gly Leu Th
35 40 45

Ile Asn Leu Glu Thr Ser Ser Leu Pro Val Val Met Ile Ser Asn Va
50 55 60

Ser Gln Leu Pro Asn Ala Trp Ala Ser Ile Ile Trp Tyr Asn Val Se 65 70 75 80

Thr Asn Asp Ser Gln Asn Leu Val Phe Phe Asn Asn Pro Pro Ser Va
85 90 95

Thr Leu Gly Gln Leu Leu Glu Val Met Ser Trp Gln Phe Ser Ser
100 105 110

( 2 ) INFORMATION FOR SEQ ID NO:16:

( i ) SEQUENCE CHARACTERISTICS:
( A ) LENGTH: 107 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:16:

Thr Leu Ser Ala His Phe Arg Asn Met Ser Leu Lys Arg Ile Lys Ar
1 5 10 15

Ala Asp Arg Arg Gly Ala Glu Ser Val Thr Glu Glu Lys Phe Thr Va
20 25 30

Leu Phe Glu Ser Gln Phe Ser Val Gly Ser Asn Glu Leu Val Phe Gl
35 40 45

Val Lys Thr Leu Ser Leu Pro Val Val Val Ile Val His Gly Ser Gl
50 55 60

Asp His Asn Ala Thr Ala Thr Val Leu Trp Asp Asn Ala Phe Ala Gl
65 70 75 80

Pro Gly Arg Val Pro Phe Ala Val Pro Asp Lys Val Leu Trp Pro Gl
85 90 95

Leu Cys Glu Ala Leu Asn Met Lys Phe Lys Ala
100 105

( 2 ) INFORMATION FOR SEQ ID NO:17:

( i ) SEQUENCE CHARACTERISTICS:
( A ) LENGTH: 107 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:17:

Cys Cys Ser Ala Leu Phe Lys Asn Leu Leu Leu Lys Lys Ile Lys Ar
1 5 10 15

Cys Glu Arg Lys Gly Thr Glu Ser Val Thr Glu Glu Lys Cys Ala Va
20 25 30

Leu Phe Ser Ala Ser Phe Thr Leu Gly Pro Gly Lys Leu Pro Ile Gl
35 40 45

Leu Gln Ala Leu Ser Leu Pro Leu Val Val Ile Val His Gly Asn Gl
50 55 60

Asp Asn Asn Ala Lys Ala Thr Ile Leu Trp Asp Asn Ala Phe Ser Gl
65 70 75 80

Met Asp Arg Val Pro Phe Val Val Ala Glu Arg Val Pro Trp Glu Ly
85 90 95

Met Cys Glu Thr Leu Asn Leu Lys Phe Met Ala
100 105

( 2 ) INFORMATION FOR SEQ ID NO:18:

( i ) SEQUENCE CHARACTERISTICS:
( A ) LENGTH: 111 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:18:

Leu Ile Trp Asp Phe Gly Tyr Leu Thr Leu Val Glu Gln Arg Ser Gl
1 5 10 15

Gly Ser Gly Lys Gly Ser Asn Lys Gly Pro Leu Gly Val Thr Glu Gl
20 25 30

Leu His Ile Ile Ser Phe Thr Val Lys Tyr Thr Tyr Gln Gly Leu Ly
35 40 45

Gln Glu Leu Lys Thr Asp Thr Leu Pro Val Val Ile Ile Ser Asn Me
50 55 60

Asn Gln Leu Ser Ile Ala Trp Ala Ser Val Leu Trp Phe Asn Leu Le
65 70 75 80

Ser Pro Asn Leu Gln Asn Gln Gln Phe Phe Ser Asn Pro Pro Lys Al
85 90 95

Pro Trp Ser Leu Leu Gly Pro Ala Leu Ser Trp Gln Phe Ser Ser
100 105 110

( 2 ) INFORMATION FOR SEQ ID NO:19:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:19:

CAGTTCCCGT CAATCAT 17

( 2 ) INFORMATION FOR SEQ ID NO:20:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:20:

CATTTCCCGT AAATCAT 17

( 2 ) INFORMATION FOR SEQ ID NO:21:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:21:

A T A T T C C T G T A A G T G A T 1 7

( 2 ) INFORMATION FOR SEQ ID NO:22:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:22:

G T A T T T C C C A G A A A A G G 1 7

( 2 ) INFORMATION FOR SEQ ID NO:23:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:23:

G T T G T T C C G G G A A A A T T 1 7

( 2 ) INFORMATION FOR SEQ ID NO:24:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:24:

T A T T T C C G G G A A A T C C C 1 7

( 2 ) INFORMATION FOR SEQ ID NO:25:

( i ) SEQUENCE CHARACTERISTICS:

-continued ( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:25:

T T C C C G G A A 9

( 2 ) INFORMATION FOR SEQ ID NO:26:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:26:

T T C C G G G A A 9

( 2 ) INFORMATION FOR SEQ ID NO:27:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:27:

T T C C G G G A A 9

( 2 ) INFORMATION FOR SEQ ID NO:28:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:28:

T T C C C G T A A 9

( 2 ) INFORMATION FOR SEQ ID NO:29:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:29:

T T C C C G T C A 9

( 2 ) INFORMATION FOR SEQ ID NO:30:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:30:

T T C C T G T A A 9

( 2 ) INFORMATION FOR SEQ ID NO:31:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:31:

T T C C C A G A A 9

( 2 ) INFORMATION FOR SEQ ID NO:32:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:32:

T T A C T C T A A 9

( 2 ) INFORMATION FOR SEQ ID NO:33:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:33:

T T A C T A T A A 9

( 2 ) INFORMATION FOR SEQ ID NO:34:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:34:

T T C T C A G A A 9

( 2 ) INFORMATION FOR SEQ ID NO:35:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:35:

T T C C C C G A A 9

( 2 ) INFORMATION FOR SEQ ID NO:36:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:36:

T T C T C G G A A 9

( 2 ) INFORMATION FOR SEQ ID NO:37:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:37:

TTCCCGTAA                                                                                                                      9

( 2 ) INFORMATION FOR SEQ ID NO:38:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:38:

TTCCCAGAA                                                                                                                      9

( 2 ) INFORMATION FOR SEQ ID NO:39:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:39:

Gly Ile Tyr Thr Glu Lys
            5

FUNCTIONALLY ACTIVE REGIONS OF SIGNAL TRANSDUCER AND ACTIVATOR OF TRANSCRIPTION

This Application is a Continuation, of application Ser. No. 08/369,796 filed Jan. 6, 1995, U.S. Pat. No. 5,716,622.

The research leading to the present invention was supported by National Institute of Health Grant Nos. AI34420 and AI32489. Accordingly, the Government may have certain rights in the invention.

FIELD OF THE INVENTION

The present invention relates generally to intracellular receptor recognition proteins or factors, termed Signal Transducers and Activators of Transcription (STAT), to methods and compositions utilizing such factors, and to the antibodies reactive toward them, in assays and for diagnosing, preventing and/or treating cellular debilitation, derangement or dysfunction. More particularly, the present invention relates to particular functional domains of molecules that exhibit both receptor recognition and message delivery via DNA binding in receptor-ligand specific manner, i.e., that directly participate both in the interaction with the ligand-bound receptor at the cell surface and in the activity of transcription in the nucleus as a DNA binding protein. The invention likewise relates to the antibodies and other entities that are specific to the functional domain of a STAT protein and that would thereby selectively modulate its activity.

BACKGROUND OF THE INVENTION

The STAT proteins have the dual purpose of, first, signal transduction from ligand-activated receptor kinase complexes followed by nuclear translocation and DNA binding to activate transcription (Darnell et al., 1994, Science 264:1415–1421). To function as specific transcriptional activators, STAT proteins by themselves or in combination with other proteins must have the ability to recognize specific DNA sequence elements in the promoters of their target genes. The binding of the STATs to DNA occurs only after tyrosine phosphorylation when the proteins form either homodimers (Shuai et al., 1994, Cell 76:821–828) or heterodimers (Schindler et al., 1992, Science 257:809–815: Zhong et al., 1994, Proc. Natl. Acad. Sci. USA 91:4806–4810; Zhong et al., 1994. Science 264:95–98) that bind DNA either alone or in combination with other proteins (Fu et al., 1990, Proc. Natl. Acad. Sci. USA 87:8555–8559; Schindler et al., 1992, Science 257:809–815). Since a number of mutations in the STAT proteins block phosphorylation and thus dimerization (Shuai et al., Science 261:1744–1746; Improta et al., 1994, Proc. Natl. Acad. Sci. USA 91:4776–4780), and none of the STAT sequences resembles previously well-defined DNA binding domains in other proteins, it has not been possible to quickly and easily define the DNA binding domains of the STATs.

U.S. Ser. No. 07/980,498, filed Nov. 23, 1992 now abandoned, which is a Continuation-In-Part of copending U.S. Ser. No. 07/854,296, filed Mar. 19, 1992 now abandoned, and International Patent Publication No. WO 93/19179 (published 30 Sep. 1993, by James E. Darnell, Jr. et al.) (each of which is hereby incorporated by reference in its entirety) disclosed the existence of receptor recognition factors, now termed signal transducers and activators of transcription (STAT). The nucleotide sequences of cDNA encoding receptor recognition factors having molecular weights of 113 kD (i.e., 113 kD protein, Stat113, or Stat2), 91 kD (i.e., 91 kD protein, Stat91, or Stat1α) and 84 kD (i.e., 84 kD protein, Stat84, or Stat1β) are reiterated herein in SEQ ID NOS:1, 3, and 5, respectively: the corresponding deduced amino acid sequences of the STAT proteins are shown in SEQ ID NOS:2, 4, and 6, respectively. Stat84 was found to be a truncated form of Stat91. There is 42% amino acid sequence similarity between Stat113 and Stat91/84 in an overlapping 715 amino acid sequence, including four leucine and one valine heptad repeats in the middle helix region, and several tyrosine residues were conserved near the ends of both proteins. The receptor recognition proteins thus possess multiple properties, among them: 1) recognizing and being activated during such recognition by receptors; 2) being translocated to the nucleus by an inhibitable process (e.g., NaF inhibits translocation); and 3) combining with transcription activating proteins or acting themselves as transcription activation proteins, and that all of these properties are possessed by the proteins described herein. In particular, the proteins are activated by binding of interferons to receptors on cells, in particular interferon-α (all three Stat proteins) and interferon-γ (Stat91).

U.S. application Ser. No. 08/126,595, filed Sep. 24, 1993 now abandoned, which is incorporated herein by reference in its entirety, relates to identification of functional sites of Stat1α, particularly identification of tyrosine-701 as the phosphorylation site, and the presence of a functional SH2 domain in the protein. This application further disclosed a murine Stat1 homolog (the nucleotide sequence is shown in SEQ ID NO:7; the amino acid sequence is shown in SEQ ID NO:8). Stat1 was further found to be active as a homodimer (Stat1α—Stat1α, Stat1α-Statβ, and Statβ—Statβ) (U.S. application Ser. No. 08/212,184, filed Mar. 11, 1994, which is incorporated herein by reference in its entirety). Additional Stat proteins, Stat3 (nucleotide sequence in SEQ ID NO:9 and amino acid sequence in SEQ ID NO:10) and Stat4 (nucleotide sequence in SEQ ID NO:11 and amino acid sequence in SEQ ID NO:12), were disclosed and characterized in U.S. applications Ser. No. 08/126,588, filed Sep. 24, 1993 now abandoned, and Ser. No. 08/212,185, filed Mar. 11, 1994 co-pending, each of which is incorporated herein by reference in its entirety.

SUMMARY OF THE INVENTION

In its broadest aspect, the present invention is related to the identification of a specific region on a STAT protein associated with activation of transcription. In particular, the present invention relates to the DNA-binding domain of a STAT protein, and to a serine phosphorylation site of a STAT protein. Of particular interest are the STAT proteins Stat1α (SEQ ID NOS:4 and 8), Stat1β (SEQ ID NO:6), Stat2 (SEQ ID NO:2), Stat3 (SEQ ID NO:10), and Stat4 (SEQ ID NO:12).

Accordingly, in a first aspect, the invention is directed to a peptide, which peptide consists of no more than about 110 amino acid residues and has an amino acid sequence corresponding to the sequence of the same number of amino acid residues from a DNA-binding domain of a STAT protein. In particular, the DNA-binding domain is in the region from amino acid residue 400 to amino acid residue 510 of the STAT protein. In a specific embodiment, the region from amino acid residue 400 to amino acid residue 510 of the STAT protein has an amino acid sequence selected from the group consisting of:

SLAAEFRHLQLKEQKNAGTRTNEGPLIV-TEELHSLSFETQLCQPGLVIDLETT SLPVVVISN-VSQLPSGWASILWYNMLVAEPRNLSF-FLTPPCARWAQLSEVLSWQFSS (SEQ ID NO:13)

SLSAEFKHLTLREQRCGNGGRANC-DASLIVTEELHLITFETEVYHQGLKIDLE THSLPV-VVISNICQMPNAWASILWYNMLTNNPKN-VNFFTKPPIGTWDQVAEVLSWQFSS (SEQ ID NO:14)

SLSVEFRHLQPKEMKCSTGSKGNEGCHM-VTEELHSITFETQICLYGLTINLET SSLPVVMISN-VSQLPNAWASIIWYNVSTNDSQNLVFFN-NPPSVTLGQLLEVMSWQFSS (SEQ ID NO:15)

TLSAHFRNMSLKRIKRADRRGAESV-TEEKFTVLFESQFSVGSNELVFQVKTLS LPV-VVIVHGSQDHNATATVL-WDNAFAEPGRVPFAVPDKVLWPQLCEALNMKFKA (SEQ ID NO:16)

CCSALFKNLLLKKIKRCERKGTESV-TEEKCAVLFSASFTLGPGKLPIQLQALS LPLVVIVH-GNQDNNAKATILWDNAFSEMDRVPFV-VAERVPWEKMCETLNLKFMA (SEQ ID NO:17)

LIWDFGYLTLVEQRSGGSGKGSNKG-PLGVTEELHIISFTVKYTYQGLKQELKT DTLPVVI-ISNMNQLSIAWASVLWFNLLSPNLQN-QQFFSNPPKAPWSLLGPALSWQFSS (SEQ ID NO:18)

In a further embodiment, the invention relates to a chimeric protein containing a STAT DNA-binding domain. In a specific embodiment, the chimeric protein is a second STAT protein in which the wild-type DNA-binding domain is substituted with the DNA-binding domain from the STAT protein.

The invention further provides antibodies specific for the DNA binding domain of a Stat protein, and methods for generating such antibodies. Accordingly, the invention is further directed to an immunogenic composition comprising the peptide described above in an admixture with an adjuvant. In a specific aspect, the peptide is conjugated to a carrier molecule. A method for generating an antibody to a DNA-binding domain of a STAT protein comprises immunizing an animal with the immunogenic composition.

In a related aspect the invention is directed to an antagonist of a STAT protein for binding to DNA, which antagonist is a compound capable of binding to a DNA-binding domain on a STAT protein. More particularly, the DNA-binding domain is in the region from amino acid residue 400 to amino acid residue 510 of the STAT protein. In a specific embodiment, the region from amino acid residue 400 to amino acid residue 510 of the STAT protein has an amino acid sequence selected from the group consisting of:

SLAAEFRHLQLKEQKNAGTRTNEGPLIV-TEELHSLSFETQLCQPGLVIDLETT SLPVVVISN-VSQLPSGWASILWYNMLVAEPRNLSF-FLTPPCARWAQLSEVLSWQFSS (SEQ ID NO:13)

SLSAEFKH LTLREQRCGNGGRANCDASLIVTEELHL-ITFETEVYHQGLKIDLE THSLPVVVISNICQMPNA-WASILWYNMLTNNPKNVNFFTKP-PIGTWDQVAEVLSWQFSS (SEQ ID NO:14)

SLSVEFRHLQPKEMKCSTGSKGNEGCHM-VTEELHSITFETQICLYGLTINLET SSLPVVMISN-VSQLPNAWASIIWYNVSTNDSQNLVFFN-NPPSVTLGQLLEVMSWQFSS (SEQ ID NO:15)

TLSAHFRNMSLKRIKRADRRGAESV-TEEKFTVLFESQFSVGSNELVFQVKTLS LPV-VVIVHGSQDHNATATVL-WDNAFAEPGRVPFAVPDKVLWPQLCEALNMKFKA (SEQ ID NO:16)

CCSALFKNLLLKKIKRCERKGTESV-TEEKCAVLFSASFTLGPGKLPIQLQALS LPLVVIVH-GNQDNNAKATILWDNAFSEMDRVPFV-VAERVPWEKMCETLNLKFMA (SEQ ID NO:17)

LIWDFGYLTLVEQRSGGSGKGSNKG-PLGVTEELHIISFTVKYTYQGLKQELKT DTLPVVI-ISNMNQLSIAWASVLWFNLLSPNLQN-QQFFSNPPKAPWSLLGPALSWQFSS (SEQ ID NO:18)

In specific aspects, the antagonist is selected from the group consisting of a peptide and an antibody. In particular, the antibody may be selected from the group consisting of a polyclonal antibody, a monoclonal antibody, a single chain antibody, an $F(ab')_2$ fragment of an immunoglobulin, an F(ab') fragment of an immunoglobulin, an Fv fragment of an immunoglobulin, and an Fab fragment of an immunoglobulin.

The invention further provides a method for identifying any chemical compound that is an antagonist of a STAT protein for binding to DNA. The method comprises contacting a biological sample containing the STAT protein and an oligonucleotide probe to which the STAT protein binds with a candidate compound, e.g., by mixing the putative inhibitor with the STAT protein and the oligonucleotide, and detecting whether the level of binding of the STAT protein to the probe is decreased relative to the level of binding of the STAT protein to the probe in a control biological sample. According to the invention, a decrease in the level of binding of the level of binding of the STAT protein to the probe indicates that the candidate is an antagonist of binding of the STAT protein to DNA.

Preferably, the compound under test would be capable of binding to or directly interacting with a DNA-binding domain on the STAT protein. Binding to a DNA-binding domain on the STAT protein can be tested, for example, by detecting binding of the compound to the peptide corresponding to the DNA-binding domain, as described above, or by detecting specific binding to a chimeric protein, such as (and preferably) a STAT protein in which the wild-type DNA-binding domain is substituted with a DNA-binding domain from a different STAT protein. More particularly, the DNA-binding domain is in the region from amino acid residue 400 to amino acid residue 510 of the STAT protein. In a specific embodiment, the region from amino acid residue 400 to amino acid residue 510 of the STAT protein has an amino acid sequence as set forth above.

In a specific embodiment, the candidate antagonist compound is a compound from a combinatorial library. In a further specific embodiment, the candidate compound is selected from the group consisting of a peptide and an antibody.

The invention further extends to a method for inhibiting signal transduction and activation of transcription mediated by a STAT protein comprising introducing a STAT protein having a mutation in the DNA-binding domain into a cell, whereby binding of a ligand to a receptor associated with the STAT protein leads to activation of the mutant form of the STAT protein which binds DNA with reduced affinity compared to the wild-type protein. As noted above, more particularly the DNA-binding domain is in the region from amino acid residue 400 to amino acid residue 510 of the STAT protein. In a specific embodiment, the region from amino acid residue 400 to amino acid residue 510 of the STAT protein has an amino acid sequence set forth above.

The mutation in the STAT protein may be selected from the group consisting of mutation of at least one glutamic acid residue corresponding to glutamic acid-434 or glutamic acid residue-435 of Stat1 or Stat3, and mutation of at least one valine residue corresponding to valine-461, valine-462, or valine-463 of Stat1 or Stat3. In a specific embodiment, exemplified infra, the mutation is of amino acids corresponding to glutamic acid-434 and glutamic acid-435 of Stat1 or Stat3, in particular substitution of alanine for glutamic acid in each residue.

The present invention relates to transgenic treatment for inhibiting signal transduction and activation of transcription mediated by a STAT protein. For example, the mutant STAT protein may be introduced into the cell by introducing a gene encoding the mutant STAT protein operatively associated with an expression control sequence for expression in the cell, whereby the mutant STAT protein is expressed by the cell. The gene may be introduced to cells in vivo or ex vivo.

In another aspect, the invention provides a method for inhibiting signal transduction and activation of transcription mediated by a STAT protein comprising introducing an antagonist of binding of a STAT protein to DNA, whereby binding of a ligand to a receptor associated with the STAT protein leads to activation of the STAT protein, which binds DNA with reduced affinity compared to the wild-type protein. The antagonist may be selected from the group consisting of a peptide and an antibody. For example, the antagonist may be an antibody selected from the group consisting of a polyclonal antibody, a monoclonal antibody, a single chain antibody, an $F(ab')_2$ fragment of an immunoglobulin, an F(ab') fragment of an immunoglobulin, an Fv fragment of an immunoglobulin, and an Fab fragment of an immunoglobulin.

In a further aspect, the invention further relates to the amplification of transcription activation that results from phosphorylation of a C-terminal serine residue of a STAT protein, which serine phosphorylation is not specific for receptor-binding, but relates to the state of cellular activation, i.e., the activity of serine kinases in the cell. Accordingly, the invention provides a method for inhibiting signal transduction and activation of transcription mediated by a STAT protein in response to binding of a ligand to a specific receptor for the ligand comprising introducing a STAT protein having a mutation in the serine phosphorylation site into a cell, whereby binding of the ligand to a receptor associated with the STAT protein leads to partial activation of the mutant form of the STAT protein which has reduced transcriptional activation capacity compared to the wild-type STAT protein. Preferably, the transcription activation capacity is reduced to 20% of the activity of the wild-type STAT protein. In a specific embodiment, relating to transgenic treatment, the mutant STAT protein is introduced into the cell by introducing a gene encoding the mutant STAT protein operatively associated with an expression control sequence for expression in the cell, whereby the mutant STAT protein is expressed by the cell. For example, the gene may be introduced to cells in vivo or ex vivo. In a specific embodiment, the STAT protein is Stat1α and the ligand is interferon-γ. In another specific embodiment, the STAT protein is Stat3 and the ligand is interleukin-6 (IL-6) or epidermal growth factor (EGF).

In a related aspect, the invention provides a method for detecting the level of activation of a STAT protein in a biological sample as a result of binding of ligand to a specific receptor for ligand comprising detecting the presence of a phosphorylated tyrosine residue and the presence of a phosphorylated serine residue on the STAT protein. Phosphorylation of tyrosine only is indicative of low level specific activation of the STAT protein; phosphorylation of serine only is indicative of general activation of the cell, but not of activation of the STAT protein; and phosphorylation of both tyrosine and serine is indicative of maximal activation of the STAT protein. In a specific embodiment, the STAT protein is Stat1α and the ligand is interferon-γ. In another specific embodiment, the STAT protein is Stat3 and the ligand is interleukin-6 (IL-6) or epidermal growth factor (EGF). In a specific aspect, the activation is associated with a disease or disorder selected from the group consisting of oncogenesis, inflammation, autoimmunity, infection, and the presence of a parasite.

Accordingly, it is a principal object of the present invention to provide a novel domain or region associated with activation of transcription activity of the family of STAT proteins.

Is a particular object of the invention to provide compound that inhibit DNA-binding binding and transcription activation activities of the factors.

It is a further object of the present invention to provide antibodies to the STAT protein domains, particularly the DNA-binding domain and the serine phosphorylation site, and methods for their preparation, including recombinant means.

It is a further object of the present invention to provide a method for detecting the presence of the STAT protein phosphorylated on tyrosine and on serine, in mammals in which invasive, spontaneous, or idiopathic pathological states are suspected to be present.

It is a further object of the present invention to provide a method and associated assay system for screening substances such as drugs, agents and the like, potentially effective in combating the adverse effects of the recognition factor and/or its subunits in mammals.

It is a still further object of the present invention to provide a method for the treatment of mammals to control the amount or activity of the recognition factor or subunits thereof, so as to alter the adverse consequences of such presence or activity, or where beneficial, to enhance such activity, of the STAT protein.

It is a still further object of the present invention to provide a method for the treatment of mammals to control the amount or activity of the recognition factor or its subunits, so as to treat or avert the adverse consequences of invasive, spontaneous or idiopathic pathological states.

It is a still further object of the present invention to provide pharmaceutical compositions for use in therapeutic methods which comprise or are based upon the recognition factor, its subunits, their binding partner(s), or upon agents or drugs that control the production, or that mimic or antagonize the activities of the recognition factors.

Other objects and advantages will become apparent to those skilled in the art from a review of the ensuing description which proceeds with reference to the following illustrative drawings.

BRIEF DESCRIPTION OF THE DRAWINGS

FIG. 1C depicts the Electrophoretic Mobility Shift Assay (EMSA) with Labeled Stat1 and Stat3 Consensus Site Oligonucleotides. A radio labelled probe that corresponds either to the Stat1 (S1) or Stat3 (S3) consensus sites was incubated with HepG2 nuclear extracts of cells that were untreated (−) or treated (+) with IL6. Positions of SIF A SIF B and SIF C complexes are marked. Supershifting of the IL6-induced complexes with Stat1 (1C) or Stat3 (3C) specific antisera is indicated above the lanes. Probes are identified above the lanes. (*) Indicates the position of the constitutive comigrating band described in the text.

FIGS. 6A–6B Alignment of STAT Family Members in the Putative DNA Binding Region. Lines below indicate boundaries of putative helices (H,h) and beta sheets (B,b) predicted by the algorithms of Chou and Fasman for each of the family members. Numbering above the alignment refers to the Stat1 sequence. The conserved amino acids mutated in this study are overlined. Sequences were aligned using the GCG pileup program and secondary structure was predicted using the GCG peptide structure program (Genetics Computer Group, 1991).

FIGS. 10A–10L. Protein extracts were prepared, exposed to anti-Stat1C serum and the 91 kDa $^{32}$P-labeled band was detected by PAGE analysis. (FIG. 10A). Autoradiongraphs of two dimensional thin layer chromatograms of trypsin digested wild type and mutant Stat1α from U3-cellular extracts treated or not treated with IFN-γ (FIGS. 10B–10L).

FIG. 12A depicts the Northern blot analysis for IRF1 mRNA, an INF-γ-induced gene, in U3A-derived cell lines containing wild type Stat1α or mutant Stat1αs treated with INF-γ. FIG. 12B shows the comparison of the run-on transcriptional signal from the IRF1 gene in the two U3A cell derivatives.

DETAILED DESCRIPTION

Figure 1A:
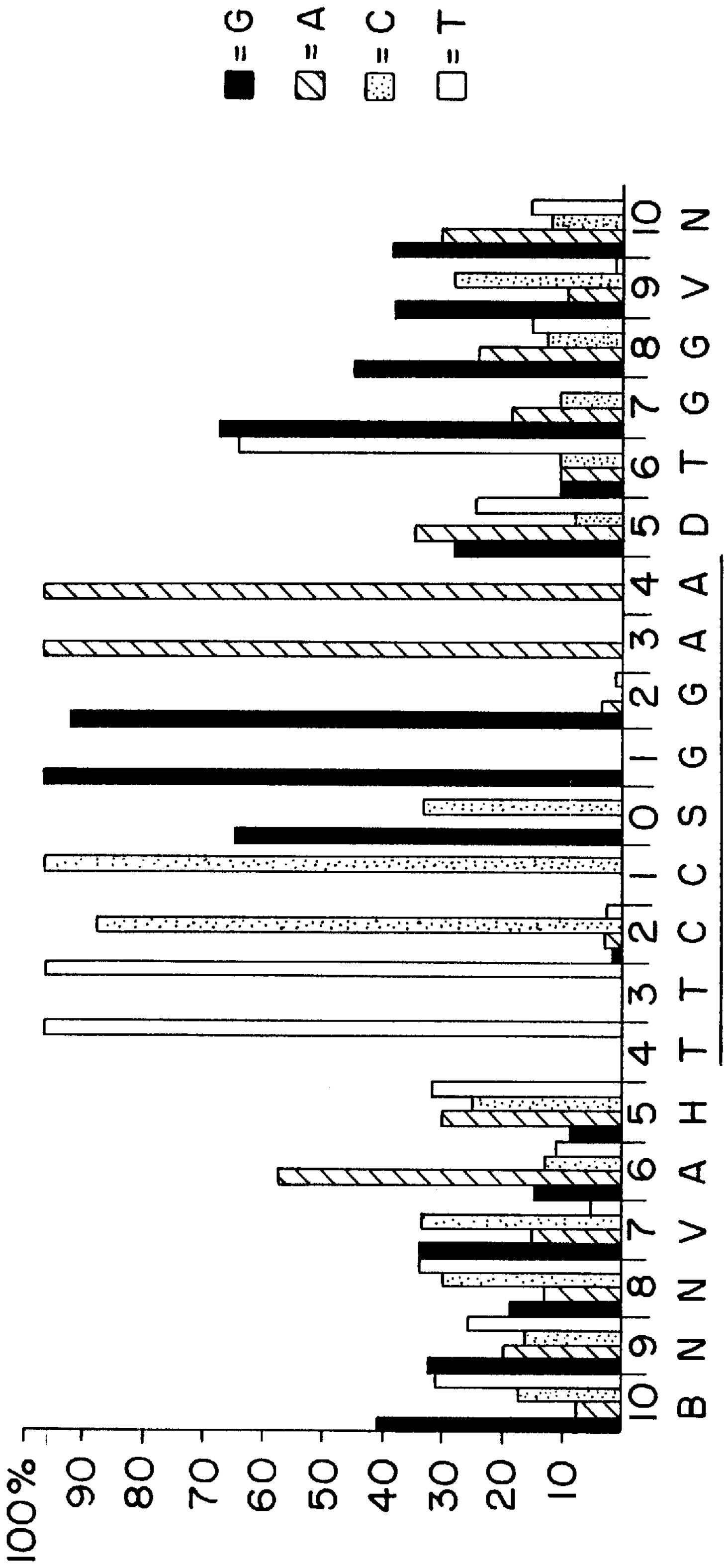
FIGS. 1A–1C FIGS. 1A–1B show the Binding Site Selection for Stat1 and Stat3. Graphical representation of the nucleotide frequency in 55 independent binding sites selected by Stat1 (FIG. 1A) and Stat3 (FIG. 1B) in vitro from a pool of random oligodeoxynucleotides. Sequences were aligned to fit the TTNNNNNAA consensus previously recognized to be present in natural GAS elements (Table 1). The common core consensus is underlined with the central nucleotide assigned position zero. The optimum consensus sequence and base preference in the flanking region is written beneath the graphs in I.U.B. code. N=G,C, AT,T; D=G,A,T; H=A,C,T; S=G,C; K=G,T; B=G,C,T; V=G,A,C; R=G,A.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning; A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984): F. M. Ausubel et al. (eds.), *Current Protocols in Molecular Biology*, John Wiley & Sons, Inc. (1994).

Therefore if appearing herein, the following terms shall have the definitions set out below.

The terms "receptor recognition factor", "receptor recognition-tyrosine kinase factor", "receptor recognition factor/tyrosine kinase substrate", "receptor recognition/transcription factor", "recognition factor", "recognition factor protein(s)", "signal transducers and activators of transcription", "STAT", and any variants not specifically listed, may be used herein interchangeably, and as used throughout the present application and claims refer to proteinaceous material including single or multiple proteins, and extends to those proteins having the amino acid sequence data described herein and presented in SEQ ID NOS:2, 4, 6, 8, 10, and 12. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "receptor recognition factor", "recognition factor", "recognition factor protein(s)", "signal transducers and activators of transcription", and "STAT" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH2 refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOL | | |
| --- | --- | --- |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine: "RNA molecules") or deoxyribonucleosides (deoxyadenosine, deoxyguanosine, deoxythymidine, or deoxycytidine; "DNA molecules") in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra. 11.7–11.8). Preferably a minimum length for a hybridizable nucleic acid is at least about 10 nucleotides; more preferably at least about 15 nucleotides; most preferably the length is at least about 20 nucleotides.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "oligonucleotide", as used herein in referring to the probe of the present invention, is defined as a molecule comprised of two or more ribonucleotides or deoxyribonucleotides, preferably more than three. Its exact size will depend upon many factors which, in turn, depend upon the ultimate function and use of the oligonucleotide.

A "nucleotide probe" as used herein refers to an oligonucleotide of at least about 9 bases, which has a sequence corresponding to a portion of the DNA to which a STAT protein binds, and thus is capable of binding to a STAT protein. Preferably, a nucleotide probe binds to the STAT protein with high specificity and affinity. Such a nucleotide probe corresponds to a specific STAT binding site. However, nucleotide probes of the invention may correspond to a general STAT binding site on DNA as well.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra).

Two DNA sequences are "substantially homologous" or "substantially similar" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, two amino acid sequences are "substantially homologous" or "substantially similar" when greater than 70% of the amino acids are identical, or functionally identical. Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. For example, as demonstrated in FIG. 6A–6B, infra, the sequences of the DNA-binding domains of the STAT proteins can be aligned, and the corresponding amino acid residues determined, despite the deletion of amino acid residues at some positions in one STAT protein compared to another. Thus, the term "corresponding to" refers to the sequence similarity, and not the numbering of the amino acid residues or nucleotide bases.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. An "antibody combining site" or "antigen recognition site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein. The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen: e.g., a bispecific (chimeric) monoclonal antibody.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed*., 1984, Benjamin/Cummings: Menlo Park, Calif. p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (*bacille Calmette-Guerin*) and *Corynebacterium parvum*. Preferably, the adjuvant is pharmaceutically acceptable.

A composition comprising "A" (where "A" is a single protein, DNA molecule. vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition. which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The term "biological sample" is used herein to refer to a sample containing cells that express or may express a STAT protein. Such cells may be obtained from a subject, or from in vitro culture. The term "biological sample" further extends to an extract of cells from either source.

The term "about" is used herein to mean within a 10% variance from the figure given, preferably within a 5% variance, and more preferably within a 1% variance.

As noted above, the present invention relates to the discovery that Stat1 and Stat3, which are two members of the ligand-activated transcription factor family that serve the dual functions of signal transducers and activators of transcription, select similar, but not identical, optimum binding sites from random oligonucleotides. Differences in their binding affinity were readily apparent with natural STAT binding sites. However, unlike other DNA binding proteins, fragments of the STAT proteins could not be shown to bind to DNA.

To take advantage of the different affinities for specific DNA sequences, chimeric Stat1:Stat3 molecules were used to locate the amino acids that could discriminate a general binding site from a specific binding site. The amino acids between residues ~400 and ~500 of these ~750 amino acid long proteins were discovered to determine the DNA binding site specificity. Mutations within this region result in Stat proteins which are activated normally by tyrosine phosphorylation and which dimerize, but have greatly reduced DNA binding affinities.

The invention further relates to the discovery that phosphorylation of a serine residue at position 727, in the carboxyl-terminus, of Stat1α is required for maximal interferon-γ (IFN-γ) dependent transcriptional response. This observation has important implications for the detection of the level of activation of a cell, based on activation of a STAT protein. Moreover, this observation provides the first link between ligand activated STATs and serine kinases in transcriptional control.

The present invention particularly relates to functionally active regions of the STAT proteins, e.g., as exemplified herein with portions of Stat1α, particularly such fragments that contain a DNA binding domain, and a C-terminal serine residue that is phosphorylated non-specifically as a consequence of cellular activation, but which is critical for maximum transcriptional activation.

The invention contemplates antagonists of STAT proteins targeted to the DNA-binding domain. In another aspect, the invention is directed to mutant forms of STAT proteins that can compete as substrates for tyrosine phosphorylation and dimerization, but which are poor DNA-binding proteins, or have reduced transcriptional activation activity.

Subsequent to the filing of the initial patent applications directed to the present invention, the inventors have termed each member of the family of receptor recognition factors as a signal transducer and activator of transcription (STAT) protein. Each STAT protein is designated by the apparent molecular weight (e.g., Stat113, Stat91, Stat84, etc.), or by the order in which it has been identified (e.g., Stat1α [Stat91], Stat1β [Stat84], Stat2 [Stat113], Stat3 [a murine protein also termed 19sf6], and Stat4 [a murine STAT protein also termed 13sf1]). As will be readily appreciated by one of ordinary skill in the art, the choice of name has no effect on the intrinsic characteristics of the factors described herein, which were first disclosed in International Patent Publication No. WO 93/19179, published 30 Sep. 1993. The present inventors have chosen to adopt this newly derived terminology herein as a convenience to the skilled artisan who is familiar with the subsequently published papers relating to the same, and in accordance with the proposal to harmonize the terminology for the novel class of proteins, and nucleic acids encoding the proteins, disclosed by the instant inventors. The terms [molecular weight] kd receptor recognition factor, Stat[molecular weight], and Stat [number] are used herein interchangeably, and have the meanings given above. For example, the terms 91 kd protein, Stat91, and Stat1α refer to the same protein, and in the appropriate context refer to the nucleic acid molecule encoding such protein.

As stated above, the present invention also relates to a recombinant DNA molecule or cloned gene, or a degenerate variant thereof, which encodes a receptor recognition factor, or a fragment thereof, that encodes a DNA binding domain, or a chimeric protein containing a functionally active DNA binding domain of a STAT protein.

Diagnostic and therapeutic applications are raised by the identification of the DNA-binding domain of STAT proteins, and that C-terminal serine phosphorylation of a STAT protein appears to be required for maximum signal transduction activity. As suggested earlier and elaborated further on herein, the present invention contemplates pharmaceutical intervention in the cascade of reactions in which the STAT protein is implicated, to modulate the activity initiated by the stimulus bound to the cellular receptor.

Thus, in instances where it is desired to reduce or inhibit the gene activity resulting from a particular stimulus or factor, an appropriate antagonist of the DNA-binding domain of a STAT protein could be introduced to block the interaction of the STAT protein with its DNA binding site. Similarly, mutation of the C-terminal phosphorylation site, or introduction of a mutant STAT protein lacking such a C-terminal phosphorylation site, would be expected to lead to a decrease in the level of transcriptional activation mediated by a STAT protein containing such a serine phosphorylation site.

As discussed earlier, the antagonists of the STAT binding to DNA, or that are specific for the phosphoserine STAT proteins, may be prepared in pharmaceutical compositions, with a suitable carrier and at a strength effective for administration by various means to a patient experiencing an adverse medical condition associated specific transcriptional stimulation for the treatment thereof. Preferably, the pharmaceutical formulation will provide for transmembrane migration of the antagonists, which will be active in the cytoplasm. A variety of administrative techniques may be utilized, among them parenteral techniques such as subcutaneous, intravenous and intraperitoneal injections, catheterizations and the like. Average quantities of the recognition factors or their subunits may vary and in particular should be based upon the recommendations and prescription of a qualified physician or veterinarian.

Also, antibodies including both polyclonal and monoclonal antibodies, may possess certain diagnostic or therapeutic (inhibitory) applications and may for example, be utilized for the purpose of detecting and/or measuring conditions such as cellular activation as a result of viral infection, inflammation, or the like. For example, the STAT protein DNA-binding domain, or a peptide corresponding to a STAT protein epitope containing the phosphorylated serine residue, may be used to produce both polyclonal and monoclonal antibodies to themselves in a variety of cellular media, by such well known techniques as immunization of rabbit using Complete and Incomplete Freund's Adjuvant and the hybridoma technique utilizing, for example, fused mouse spleen lymphocytes and myeloma cells, respectively. Preferably, such proteins are conjugated to a carrier molecule, as described above. These techniques have been described in numerous publications in great detail, e.g., International Patent Publication WO 93/19179, and do not bear repeating here.

Likewise, small molecules that mimic or antagonize the activity(ies) of the receptor recognition factors of the invention may be discovered or synthesized, and may be used in diagnostic and/or therapeutic protocols.

Identification of important regions of the STAT proteins for function provides a basis for screening for drugs capable of specific interaction with the functionally relevant domains. According, in addition to rational design of compounds that bind to, and preferably competitively inhibit the functional activity of the STAT protein. i.e., antagonists, based on the structure of relevant domain, the present invention contemplates an alternative method for identifying specific binding compounds of the DNA-binding domain or the region containing phosphoserine using various screening assays known in the art.

Any screening technique known in the art can be used to screen for STAT DNA-binding antagonists. The present invention contemplates screens for small molecule ligands or ligand analogs and mimics, as well as screens for natural ligands that bind to and antagonize STAT activates in vivo.

Knowledge of the primary sequence of the STAT DNA-binding domain, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, 1990, Science 249:386–390: Cwirla, et al., 1990, Proc. Natl. Acad. Sci., 87:6378–6382: Devlin et al., 1990, Science, 249:404–406), very large libraries can be constructed ($10^6$–$10^8$ chemical entities). A second approach uses primarily chemical methods, of which the Geysen method (Geysen et al., 1986, Molecular Immunology 23:709–715; Geysen et al. 1987, J. Immunologic Method 102:259–274) and the recent method of Fodor et al. (1991, Science 251, 767–773) are examples. Furka et al. (1988, 14th International Congress of Biochemistry, Volume 5, Abstract FR:013: Furka, 1991, Int. J. Peptide Protein Res. 37:487–493), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., 1993, "Generation and screening of an oligonucleotide encoded synthetic peptide library," Proc. Natl. Acad. Sci. USA 90:10700–4; Lam et al., International Patent Publication No.

WO 92/00252, each of which is incorporated herein by reference in its entirety), and the like can be used to screen for STAT DNA-binding domain or phosphoserine region ligands according to the present invention.

The screening can be performed directly using peptides corresponding to the DNA binding domain or the region containing the phosphoserine residue. Alternatively, chimeric proteins, which contain the DNA binding domain (or the serine residue) may be used, as such proteins will contain the element specifically under investigation. Specific examples of such chimeric proteins are disclosed in the Examples, infra.

The reagents that contain the STAT DNA-binding domain (e.g., the approximately 100 amino acid residue polypeptide, or a chimeric protein), or the serine residue, can be labeled for use in the screening assays. In one embodiment, the compound may be directly labeled. In another embodiment, a labeled secondary reagent may be used to detect binding of the compound to a solid phase support containing a binding molecule of interest. Binding may be detected by in situ formation of a chromophore by an enzyme label. Suitable enzymes include, but are not limited to, alkaline phosphatase and horseradish peroxidase. Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels.

As suggested earlier, the diagnostic method of the present invention comprises examining a cellular sample or medium by means of an assay including an effective amount of a reagent that specifically binds to a serine-phosphorylated STAT protein. Preferably, such a reagent is an antibody, preferably an affinity-purified polyclonal antibody, and more preferably a mAb. In addition, it is preferable for the anti-recognition factor antibody molecules used herein be in the form of Fab, Fab', $F(ab')_2$ or F(v) portions or whole antibody molecules. As previously discussed, patients capable of benefiting from this method include those suffering from cancer, a pre-cancerous lesion, a viral infection or other like pathological derangement. Methods for determining and optimizing the ability of anti-recognition factor antibodies to assist in the examination of the target cells are all well-known in the art.

In a specific aspect, the present invention relates to detection of both phosphotyrosine and phosphoserine on a STAT protein, which is indicative of maximum activity of the STAT protein, and thus an indicator of the degree of cellular activation. Since cellular activation is associated with certain pathological states, as discussed above, the present invention provides an advantageous method for evaluating cellular activation. Moreover, the present invention is the first instance known to the inventors in which the specific tyrosine phosphorylation activation pathway and the general serine phosphorylation activation pathway cross in the same trascription activation factor. Accordingly, this discovery has important implications for detection of diseases or disorders, i.e., pathological conditions, associated with cellular activation.

Detection of phosphorylation of tyrosine and serine can be accomplished by any techniques known in the art, including measuring the level of phosphorylation per unit mass of protein; using specific phosphatases and an appropriate detection system to detect specific phosphorylation; using antibodies generated against the phosphorylated forms of the proteins; or using well known biochemical techniques, as described in the Examples, infra.

The present invention further contemplates therapeutic compositions useful in practicing the therapeutic methods of this invention. A subject therapeutic composition includes, in admixture, a pharmaceutically acceptable excipient (carrier) and one or more of an antagonist of STAT binding to DNA, e.g., a molecule that specifically interacts with the DNA-binding domain of a STAT protein, as described herein as an active ingredient.

Alternatively, a mutant STAT, which has been mutated in the DNA-binding domain or in the serine phosphorylation site can be introduced into the cells of a subject. According to the present invention, the presence of such mutant forms of the STAT proteins, which are capable of interacting with the receptor, being phosphorylated on tyrosine, and translocating to the nucleus, can be used as “decoys.” Such proteins, when dimerized with other STAT proteins (either with a mutant or wild-type form of the protein, or with another STAT protein), are expected to bind to the DNA with lower affinity, and thus be less effective at transcription activation. Similarly, such proteins that are mutated at the serine residue which is phosphorylated in the most active state would be expected to be less efficient at transcription activation. Specific mutations that lead to reduction of transcription activation activity, but have no effect on tyrosine phosphorylation or dimerization, are shown in the Example, infra.

In a preferred aspect, such a “decoy” mutant STAT protein is introduced into a cell via transgenic therapy.

The present invention contemplates preparation of a gene encoding a mutant form of a STAT protein, wherein the mutation is found in the DNA binding domain, or is a mutation of the C-terminal serine residues that is phosphorylated in the highly functional forms of the protein. As used herein, the term “gene” refers to an assembly of nucleotides that encode a polypeptide, and includes cDNA and genomic DNA nucleic acids.

A gene encoding a mutant STAT protein, whether genomic DNA or cDNA, can be isolated from any source, particularly from a human cDNA or genomic library, and mutated according to standard methods. Specific cDNA sequences encoding STAT proteins are disclosed in SEQ ID NOS:1, 3, 5, 7, 9, and 11. Methods for obtaining the STAT gene are well known in the art, as described above (see, e.g., Sambrook et al., 1989, supra). Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710). use of TAB® linkers (Pharmacia), etc. PCR techniques are preferred for site directed mutagenesis (see Higuchi, 1989, “Using PCR to Engineer DNA”, in *PCR Technology: Principles and Applications for DNA Amplification*, H. Erlich, ed., Stockton Press, Chapter 6, pp. 61–70).

Accordingly, any animal cell potentially can serve as the nucleic acid source for the molecular cloning of a STAT gene. The DNA may be obtained by standard procedures known in the art from cloned DNA (e.g., a DNA “library”), by chemical synthesis, by cDNA cloning, or by the cloning of genomic DNA, or fragments thereof, purified from the desired cell (See, for example, Sambrook et al., 1989, supra, Glover, D. M. (ed.), 1985. DNA Cloning: A Practical Approach, MRL Press, Ltd., Oxford. U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The nucleotide sequence coding for a mutant STAT protein, can be inserted into an appropriate expression vector, i.e., a vector which contains the necessary elements for the transcription and translation of the inserted protein-coding sequence. Such elements are termed herein a "promoter." Thus, the nucleic acid encoding the mutant STAT protein of the invention is operatively associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding a STAT and/or its flanking regions.

In another embodiment, a chimeric STAT protein or mutant STAT protein can be prepared, e.g., a glutathione-S-transferase (GST) fusion protein, a maltose-binding (MBP) protein fusion protein, or a poly-histidine-tagged fusion protein, for expression in bacteria. Expression of a STAT protein as a fusion protein can facilitate stable expression, or allow for purification based on the properties of the fusion partner. For example, GST binds glutathione conjugated to a solid support matrix, MBP binds to a maltose matrix, and poly-histidine chelates to a Ni-chelation support matrix. The fusion protein can be eluted from the specific matrix with appropriate buffers, or by treating with a protease specific for a cleavage site usually engineered between the STAT polypeptide and the fusion partner (e.g., GST, MBP, or poly-His). Furthermore, the present invention contemplates fusions between a domain from one STAT protein in the site of the corresponding domain of a second STAT protein. Such chimeric constructs are specifically exemplified in the Examples, infra.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant mutant or chimeric STAT of the invention, or functional fragment, derivative or analog thereof, may be expressed chromosomally, after integration of the protein coding sequence by recombination. In this regard, any of a number of amplification systems may be used to achieve high levels of stable gene expression (See Sambrook et al., 1989, supra).

The cell into which the recombinant vector comprising the nucleic acid encoding the mutant or chimeric STAT is cultured in an appropriate cell culture medium under conditions that provide for expression of the protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a protein may be controlled by any promoter/enhancer element known in the art, but these regulatory elements must be functional in the host selected for expression. Promoters which may be used to control gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797). the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals.

Vectors are introduced into the desired host cells by methods known in the art, e.g., transfection, electroporation, microinjection, transduction, cell fusion, DEAE dextran. calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

In one embodiment, a gene encoding a mutant STAT protein is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a particular locus, e.g., the organ implicated in the rejection episode, can be specifically targeted with the vector. Examples of particular vectors include, but are not limited to, a defective herpes virus 1 (HSV1) vector (Kaplitt et al., 1991, Molec. Cell. Neurosci. 2:320–330), an attenuated adenovirus vector, such as the vector described by Stratford Perricaudet et al. (1992, J. Clin. Invest. 90:626–630), and a defective adeno-associated virus vector (Samulski et al., 1987, J. Virol. 61:3096–3101; Samulski et al., 1989, J. Virol. 63:3822–3828).

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a protein (Felgner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancrease, liver, kidney, and the brain. Lipids may be chemically coupled to other molecules for the purpose of targeting (see Mackey, et. al., 1988, supra). Targeted peptides, e.g., hormones or neurotransmitters, and proteins such as antibodies or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of recognition factor binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the factor/factor synthesis promoter antagonist or analog thereof, and one or more of the following active ingredients: an antibiotic, a steroid. Exemplary formulations are well known in the art, e.g., as disclosed in International Patent Publication WO 93/19179.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined transcriptional activity or predetermined transcriptional activity capability in suspected target cells, as set forth above. In accordance with the testing techniques discussed above, one class of such kits will contain at least a reagent capable of specifically binding to the receptor STAT protein, and means for detecting binding of the reagent to a STAT protein. Preferably, a specific binding reagent specific for phosphotyrosine, and a second specific binding reagent specific for phosphoserine, are used. In a specific aspect, such a reagent is an antibody. Means for detecting binding may be a label on the antibody (labels have been described above), or a label on a STAT protein or fragment thereof. The kits may also contain peripheral reagents such as buffers, stabilizers, etc.

The present invention may be better understood by reference to the following Examples, which are provided by way of exemplification and not limitation.

EXAMPLE 1

FUNCTIONALLY ACTIVE REGIONS OF SIGNAL TRANSDUCER AND ACTIVATOR OF TRANSCRIPTION (STAT) PROTEINS

Stat1 and Stat3 are two members of the ligand-activated transcription factor family that serve the dual functions of signal transducers and activators of transcription. While the two proteins select similar (but not identical) optimum binding sites from random oligonucleotides, differences in their binding affinity were readily apparent with natural STAT binding sites. To take advantage of these different affinities, chimeric Stat1:Stat3 molecules were used to locate the amino acids that could discriminate a general binding site from a specific binding site. The amino acids between residues ~400 and ~500 of these ~750 amino acid long proteins determine the DNA binding site specificity. Mutations within this region result in Stat proteins which are activated normally by tyrosine phosphorylation and which dimerize, but have greatly reduced DNA binding affinities.

Methods

Cell Culture, Cytokines, and Antisera. Human U3A cells, HepG2 cells, and COS-1 cells were maintained in DMEM supplemented with 10% bovine calf serum. Transfection of cells and selection of stable cell lines were carried out by standard procedures (Shuai et al., 1993, Science 261:1744). Treatment of cells with cytokines was for 15 minutes unless otherwise noted. IFN-γ (a gift from Amgen) was used at a concentration of 5 ng/ml, IFN-α was used at a concentration of 500 I.U./ml. IL-6 (UBI) was used at a concentration of 30 ng/ml. EGF was used at 50 ng/ml. Cytoplasmic and nuclear extracts were prepared as described (Sadowski and Gilman, 1993, Nature 362:79). For immunoprecipitation of cell extracts, Stat1 or Stat3 carboxyl terminal antiserum was used at a 1:200 dilution. Immobilized FLAG-specific monoclonal antibody was used for precipitation according to the manufacturer's instructions (Kodak). Phosphotyrosine-specific monoclonal antibody PY20 was used at 1:2000 dilution according to the manufacturer's instructions (Transduction Laboratories).

Plasmid Construction. Expression plasmid pRcCMV (Invitrogen) carrying Stat1 or Stat3 cDNA (Improta et al., 1994, Proc. Natl. Acad. Sci. USA 91:4776; Zhong et al., 1994, Science 264:95) was used for all cell lines. All of the recombinant STAT proteins were constructed by PCR amplification using Vent Polymerase (NEB) and verified by DNA sequencing. The chimeric Stat1 and Stat3 cDNAs included the FLAG epitope [Kodak IBI; (Hopp et al., 1988, Bio/Technology 6:1204)] to easily identify the recombinant proteins.

Electrophoretic Mobility Shift Assay. Gel mobility shift assays were carried out as described (Levy et al, 1989, Genes & Devel. 3:1362). Double stranded oligonucleotide probes were synthesized for use as the probe with 5'-GATC protruding ends. Probe sequences used in this study are:
SIE: 5'-CAGTTCCCGTCAATCAT-3' (SEQ ID NO:19)
M67: 5'-CATTTCCCGTAAATCAT-3' (SEQ ID NO:20)
Ly6E: 5'-ATATTCCTGTAAGTGAT-3' (SEQ ID NO:21)
GRR: 5'-GTATTTCCCAGAAAAGG-3' (SEQ ID NO:22)
S1: 5'-GTTGTTCCGGGAAAATT-3' (SEQ ID NO:23)
S3: 5'-TATTTCCGGGAAATCCC-3' (SEQ ID NO:24)

Binding Site Selection. In vitro, binding site selection for Stat1 was carried out essentially according to the method of Pollock and Triesman. IFN-γ treated BUD 8 fibroblast nuclear extracts were mixed with a double stranded random 176 base oligomer and immunoprecipitated with antiserum specific for Stat1 and protein A agarose. The co-purifying DNA was isolated, amplified by polymerase chain reaction, and analyzed for binding by EMSa. Following five rounds of selection, Stat-specific complex was observed, eluted from the gel, and subcloned. To obtain the Stat3 optimum site, nuclear extracts from EGF-treated COS 1 cells transfected with Stat3 expression vector were bound to the random oligomer and applied to an EMSA gel. The region corresponding to the mobility of the Stat3 gel shift on one of the 76 bp Stat1-selected sites was excised and the DNA amplified by PCR. Following 5 rounds of selection from the gel, the resulting complex was supershifted by Stat3 specific antiserum and the DNA isolated from the supershifted complex eluted from the gel, amplified and subcloned.

Results

In vitro binding site selection for Stat1 and Stat3. To determine whether Stat1 and Stat3 homodimers preferred different high affinity oligonucleotide binding sites, we carried out synthesis of a set of deoxyoligonucleotides 76 bases long: a random stretch of 26 bases was sandwiched between two constant 25 oligonucleotide regions that could be used as PCR primers. Stat1 optimum binding sites were determined first. Stat1 activation was carried out by IFN-τ treatment of Bud-8 fibroblast cells and total cell extracts were exposed to the random deoxyoligonucleotide mixture. Stat1 COOH-terminal antiserum (Schindler et al., Science 257:809–815) was used to immunoprecipitate the protein/DNA complexes followed by PCR amplification of the DNA in the precipitate (Pollock and Triesman, 1990, Nucl. Acids Res. 18:6197–6204). Five such cycles were carried out and individual DNA segments were cloned after the final amplification. Sequencing of 55 individual clones demonstrated a clear consensus binding site with strong similarity to the earlier identified GAS elements (Decker et al., 1991, EMBO J. 10:927–932; Lew et al., 1991, Mol. Cell. Biol. 11:182–191; Darnell et al., 1994, Science 264:1415–1421; FIG. 1A). The most prominent feature of the selected sequence was a 9 base pair inverted repeat with TTCCC/G as the half site consensus, a feature consistent with the fact that Stat1 binds DNA as a dimer (Shuai et al., 1994, Cell 76:821–828). The symmetry around the central C or G [designated position zero] is also reflected in the flanking sequence by a strong preference for A at position −6 and T at +6. There was also a preference at position +7 for a G but position −7 did not show a preference suggesting that the flanking sequences surrounding the core sequence may contribute to optimum binding.

Figure 1B:
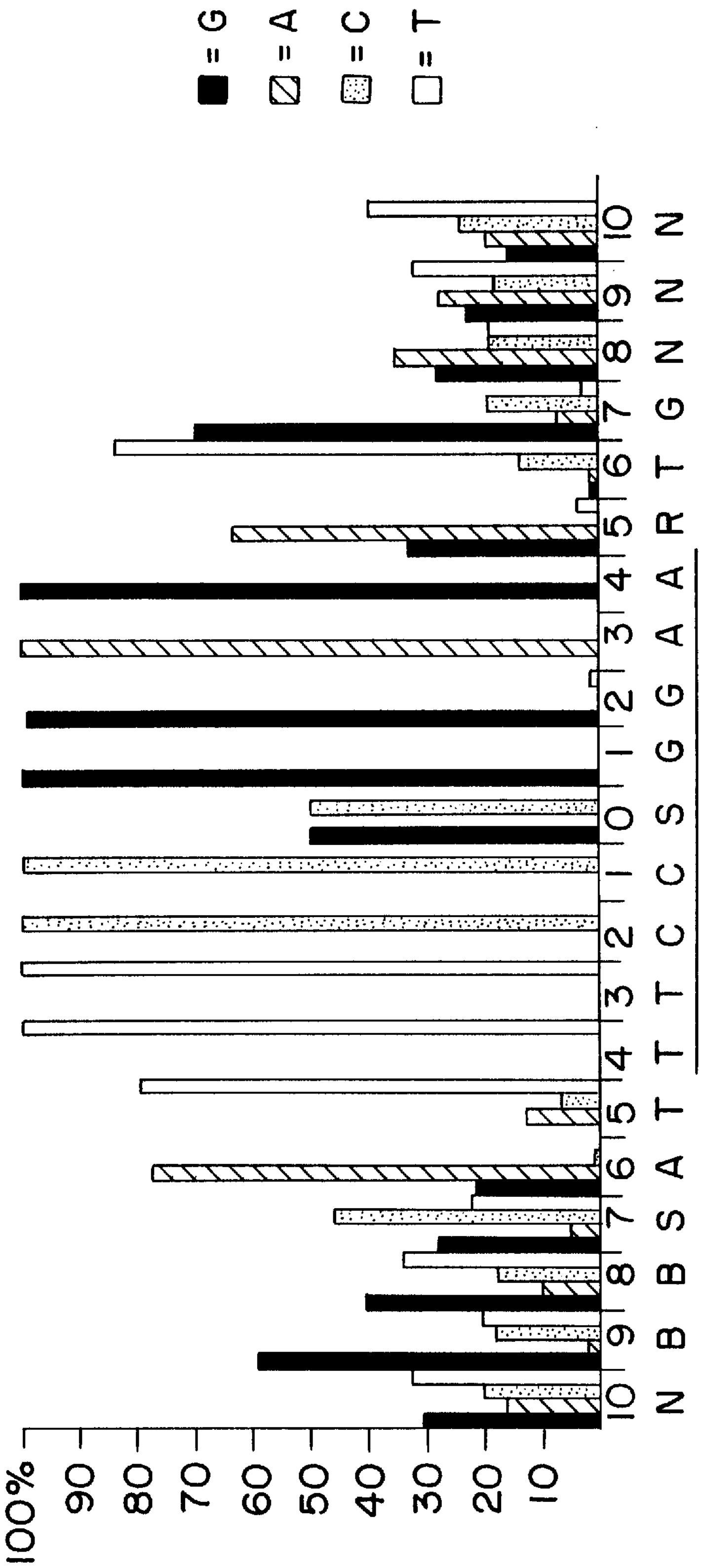
Figure 1C:
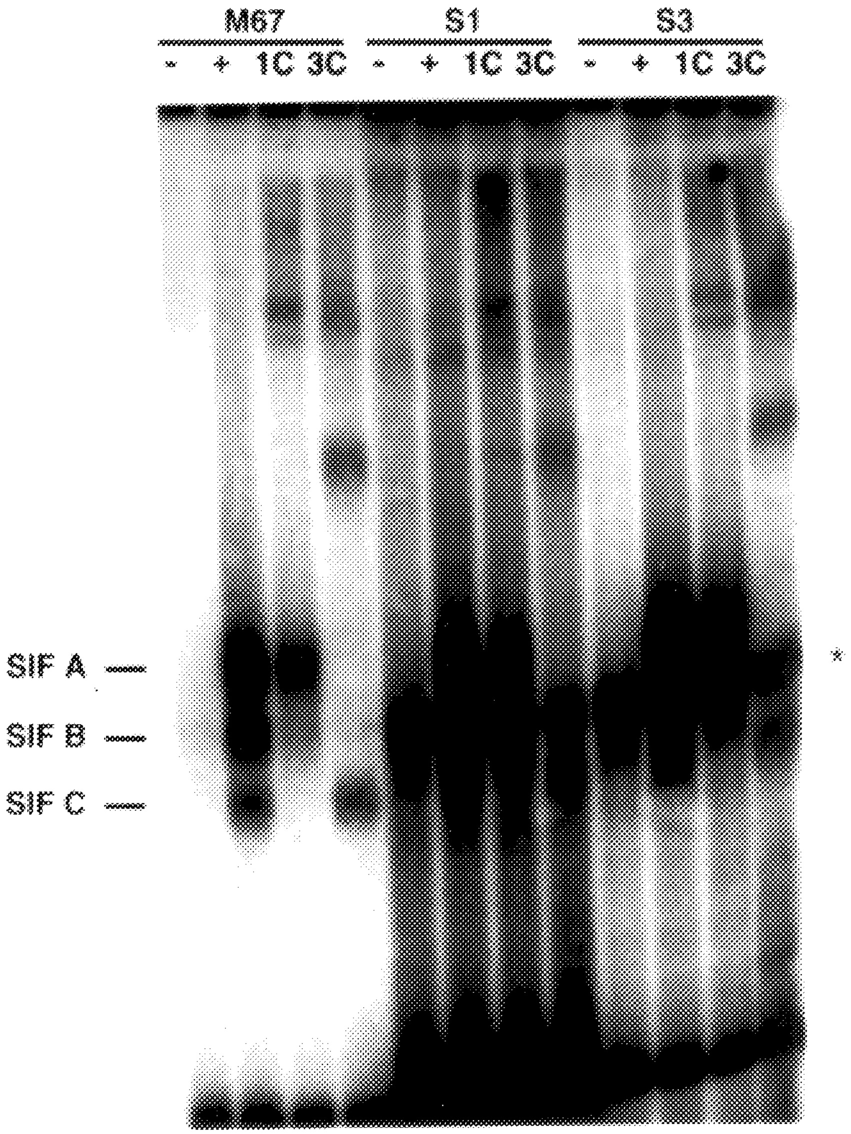

A double-stranded deoxyoligonucleotide of 22 base pairs containing in its center the consensus core sequence (TTCCCGGAA) (SEQ ID NO:25) was synthesized and used as probe in the electrophoretic mobility shift assay (EMSA) (Fried and Crothers, 1981, Nucl. Acids Res. 9:6505–6525); Levy et al., Genes & Devel. 3:1362–1372; FIG. 1B). Extracts were used from both IFN-τ treated HepG2 cells and HepG2 cells treated with a high dose of IL-6 which induces three well recognized bands (Sadowski et al., 1993, Nature 362:79–83) described as SIF A, SIF B, and SIF C because there are three DNA binding complexes inducible by medium from cells expressing the sis oncogene (SIE, sis-inducible element; SIF, sis-inducible factor (Wagner et al., EMBO, 1990, EMBO J. 9:4477–4484). The SIF C complex is identical in mobility and protein content to the IFN-τ induced complex (Sadowski et al., 1993, Science 261:1739–1744) and is therefore a Stat1 homodimer. This complex reacts with Stat1 specific antiserum. The SIF A complex which migrates more slowly (most likely due to a greater number of positively charged amino acids in addition to a slightly longer polypeptide chain) reacts with the Stat3 antiserum (Zhong et al., 1994, Science 264:95–98) and is considered to contain a Stat3 homodimer. The SIF B complex which migrates between complex A and C reacts with both Stat1 and Stat3 antisera is considered a Stat1:3 heterodimer. [These earlier conclusions are supported by results in FIG. 1*b*, lanes 1–4 with synthetic oligonucleotide M67 (Wagner et al., 1990, EMBO J. 9:4477–4484) as the labeled DNA probe.] The Stat1 selected consensus oligonucleotide bound weakly to some protein in untreated cells (lane 5, FIG. 1*b*) but also bound strongly to the induced STAT proteins that form SIF A, B and C. Thus, it seemed possible there would be overlap of the Stat1 optimum binding site and any Stat3 response element.

To determine the optimum binding site for Stat3, extracts were used that contained high levels of activated Stat3 with much less Stat1. This was achieved by preparing extracts of EGF-treated, Stat3 transfected COS cells as the source of binding activity (Zhong et al., 1994. Science 264:95–98); the activated Stat3 homodimer bound to the random 76 base pair probe (corresponding to the SIF A band) was identified by electrophoretic separation. The position of SIF A was marked using one of the Stat1-selected 76 nucleotide high affinity sites which binds to Stat3 as shown in FIG. 1B. The gel electrophoretic band was excised, DNA amplified and five cycles of gel shifts and amplification were carried out before cloning of individual examples of DNA from the SIF A complex. Sequencing of 55 individual clones with Stat3-selected sequences also revealed a clear consensus sequence which was identical in the core sequence TTCC[C or G]GGAA to that selected by the Stat1 (FIG. 1A). Just as did the Stat1 site, the Stat3 selected site contained an A or T at positions +6 or −6, respectively, but in addition the Stat3 site also showed a strong preference of A and T at positions +5 and −5 making a 13 nucleotide palindrome the favored Stat3 site. As with Stat1, a preference for G at position +7 was not matched by a C at position −7. Also, position −9 was G in about 60% of cases. As with Stat1, these flanking sequence preferences may contribute to the optimum site.

An oligonucleotide probe was synthesized to represent the Stat3 optimal site (position −9 to +9) and used in a gel shift experiment (FIG. 1B, lanes 9–13). Since the Stat1 optimum site core is contained within the Stat3 probe, it was not surprising that, like the selected Stat1 probe, the Stat3 probe bound well to all of the SIF complexes. Unfortunately, the Stat3 consensus probe used also bound even more strongly to a constitutively active protein (marked by the asterisk in FIG. 1B) that comigrates closely with SIF B, obscuring the center section of the gel shift pattern. It was noted that the Stat3 consensus probe bound somewhat better in the SIF A complex from which it had been selected than did the Stat1 optimum probe, but this was estimated by competition experiments to be only a 3–5 fold difference. While it is clear that such relatively minor differences might be important at individual sites in genomic DNA, we could not use these "consensus" probes to easily distinguish the binding affinities of Stat1 from Stat3.

Figure 2:
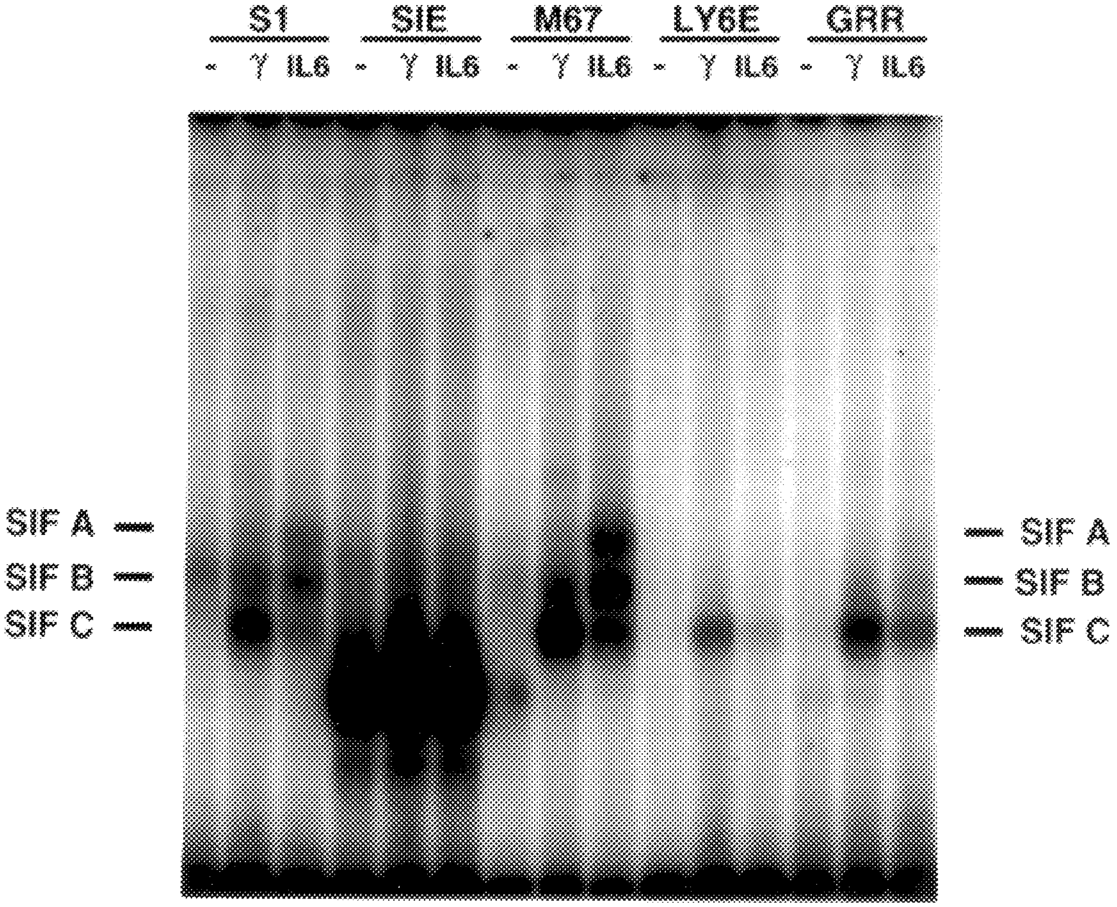
FIG. 2 Binding of Stat1 and Stat3 to known GAS Elements Reveals Differential Binding Patterns. Nuclear extracts from untreated (−), IFN-γ treated (γ), and IL-6 treated HepG2 cells were incubated with the indicated probes and DNA protein complexes detected by EMSA. Positions of SIF A, SIF B, and SIF C are marked. S1=Stat1 selected consensus sequence. SIE=cfos promoter sis-inducible element. M67=hyperactive mutated form of SIE. Ly6E=GAS element from the Ly6E gene promoter. GRR=FcγR1 promoter IFN-γ response element.

Stat protein binding to natural sites. Previously identified Stat protein binding elements were next examined to determine if any sites gave sufficient specificity to distinguish easily Stat1 from Stat3 binding. Oligonucleotide probes representing GAS [IFN-τ activates sites (Decker et al., 1991, EMBO J. 10:927–932; Lew et al., 1991, Mol. Cell. Biol. 11:182–191) from the murine surface antigen Ly6e (Kahn et al., 1993. Proc. Natl. Acad. Sci. USA 90:6806–6810), IFN-τ response region (the GRR) of the FcgR1 gene (Pearse et al., 1993, Proc. Natl. Acad. Sci. USA 90:4314–4318), the c-fos SIE and its high affinity mutated form, M67 (Wagner et al., 1990, EMBO J. 9:4477–4484), and the optimum Stat1 or Stat3 binding sites (FIG. 2). Using extracts from HepG2 cells treated with IL-6 that contain SIF A, SIF B and SIF C binding activity, differences were clearly observed among these probes. The M67 SIE bound probes to form in near equimolar amounts the SIF A, SIF B and SIF C complexes while the natural c-fos site gave a very weak signal with STAT proteins. The Stat1 optimum core sequence was also bound by all of the SIF species, but with overall lower affinity as judged by the intensity of the binding signal. Thus, the M67 probe binds well to both Stat1 or Stat3 but cannot distinguish between them. In contrast, the GRR and Ly6e probes were both bound by the SIF C protein (Stat1 homodimer), with the GRR probe giving 2–3 fold more binding than the Ly6e probe. Both probes were bound poorly by the SIF B complex, the heterodimer of Stat3 and Stat1. Most significantly, the SIF A complex that represents Stat3 homodimer binding was not observed with the GRR or Ly6e probes unless the autoradiograms were overexposed. Thus, the two closely related proteins Stat3 and Stat1 differ in their ability to recognize these two natural GAS elements. Other GAS elements tested (from the IRF1 gene, the alpha-2 macroglobulin gene, the guanylate binding protein gene, and the B-casein gene) displayed intermediate binding properties with respect to Stat1 and Stat3 binding and were not useful for this analysis (data not shown).

Localization of specific DNA binding region of Stat proteins. We proceeded to use the differential binding affinities of Stat1 and Stat3 to the GRR compared to uniform binding to the M67 SIE probe in determining the STAT protein region that discriminates between the probes. The Stat1 −SH2 group lies between amino acids 573 and 700 (resides ~6600–700) (Fu, 1992, Cell 70:323–335; Schindler et al., 1992, Proc. Natl. Acad. Sci. USA 89:7836–7839, Schindler et al., 1992, Science 257:809–815) and the Y that becomes phosphorylated is at residue 701. Mutations at the Y701 and in R602 in the pocket of Stat1 −SH2 have proved the necessity of these regions in STAT tyrosine phosphorylation and subsequent activation as a DNA binding protein (Shuai et al., 1993, Science 261:1744–1746; Shuai et al., 1993, Nature 366:580–583; Shuai et al., 1994, Cell 76:821–828). Moreover, the −SH2 region of Stat1 has been shown to confer IFN-τ inducibility on Stat2 (Heim et al., 1994, Science, in press). Thus, a chimeric protein with the Stat1 −COOH terminus can be activated by IFN-τ. Stat3 also contains an SH2 region from ~60–700 and a Y in a position comparable to Stat1 at residue 705 but Stat3 is not activated by IFN-τ (Zhong et al., 1994, Proc. Natl. Acad. Sci. USA 91:4806–4810). Mutations of the Stat3 Y residue at 705 to phenylalanine likewise blocks phosphorylation of Stat3, Z. Wen and J. E. Darnell, unpublished observations).

Figure 3:
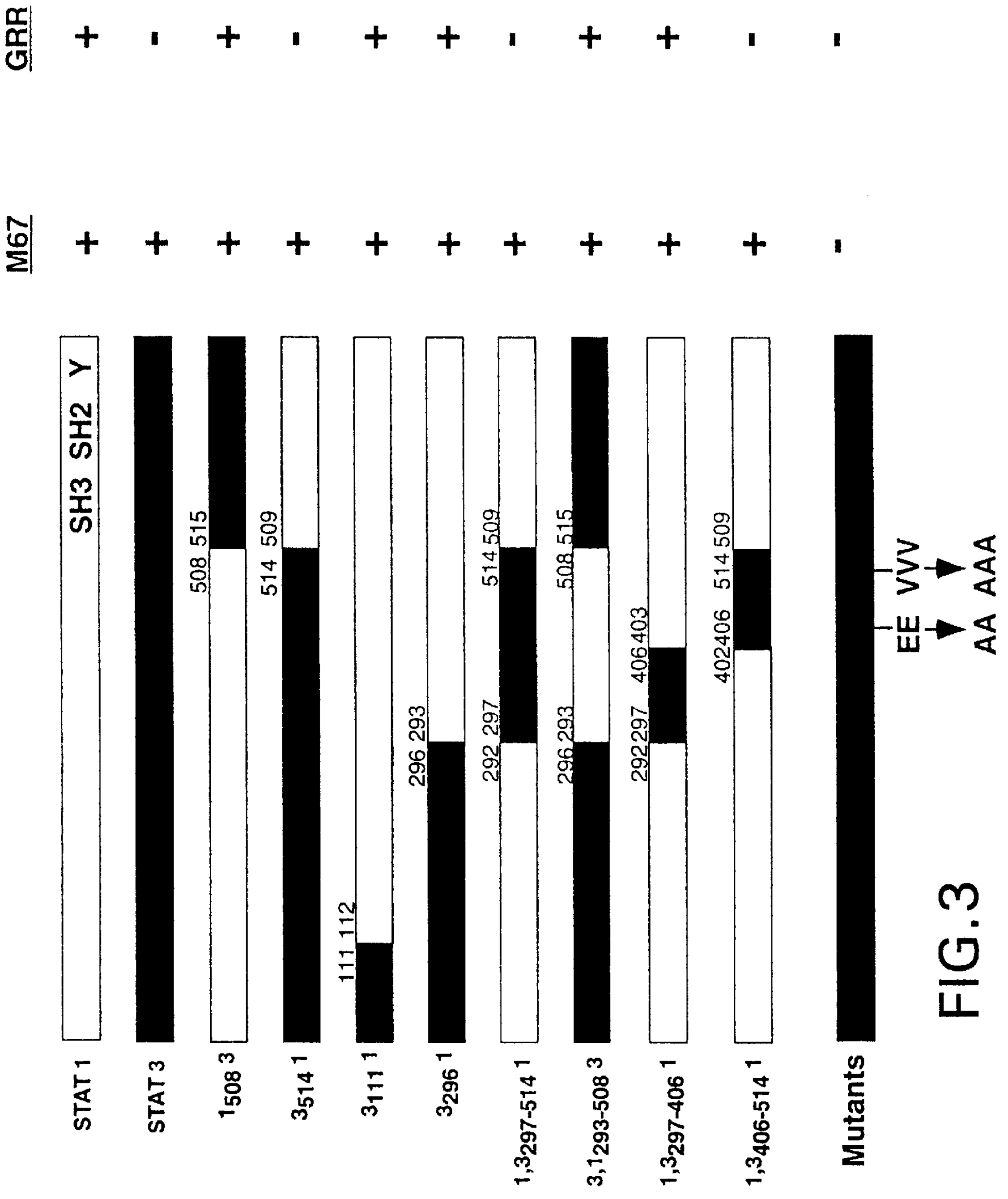
FIG. 3 Diagrammatic Representation of the Stat1/Stat3 Chimeras used in this Study. Open box depicts the Stat1 molecule and the black box depicts Stat3. The numbers above the boxes refer to the amino acid residues of Stat1 or Stat3 before and after the chimeric junction. Positions of the src homology domains (SH3, SH2) and activating tyrosine (Y) are indicated for Stat 1. Binding properties for the M67 and GRR oligodeoxynucleotides as determined in this study (see FIG. 4) are indicated to the right. The bottom box depicts the positions of the two mutations made in Stat3 (see FIG. 5). Drawn to approximate scale.

As the segment of STAT proteins from ~600 to ~750 appear to function in activation and dimerization, we focused on the $NJ_2$ terminal regions as a possible source of DNA binding specificity. Gene fusions were constructed which code for chimeric Stat proteins containing regions of Stat1 fused to Stat3 or vice versa (FIG. 3). The chimeras are named to specify the source of the fused Stat protein from NH2 to COOH terminus with the amino acid number of the joint in subscript. For example, $^{1}500^{3}$ means Stat1 amino acids 1–500 joined to Stat3 at amino acid 500. The cDNAs were transfected into U3A cells and permanent cell lines expressing the recombinant proteins were selected. U3A cells lack expression of Stat1 protein, but contain active receptors for IFN-τ or IFN-α (Pellegrini et al., Mol. Cell. Biol. 9:4605–4612; Muller et al., 1993, EMBO J. 12:4221–4228).

Stat1 (and chimeric proteins containing the Stat1 carboxyl terminal activation regions) introduced into this cell line can be activated by IFN-τ or IFN-α (Muller et al., 1993, EMBO J. 12:4221–4228; Improta et al., 1994, Proc. Natl. Acad. Sci. USA 91:4776–4780; FIG. 4). Stat3 can be activated by IFN-α in the U3A precursor cell line, 2FTGH (I. Kerr, personal comm.; C. M. Horvath, Z. Zhong and J. E. Darnell, Jr., unpublished observations), but we found that the U3A cells derived from 2FTGH by extensive mutagenesis (Pellegrini et al., 1989, Mol. Cell. Biol. 9:4605–4612) did not respond by activating the endogenous Stat3. However, the wild type Stat3 permanently introduced into U3A cells was activated by IFN-α (FIG. 3, last lane) (C. M. Horvath and J. E. Darnell, Jr., unpublished observations). Therefore, we used IFN-α to activate in U3A derived cell lines the chimeric proteins containing the Stat3 carboxyl terminal activation regions.

Figure 4A:
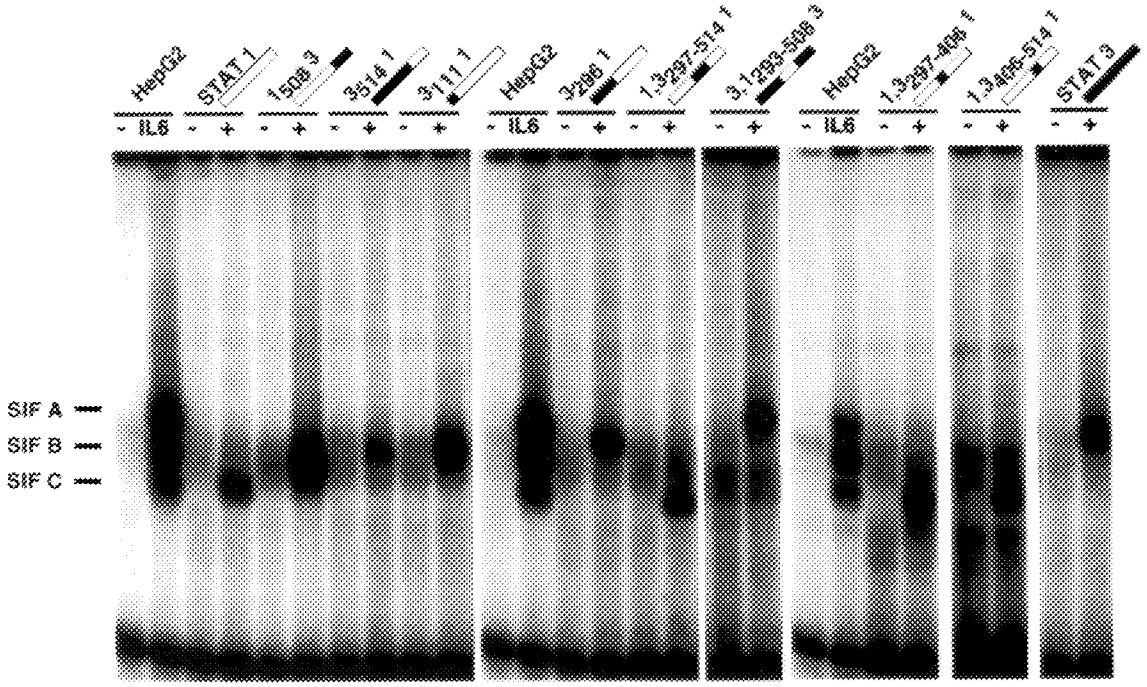
FIGS. 4A–4B Differential Binding of the Chimeric STAT Proteins. Nuclear extracts from untreated (−) and interferon treated (+) U3A cells expressing the chimeric STAT proteins were incubated with M67 probe to reveal all DNA binding complexes (FIG. 4). Positions of SIF A, SIF B, and SIF C are marked as determined from IL6-treated HepG2 cell nuclear extracts. The same extracts incubated with GRR probe (FIG. 4B). The position of SIF C from IL6-treated HepG2 cell nuclear extracts is marked, and the position where SIF A and SIF B would migrate are marked in parentheses.

Consistent with the results using IL-6 treated HepG2 extracts (FIG. 1B), extracts of U3A cells permanently transfected with either Stat1 and treated with IFN-τ or transfected with Stat3 and treated with IFN-α, displayed the same differential DNA binding properties as did the same proteins activated in HepG2 cells (FIG. 4). Activated Stat1 binds well to both M67 and GRR p robes, while activated Stat3 binds to M67 but not (or very poorly) to the GRR (FIGS. 4A and B, lanes 4 and 26). Chimeric junctions in the first ~500 amino acids were chosen based on regions of amino acid sequence identity between Stat1 and Stat3 so as not to disrupt potentially important domains of the resulting hybrid proteins. As mentioned earlier, a greater number of glutamine and aspartic acid residues plus a slightly greater length in Stat3 compared to Stat1 is the cause for the slower migration of Stat3 homodimers compared to Stat1 homodimers. In chimeric proteins, these differences were reflected in protein:DNA complexes that migrated at intermediate rates. A chimeric Stat protein containing the first 508 amino acids of Stat1 and the carboxyl terminus of Stat3 exhibited the general binding property of Stat1 in that the chimeric protein, designated $^{1}508^{3}$, bound well to both test probes and migrated just slightly slower than Stat1 (FIGS. 4A and B, lane 6). The complementary chimera, $^{3}514^{1}$ with the amino terminal 514 amino acids of Stat3 fused to the carboxyl terminus of Stat1 had the recognition property of Stat3, that is, it bound well to M67 probe, but not to GRR (FIGS. 4A and B, lane 8).

Thus, the STAT DNA recognition capacity was localized to the amino terminal 508 amino acids of Stat1 or 514 amino acids of Stat3, and was not influenced by the putative SH3 domain (~500–600), the SH2 domain (~600–700) or other sequences in the carboxyl terminal third of the molecule which itself can utilize different ligand-receptor complexes for activation (IFN-τ for Stat1 and IFN-α for Stat3).

Figure 4B:
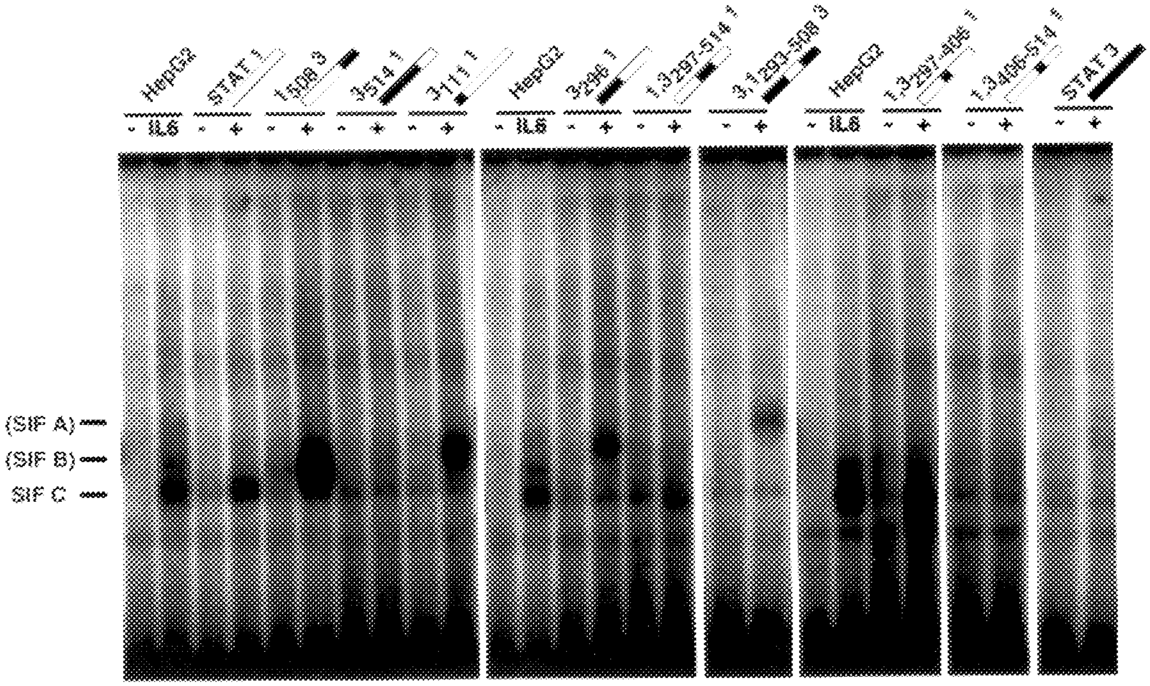

To further dissect the STAT DNA recognition region, additional chimeras were constructed containing the amino terminal 111 or 296 amino acids of Stat3 substituted into Stat1. Both recombinant molecules, $^{3}111^{1}$ or $^{3}296^{1}$, retained the binding characteristic of Stat1 (FIGS. 4A and B, lanes 10 and 14), recognizing both M67 and GRR probes. These results suggest that the amino terminal 296 amino acids do not determine the specificity of DNA sequence recognition. It seemed reasonable to infer from this set of chimeras that the region from amino acid 297 to 514 of Stat3 (or 508 of Stat1) imparted the ability to discriminate between DNA elements. To test this suggestion directly, the region of Stat1 between 292 and 509 was replaced with the Stat3 amino acids 297 to 514 (chimera $^{1,3}297,514,^{1}$) and a corresponding Stat3 with a Stat1 insertion, chimera $^{1,3}297–514,^{1}$ molecule showed that while the amino acid sequence was primarily Stat1, the recombinant molecule now bound M67 but failed to bind the GRR showing that recognition capacity of Stat3 was transferred to Stat1. Reciprocally, when chimera $^{3,1}293–508,^{3}$ was tested, the recombinant, largely Stat3 sequence could now bind well to both the M67 and GRR probes, transferring the DNA binding property of Stat1 (FIGS. 4A and B, lanes 16 and 18). We concluded that the portion of the STAT protein which recognizes the DNA response element lies between amino acids 297 and 514 of Stat3 and between amino acids 293 and 508 of Stat1. A final set of chimeric molecules that more accurately positioned the Stat3 recognition capacity was then constructed. The 200 amino acid region was divided into two approximately 100 amino acid insertions of Stat3 into Stat1. These chimeras showed that amino acids 297 to 406 left Stat1 recognition intact while insertions of amino acids 406 to 514 resulted in the transfer of Stat3 recognition (FIGS. 4A and 4B, lanes 22 and 24). We conclude that the amino acids that determine DNA binding specificity lie in this approximately 108 amino acid segment between residues 406 and 514.

Figure 5A:
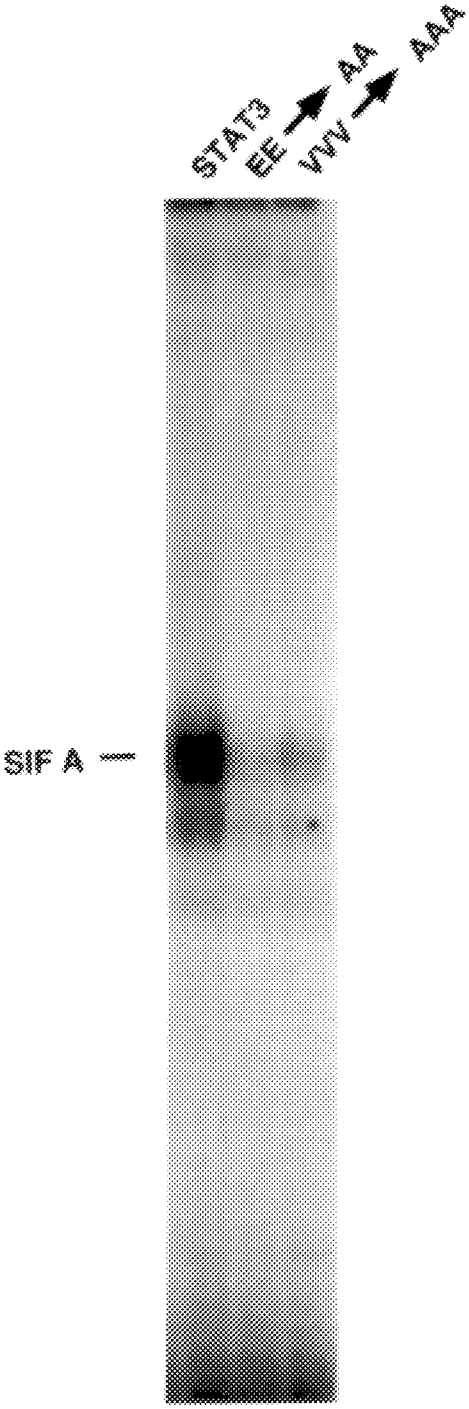
FIGS. 5A–5C Mutations in Stat3 influence DNA Binding Affinity. 5A. EMSA analysis of DNA:protein complexes. Nuclear extracts from EGF-treated COS cells transfected with Stat3, mutant EE>AA or mutant VVV>AAA (see Methods) were incubated with labeled M67 probe to reveal DNA binding complexes. Position of SIF A is marked. 5B. Phosphotyrosine immunoblotting. Extracts from the cells in panel A were immunoprecipitated with Stat3-specific antiserum, separated by SDS PAGE, transferred to nitrocellulose and probed with monoclonal antibody PY20. 5C. Co-immunoprecipitation of Stat1 and Stat3 mutants. COS cells were transfected with FLAG-tagged Stat3 or mutants along with untagged Stat1 and treated (+) or not treated (−) with EGR. FLAG immunoprecipitates were separated by SDA PAGE, transferred to nitrocellulose, and probed with Stat1 specific antiserum (top panel). STAT1 refers to transfection with Stat1 alone. Bottom panel is an immunoblot with FLAG specific monoclonal antibody to demonstrate similar expression levels in the transfected cells.
Figure 5B:
Figure 5C:
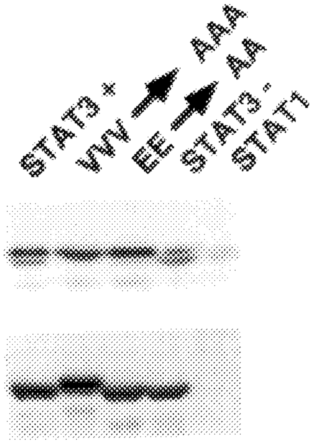

Point mutations alter DNA binding affinity. The proposed DNA recognition domain (~400–500) encompasses one of the most highly conserved regions of the STAT protein family, although no function had been previously assigned to this region either from experiment or from sequence comparison with other proteins in the data banks. To ascertain if specific amino acids within the conserved amino acid stretches were important for binding to DNA, mutations were made in two of the highly conserved regions of Stat3 in the ~400–500 region. The sequence VTEEL (residues 432 to 436) was changed to VTAAL (mutant EE>AA) or the conserved sequence SLPVVVISN (residues 458 to 466) was changed to SLPAAAISN (mutant VVV>AAA). Each mutant protein was expressed transiently in COS-1 cells [which have low endogenous Stat3 protein level (Zhong et al., 1994, Science 264:95–98) and nuclear extracts prepared following activation with EGF. Neither of the two mutants produced STAT proteins capable of binding the M67 element to the same extent as wild type STAT 3, suggesting that both mutations influenced DNA recognition. Mutant EE>AA had a more severe effect on DNA binding (nearly undetectable) than mutant VV>AA, which exhibited a distinctly reduced but still detectable binding (FIG. 5A). To determine whether these mutations blocked activation of the protein, Stat3 antiserum was used to precipitate proteins from the same COS cell extracts and the precipitates were tested by immunoblotting with antiphosphotyrosine antibody. Both mutant proteins were phosphorylated as well as the wild type protein (FIG. 5B). To determine if the mutant STAT proteins were capable of dimerization, the mutant EE>AA or mutant VVV>AAA were tagged with a FLAG epitope (Hopp et al., 1988, Bio/Technology 6:1204–1210) so that they could be distinguished from endogenous STAT 3 and transfected into COS cells along with non-tagged Stat1 cDNA. Extracts of the COS cells treated with EGF were then precipitated with monoclonal antibody to the FLAG epitope (M2). If dimerization occurred the FLAG tagged protein should carry along both endogenous and transfected activated Stat1 protein in heterodimers into the precipitate. FIG. 5C shows clearly that this was the case; Stat1 was detected in all FLAG-containing extracts, but not in control cells transfected with Stat1 alone. A small amount of Stat1 coprecipitated with FLAG-Stat3 from untreated COS cells, reflecting a low basal level of Stat3 activation. The amount of Stat1 from the treated cells was from about 5-fold greater than from the untreated cells, indicating a ligand-induced heterodimerization. These data support the conclusion that the mutant EE>AA and VVV>AAA proteins become phosphorylated in response to ligand and dimerize but cannot bind DNA as well as wild type Stat3. These results greatly strengthen the conclusion that this highly conserved region of the STAT proteins between 406 and 514 participate in recognition of and binding to GAS-like DNA response elements.

Discussion

In the past two years a large number of reports have indicated that sequences of the general motif TTNCNNNAA, the originally defined GAS consensus, can be used to detect activated STAT DNA binding (Lew et al., 1989, Mol. Cell. Biol. 9, 5404–5411; Kahn et al., 1993, Proc. Natl. Acad. Sci. USA 90:6806–6810; Pearse et al., Proc. Natl. Acad. Sci. USA 90:4314–4318; Wegenka et al., 1993, Mol. Cell. Biol. 13:276–288). We sought to determine first whether two specific STAT members that are activated by different ligands would select individual binding sites. However, optimum site selection experiments showed that both Stat1 and Stat3 preferred very similar nine base pair core elements and only minor differences in flanking sequences. The selection of highly similar optimum sites is characteristic of other DNA binding protein families such as homeobox protein (Wilson et al., 1993, Genes & Devel. 7:2120–2134), yet it is clear that specific biologic events are controlled by different family members. It is generally believed therefore that optimum binding sites may be used less commonly in evolution but that chromosomal binding sites evolved that are differentially distinguished by particular members of protein families. In line with this conjecture we found that two sites from genes known to be activated by IFN-τ, the GRR of the FcτR1 gene and the GAS site in the promoter of the Ly6e gene are in fact bound by Stat1 homodimers but not by Stat3 homodimers. The high affinity synthetic derivative of the cfos promoter, M67, in contrast is bound by both proteins and served to monitor the binding of either protein. It is interesting to note that the GRR sequence differs from the selected core sequence only at position +1 where A replaces G. Similarly, the Ly6e sequence differs from the M67 probe at only one position within the core (T replaces C at the zero position). Thus, these central nucleotides within the nine base pair are important for Stat3 binding while Stat1 binding is less demanding at these sites.

In fact, most of the genomic DNA sites (Table 1) that presumably function to bind STAT proteins do not contain the perfect nine base palindrome selected by the optimum site selection techniques. Considerable additional work will be required to determine the in vivo binding specificity of chromosomal GAS sites for particular STAT proteins especially since few experiments have yet been reported on the influence of adjacent binding sites for additional transcription factors that may bind coordinately with STAT proteins.

TABLE 1

Comparison of GAS-like Promoter Elements

| Source | Core Element | SEQ ID NO: |
|---|---|---|
| S3 | TTCCGGGAA | 26 |
| S1 | TTCCGGGAA | 27 |
| M67 SIE | TTCCCGTAA | 28 |
| cFOS-SIE | TTCCCGTCA | 29 |
| Ly6E/A | TTCCTGTAA | 30 |
| FcγR1 | TTCCCAGAA | 31 |
| GBP | TTACTCTAA | 32 |
| MIG | TTACTATAA | 33 |
| IFP53 | TTCTCAGAA | 34 |
| ICAM-1 | TTCCCGGAA | 25 |
| IRF1 | TTCCCCGAA | 35 |
| ICSBP | TTCTCGGAA | 36 |
| α2 Macroglobulin | TTCCCGTAA | 37 |
| Acid Glycoprotein | TTCCCAGAA | 38 |

The high amino acid sequence identity between Stat1 and Stat3, coupled with the inherent ability of Stat3 to distinguish between M67 and GRR elements, made it possible to define the DNA binding domain of the STAT proteins by exchanging regions between two proteins and assaying the substituted proteins for DNA site binding preference. This technique resulted in identifying residues 406 to 514 as capable of the transfer of binding specificity, since an activated Stat1 molecule containing residues 406 to 514 of Stat3 could bind only to the M67 probe and not the GRR probe while activated Stat1 itself binds to both probes. Within these 108 amino acids, Stat1 and Stat3 have only 43 amino acid differences. Counting conservative amino acid changes the sequences are even more similar. Mutations targeted to the most conserved sequences in this domain have no effect on phosphorylation or dimerization of the STAT proteins, but reduce DNA binding. We conclude that this region of the Stat1 and Stat3 proteins between 406 and 514 controls DNA binding specificity and is likely to be the DNA binding domain. Since the region between 400 and 500 is highly conserved in all the other reported STATs, it seems likely that this region will function for all family members.

In order to suggest any possible folding motifs in the putative DNA binding regions, amino acids in the 293–467 region of all the presently cloned STATs (1–6) were analyzed by computer comparison that predict secondary structure motifs by the algorithm of Chou and Fasman (FIGS. 6A–6B; Genetics Computer Group, 1991). The consensus prediction suggests a helical domain surrounding the VTEEL sequence which extends until the SLPVVV sequence which is at the beginning of a predicted beta sheet. Comparison of the possible DNA binding region we define here to known DNA binding domains does not reveal any similarity. Perhaps the STAT protein DNA binding domain will represent an unusual class of DNA binding domain. It is interesting also that this domain lies between the SH3 homology which binds proline rich sequences (Cicchetti et al., 1992, Science 257:803–806) and the conserved STAT sequence PCMPXXPXXP. If these two sequences interacted within a STAT molecule prior to phosphorylation of the protein, the DNA binding domain might be shielded in the non-phosphorylated protein or conversely such an interaction after phosphorylation might present the putative helical domain.

The exchange of this 108 amino acid domain can substitute the DNA recognition properties of these two STAT proteins. A more direct demonstration that this region is the DNA contact domain would be to transfer this domain to another class of dimeric transcription factors. We have attempted to reconstitute specific DNA recognition by grafting these sequences onto an unrelated dimerization domain from the heterologous bZIP or HLH families. STAT amino acids ~300 to ~500 were joined to the c/EBP leucine zipper and the E47 HLH domains, but demonstration of specific DNA binding by these fusion proteins has been unsuccessful so far. One reason might be that specific structural properties inherent in the STAT family of transcription factors are not provided simply by the dimerization motifs of these other factors. For example, the primary dimerization of the STAT proteins is mediated by intermolecular SH2/phosphotyrosyl interactions (~600–710) which predicts an antiparallel interaction of the two chains in this dimeric region (Shuai et al., 1994, Cell 76:821–828). Perhaps this orientation requires compensation as the chains emerge from the dimer in order to present the residues of the 400–500 region to DNA. ZIP and HLH dimerization domains are parallel with a short hinge region that allows the short DNA contact helices of those proteins to rotate correctly to form "induced sites" on the DNA (Burley, 1994, Current Opin. in Structural Biol. 4:3–11). Since the potential STAT DNA contact region has only a limited helical content, it could be that the domain must make a protein fold that has not yet been described in other DNA binding proteins.

EXAMPLE 2

MAXIMUM STAT1α ACTIVATION OF GENES REQUIRES PHOSPHORYLATION ON BOTH TYROSINE-701 AND SERINE-727

The STAT proteins are latent transcription factors that becomes activated by phosphorylation on tyrosine in response to polypeptide receptor interaction at the cell surface. The activated STATs dimerize, translocate to the cell nucleus and bind DNA. The STAT proteins were originally recognized in studies of interferon alpha (INF-α) and interferon gamma (INF-γ transcriptional activation: Stat1 and Stat2 are phosphorylated in response to INF-α, heterodimerize and together with a 48 kD protein that is not phosphorylated bind to the INF-α- specific DNA element, the ISRE. Stat1, but not Stat2, is activated by INF-γ, homodimerizes, translocates to the nucleus and binds to a different DNA element, the GAS site (INF-γ-activated site). Cell lines (U3 cell) that lack Stat1α and Stat1β, which lacks of the COOH-terminal 38 amino acids of Statα, were defective in response to either INF-α or INF-γ. Cell lines that lack Stat2 were deficient for the INF-α response only. In U3 cells, Stat1α or Stat1β suffice to restore the INF-α pathway. Stat1α can restore the INF-γ pathway but Stat1β cannot despite the fact that Stat1β is phosphorylated on tyrosine, dimerizes, enters the nucleus and can bind DNA. Since the only difference in Stat1α and 1β the lack of the COOH terminal 38 amino acids in Stat1β compared to Stat1α, this focused our attention on these residues in IFN-γ-dependent transcriptional activation.

We had earlier encountered some parallels and some differences in drug sensitivity in the INF-α and INF-γ transcriptional pathways. Both pathways are inhibited by genistein or staurosporine which are primarily inhibitors of tyrosine phosphorylation in line with the obligatory requirement for tyrosine phosphorylation for STAT dimer formation and DNA binding. However, both 6-aminopurine and H7 which are serine/threonine kinase inhibitors blocked INF-γ-induced transcription but had very much less effect on INF-α induced transcription. In addition $^{32}$p is incorporated into phosphoserine in Stat1α to a greater extent than in Stat1β. Based on all of these results, we reasoned that perhaps Stat1α contained a critical serine in the 38 terminal amino acids that served in gene activation.

The present Example demonstrates that serine 727, which is lacking in Stat1β, is in fact phosphorylated, probably constitutively in serum-grown cells. Furthermore, Stat1 protein that is mutant in serine 727 $^{Ser}727\rightarrow{}^{Ala}727$) is phosphorylated normally on tyrosine, dimerizes and binds DNA, but in cells bearing the mutant protein only about 20 percent as much INF-γ-dependent transcription occurs. Thus, the Stat1 protein requires both phosphorylation on tyrosine and serine to be fully competent in inducing transcription.

Figure 7:
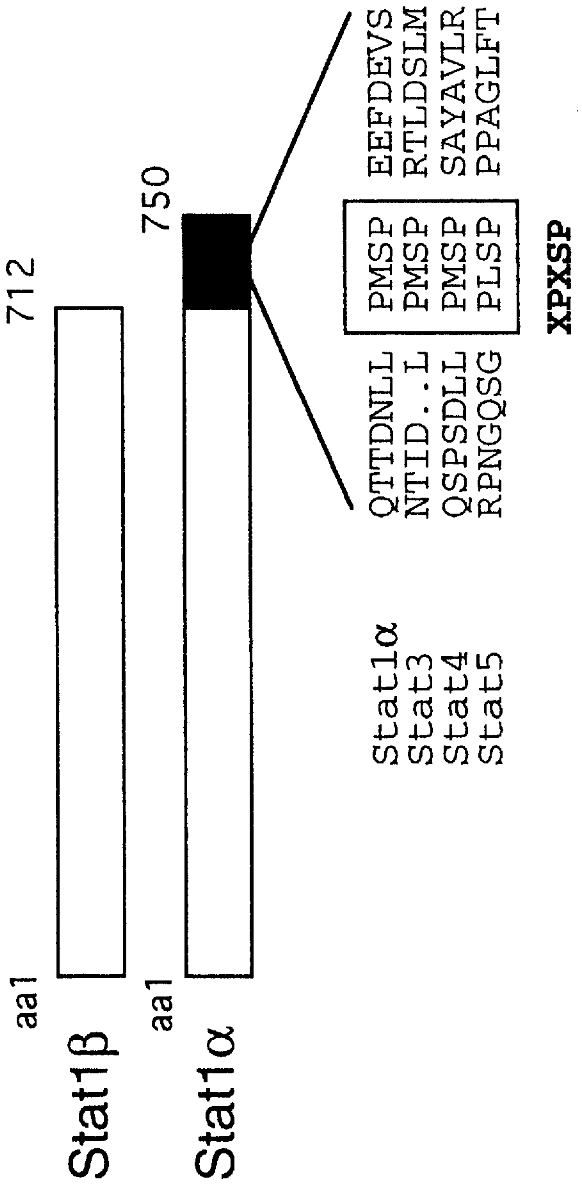
FIG. 7 Comparison of the partial carboxyl terminal sequence in a series of STAT proteins.

Sequence alignment of STATs reveals conserved PMSP box. Amino acids sequence comparison of Stats have revealed that the conserved regions are scattered throughout nearly the entire length of the proteins. However, the COOH-terminal (from about 710 to the end) of the Stats is quite diverse. FIG. 7 compares the partial carboxyl terminal sequence in a series of STAT proteins. Despite the overall diversity within this region, there is a highly conserved sequence PMSP in Stats1α, 3, 4, and 5(PLSP). The conserved sequence is lacking in the Stat1β spliced variant from the Stat1 gene, Stat2 and 6. This PMSP sequence is known to be at least part of MAP kinase recognition consensus sites.

Figure 8A:
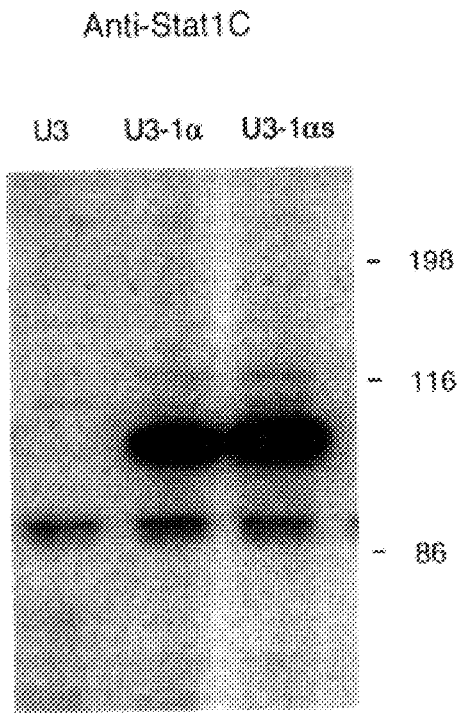
FIGS. 8A–8B. Phosphorylation of wild type and mutant proteins on tyrosine as tested by anti-phosphotyrosine antibody reaction with Stat1 immunoprecipitates separated on polyacrylamide gel (FIG. 8A). Electrophoretic gel shift assay (EMSA) with nuclear extracts of cells treated for 20 minutes with INF-$\gamma^{32}$P-labeled IRF-1 GAS as probe (FIG. 8B).
Figure 8B:
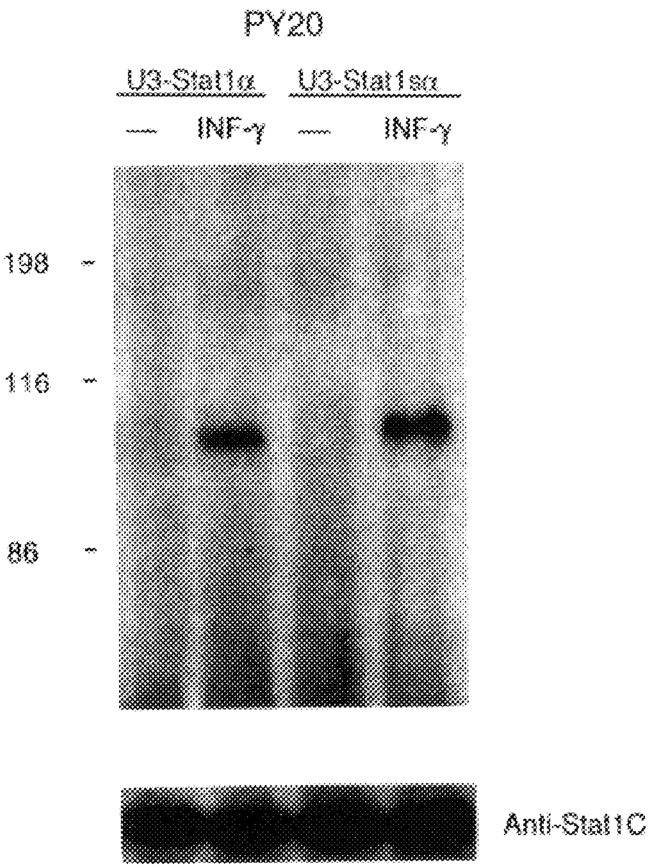
Figure 9:
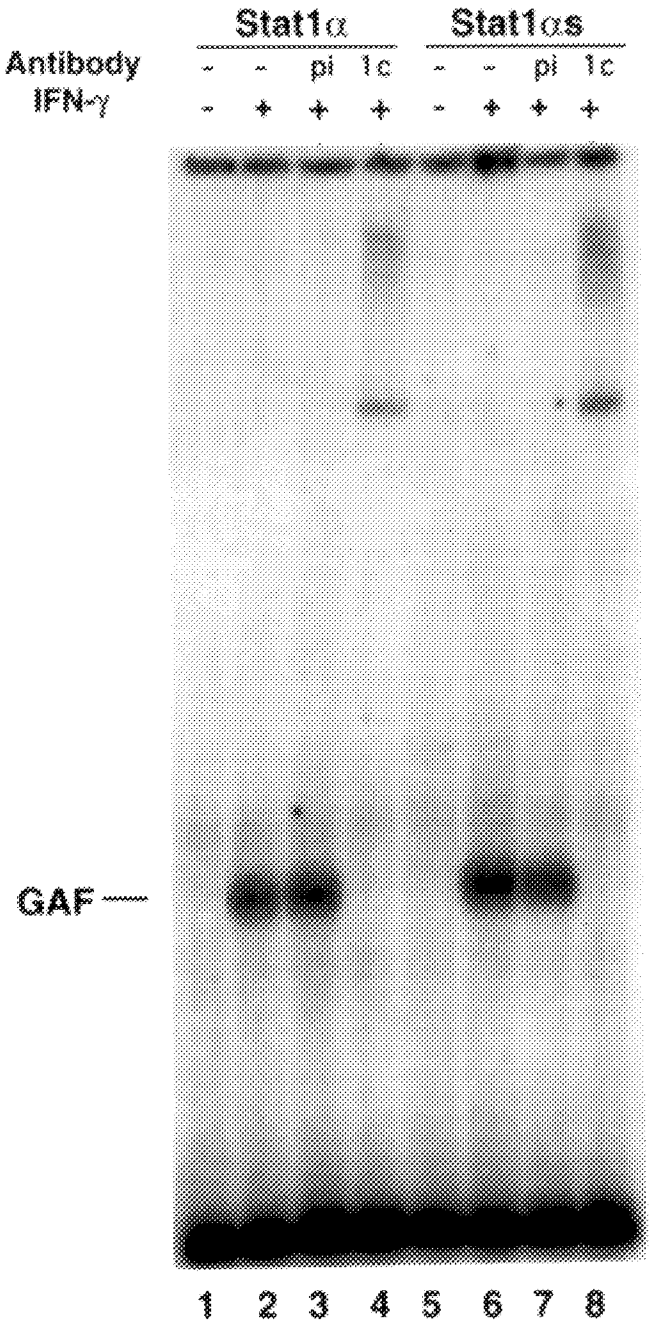
FIG. 9 Wild type and mutant Stat1α binding to IRF-1 GAS. The gel shift bands were specific because anti-Stat1C serum produced a supershift while the pre-immune serum had no affect.

Tyrosine phosphorylation and DNA binding of Stat1αs. To test the possible functional importance of serine 727 a recombinant mutant construct was prepared in which alanine was substituted for serine at residue 727. We first tested whether the serine$^{727}$ to alanine mutant(Stat1αs) had any affect on IFN-γ-induced phosphorylation on tyrosine and the subsequent development of DNA binding capacity. U3A cells that lack Stat1 protein were permanently transfected with expression vectors for wild type Stat1α or mutant Stat1αs. Individual clones of cells expressing Stat1α or Stat1αs to comparable levels (also comparable to Stat1α expression of parental 2fTGH cells) were chosen for the remainder of this work (except that described in FIG. 11). After treatment with INF-γ for 20 minutes, both wild type and mutant proteins were phosphorylated on tyrosine as tested by anti-phosphotyrosine antibody reaction with Stat1 immunoprecipitates separated on polyacrylamide gel (FIG. 8A). Electrophoretic gel shift assay (EMSA) with nuclear extracts of cells treated for 20 minutes with INF-γ showed induced DNA binding activity using the $^{32}$P-labeled IRF-1 GAS as probe (FIG. 8B). In fact both wild type and mutant bound IRF-1 GAS (FIG. 9), Ly6E GAS and M67 deoxynucleotide probes equally (data not shown). The gel shift bands were specific because anti-Stat1C serum produced a supershift while the pre-immune serum had no affect (FIG. 9).

Figure 10A:
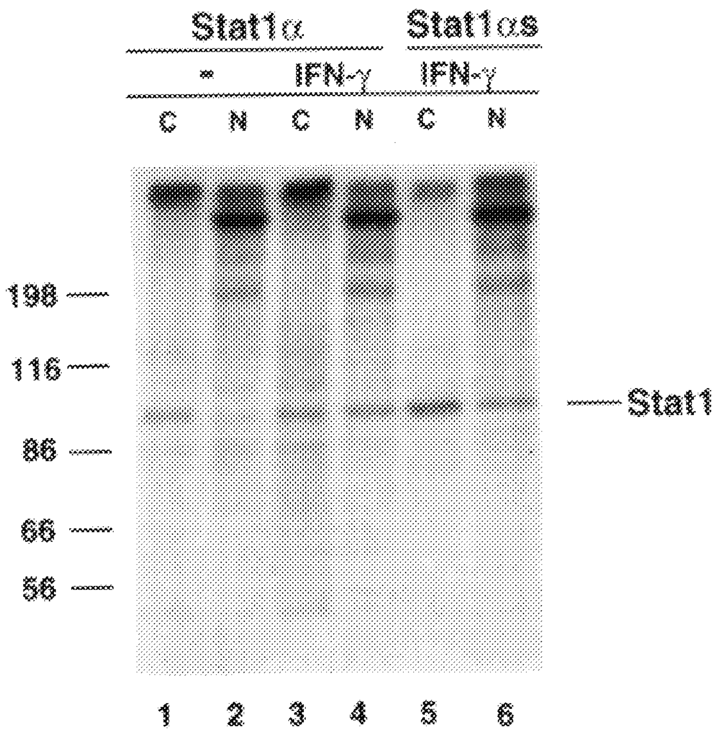
Figure 10B:
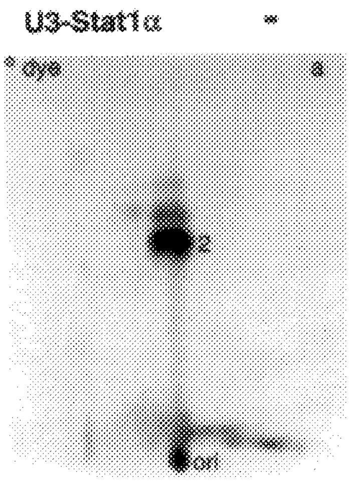
Figure 10C:
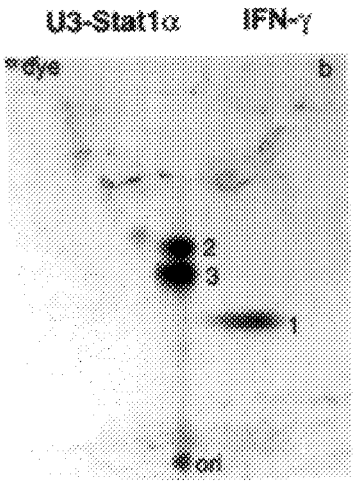
Figure 10D:
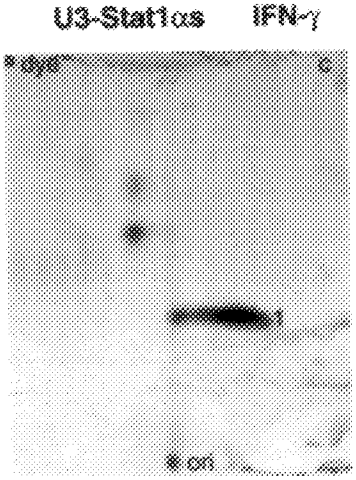
Figure 10E:
Figure 10F:
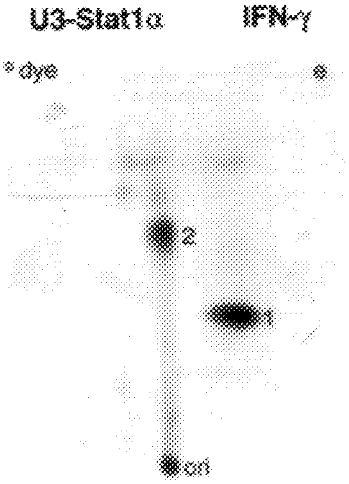
Figure 10G:
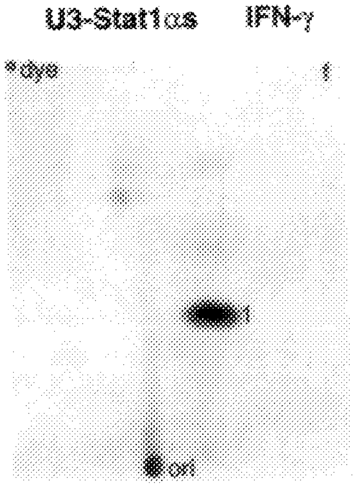

Serine727 is phosphorylated in vivo. We next determined directly whether the serine 727 residue participated in phosphorylation. Cells expressing either wild type Stat1α of Stat1αs were exposed to $^{32}$-orthophosphate for 2.5 hours and treated with INF-γ for 20 minutes. (As a control, the wild type cells were also labeled without INF-γ treatment.) Protein extracts were prepared, exposed to anti-Stat1C serum and the 91 kDa $^{32}$P-labeled band (FIG. 10A) was selected after SDS polyacrylamide gel electrophoresis. The labeled Stat1 samples were digested with trypsin, applied to thin-layer cellulose plates and separated by a two-dimensional procedure involving first electrophoresis at pH 3.5, rotating the plate 90°, followed by chromatography in 1-butanol/acidic acid/pyridine solution. Autoradiograms of the samples revealed an INF-γ-induced peptide in both wild type and mutant samples that migrated similarly to the earlier described phosphotyrosine containing peptide, GIYTEK (FIGS. 10B–G) (SEQ ID NO:39). This phosphopeptide was not present in the sample from cells expressing wild type protein that were not treated with INF-γ. A second peptide (actually a double spot possibly due to incomplete trypsin digestion) contained phosphoserine. This phosphoserine containing peptide was present in either INF-γ-treated or untreated cells containing the wild type protein but was completely absent from cells containing the mutant protein Stat1αs. Thus, a single serine to alanine mutation at residue 727 apparently removed the major target site in these cells for serine phosphorylation in Stat1.

Note that the serine phosphorylation occurred whether or not the cells were treated with INF-γ in the presence of serum and that there was more phosphoserine than phosphotyrosine (FIGS. 10H–I). This indicated that more Stat1α molecules were phosphorylated on serine than on phosphotyrosine since there is apparently a single serine of each residue that was phosphorylated, at least in U3-Stat1α complemented cells.

The site of serine phosphorylation was confirmed as residue 727 by synthesizing a 29 residue long peptide matching the human Stat1α sequence from residue 712 to 740. This peptide was treated with MAP kinase in the presence of $^{32}$P-γATP. The resulting labeled peptide was subjected to two-dimensional separation and eluted from the TLC plate. The purified $^{32}$P-labeled peptide was then digested with trypsin and the synthetic and authentic $^{32}P$ phosphoserine labeled tryptic peptides compared by two-dimensional analysis (FIGS. 10J–K). The two labeled peptides migrated very similarly (each sample was analyzed in a different chromatography tank leading to the slight differences in migration) and when mixed yield a single spot, the conventional method of demonstrating phosphopeptide identity. The experiment also established that the Stat1 peptide was a substrate for the MAP kinase which was suspected to be possible because the sequence of the potential phosphorylation site PMSP matches the known MAP kinase recognition site. Of course, this does not prove the nature of the responsible kinase inside cells.

Figure 11:
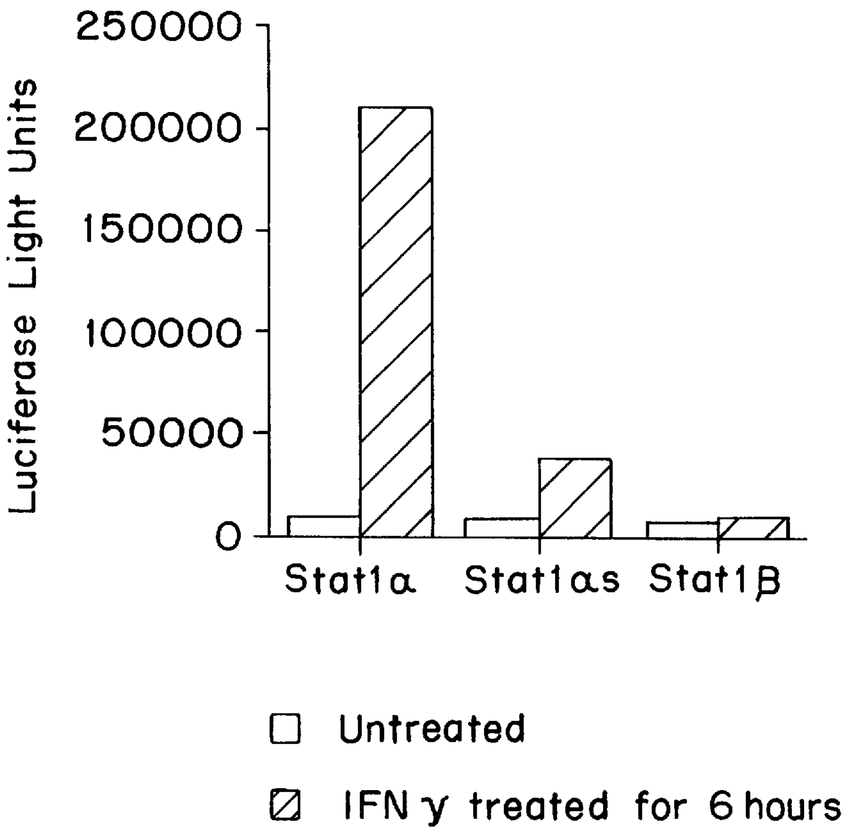
FIG. 11 Level of expression of a luciferase protein under control of three GAS sites from the promoter of the Ly6E gene in cells transfected with wild type Stat1α, mutant Stat1α, and Stat1β.

Requirement for serine 727 in Stat1α transcriptional induction. Having demonstrated that serine phosphorylation of residue 727 in Stat1 occurs in vivo, we tested for any effects on INF-γ dependent transcription. Three experiments indicated that the serine at position 727 was required for maximal IFN-γ-dependent transcriptional stimulation. First, U3 cells were transfected either with wild type Stat1α or the mutant Stat1αs plus a reporter gene construct with three GAS sites from the promoter of the Ly6E gene. After 16 hours, the cells were either treated with INF-γ or left untreated and extracts were assayed for luciferase activity six hours later. As a control Stat1β was also used. Stat1β lacks the terminal 38 amino acids of Stat1α including the serine 727 residue and is known not to drive INF-γ-induced transcription. The results of this experiment are shown in FIG. 11. The wild type Stat1α produced a 30-fold higher luciferase signal after IFN-γ induction whereas the Stat1β gave almost no increased signal. Stat1αs gave about a 5-fold increase consistent with the conclusion that a large fraction but not all of the INF-γ transcriptional response requires not only the phosphotyrosine as demonstrated earlier but requires phosphoserine on residue 727.

Figure 12A:
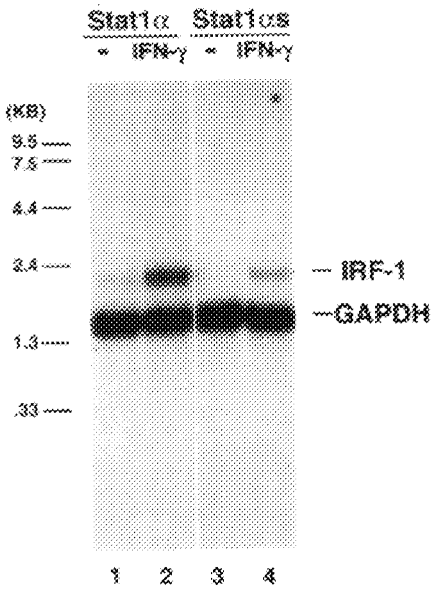
FIGS. 12A–12B.

A second experiment tested that response of endogenous genes that are transcriptionally induced by INF-γ treatment. Permanent U3A-derived cell lines containing wild type Stat1α or mutant Stat1αs were treated with INF-γ for 3 hours, poly(A)+RNA extracted, and subjected to Northern blot analysis for IRF1 mRNA, an INF-γ-induced gene (FIG. 12A). There was an about 12-fold increase in IRF1 mRNA in cells containing wild type Stat1α whereas the cells with Stat1αs were induced about 3-fold, consistent with the transfectional analysis in FIG. 11.

Figure 12B:
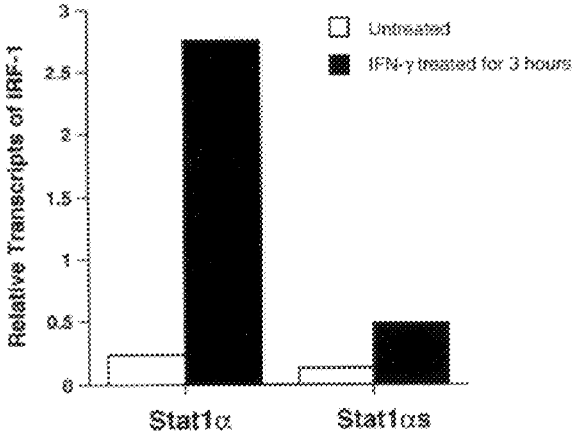

A final experiment compared the run-on transcriptional signal from the IRF1 gene in the two U3A cell derivatives. Again the INF-γ-induced transcriptional signal from the endogenous gene was significantly stronger with wild type than with mutant protein incorporated into the cells (FIG. 12B).

Discussion

This example demonstrates that a number of the STAT proteins contain a highly conserved potential serine kinase site in the carboxyl terminal residues. At least in Stat1 this residue must be phosphorylated for maximal IFN-induced transcription. Other data suggests that this serine is likely phosphorylated in the Stat3 molecule after IL-6 or EGF treatment as well. Stat1 protein containing an alanine residue 727 can be phosphorylated on tyrosine, dimerize and bind DNA but has only about 20% the transcriptional activation capacity of the wild type protein.

While this serine phosphorylation is required for maximal INF-γ transcriptional induction, it may not function at least for most genes in the INF-α pathway. Here Stat1β which lacks the serine site is equally active in forming functional ISGF-3, the transcription factor that activates INF-α sensitive genes and in IFN-α-induced mRNA accumulation.

These results in the IFN-γ pathway connect specific gene activation through the JAK-STAT pathway with one or more of the possible pathways that can result in the activation of serine kinases. In the present experiments serum grown cells that may, of course, be responding to polypeptides in the serum, apparently carry out a phosphorylation-dephosphorylation cycle of the latent Stat1α cytoplasmic proteins. This is detected as $^{32}P$ labeling of Stat1α in serum grown cells in the absence of INF-γ. Only after INF-γ stimulation however is Stat1α tyrosine phosphorylated and activated to participate in transcription. A possible conclusion from these experiments is that transcriptional activation of a STAT protein by a polypeptide ligand depends specifically on tyrosine phosphorylation to initiate the formation of transcriptively active complexes but the level of stimulation achieved depends in addition on serine phosphorylation which might come from any different serine kinases. Analysis of the importance of serine phosphorylation of the STAT proteins in general and of Stat1 in different cell types under different conditions is surely in order.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

It is further to be understood that all base-pair sizes given for nucleotides, and molecular weight or amino acid number given for protein, polypeptides, and peptides, are approximate, and are provided by way of comparison.

Various references are cited throughout this specification, each of which is incorporated herein by reference in its entirety.

What is claimed is:

1. A peptide having a DNA binding domain of a Stat protein.

2. A peptide having no more than about 110 amino acid residues and has an amino acid sequence corresponding to the sequence of the same number of amino acid residues from a DNA-binding domain of STAT protein.

3. A chimeric protein which is a fusion protein having a DNA binding domain of a Stat protein and a fusion partner.

4. The chimeric protein of claim 3 wherein the fusion partner is glutathione-S-transferase.

5. The chimeric protein of claim 3 wherein the fusion partner is maltose-binding protein.

6. The chimeric protein of claim 3 wherein the fusion partner is poly A-histidine.

7. The chimeric protein of claim 3 wherein the fusion protein facilitates stable expression of the Stat DNA binding domain.

8. The chimeric protein of claim 3 wherein the fusion protein facilitates the purification of the Stat DNA binding domain based on the properties of the fusion partner.

9. The chimeric protein of claim 3 that is labeled.

10. The chimeric protein of claim 3 wherein the Stat DNA binding domain has no more than about 110 amino acid residues and has an amino acid sequence corresponding to the sequence of the same number of amino acid residues from a DNA-binding domain of STAT protein.

11. The chimeric protein of claim 4 wherein the Stat DNA binding domain has no more than about 110 amino acid residues and has an amino acid sequence corresponding to the sequence of the same number of amino acid residues from a DNA-binding domain of STAT protein.

12. The chimeric protein of claim 5 wherein the Stat DNA binding domain has essentially of no more than about 110 amino acid residues and has an amino acid sequence corresponding to the sequence of the same number of amino acid residues from a DNA-binding domain of STAT protein.

13. The chimeric protein of claim 6 wherein the Stat DNA binding domain has no more than about 110 amino acid residues and has an amino acid sequence corresponding to the sequence of the same number of amino acid residues from a DNA-binding domain of STAT protein.

\* \* \* \* \*